(12) United States Patent
Stryjewski et al.

(10) Patent No.: US 12,233,157 B1
(45) Date of Patent: Feb. 25, 2025

(54) HYDROGEL FORMULATIONS AND METHODS AND DEVICES FOR ADMINISTRATION OF THE SAME

(71) Applicant: Pykus Therapeutics, Inc., Cambridge, MA (US)

(72) Inventors: Tomasz Pawel Stryjewski, Somerville, MA (US); James Anthony Stefater, III, Boston, MA (US); Laurence A. Roth, Windham, NH (US); Kelsey-Ann Leslie, Cambridge, MA (US)

(73) Assignee: PYKUS THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 18/783,305

(22) Filed: Jul. 24, 2024

(51) Int. Cl.
| A61K 9/06 | (2006.01) |
| A61K 9/00 | (2006.01) |
| A61K 31/25 | (2006.01) |
| A61K 31/795 | (2006.01) |
| A61K 47/54 | (2017.01) |

(52) U.S. Cl.
CPC .............. *A61K 9/0051* (2013.01); *A61K 9/06* (2013.01); *A61K 31/25* (2013.01); *A61K 31/795* (2013.01); *A61K 47/548* (2017.08)

(58) Field of Classification Search
CPC ...... A61K 9/0051; A61K 47/548; A61K 9/06; A61K 31/25; A61K 31/795
See application file for complete search history.

(56) References Cited

U.S. PATENT DOCUMENTS

| 5,258,412 A | 11/1993 | Peyman |
| 5,654,349 A | 8/1997 | Feingold et al. |
| 6,149,931 A | 11/2000 | Schwartz et al. |
| 6,828,401 B2 | 12/2004 | Nho |
| 7,115,417 B1 | 10/2006 | Chancellor et al. |
| 7,659,260 B2 | 2/2010 | Kadrmas |
| 7,833,206 B1 | 11/2010 | Lumpkin et al. |
| 9,072,809 B2 | 7/2015 | Askari |
| 9,125,807 B2 | 9/2015 | Sawhney et al. |
| 9,623,144 B2 | 4/2017 | Askari et al. |
| 9,873,769 B2 | 1/2018 | Braithwaite et al. |
| 10,874,767 B2 | 12/2020 | Stefater, III |
| 10,973,954 B2 | 4/2021 | Stefater, III et al. |
| 10,973,955 B2 | 4/2021 | Stefater, III et al. |
| 11,077,232 B2 | 8/2021 | Stefater, III et al. |
| 11,547,779 B2 | 1/2023 | Therapeutics |
| 11,883,378 B2 | 1/2024 | Roth et al. |
| 2006/0141049 A1 | 6/2006 | Lyons et al. |
| 2006/0292190 A1 | 12/2006 | Matier et al. |
| 2008/0107694 A1 | 5/2008 | Trogden |
| 2009/0017097 A1 | 1/2009 | Sawhney et al. |
| 2011/0082221 A1 | 4/2011 | Haug |
| 2012/0082730 A1 | 4/2012 | Banerjee et al. |
| 2012/0100103 A1 | 4/2012 | Park |
| 2012/0189708 A1 | 7/2012 | Van Epps et al. |
| 2014/0248231 A1 | 9/2014 | Askari et al. |
| 2015/0273108 A1 | 10/2015 | Askari et al. |
| 2016/0009872 A1 | 1/2016 | Braithwait |
| 2017/0175791 A1 | 6/2017 | Baur et al. |
| 2019/0175791 A1* | 6/2019 | Stefater, III ............ A61L 27/58 |
| 2019/0216982 A1 | 7/2019 | Roth et al. |
| 2019/0224375 A1 | 7/2019 | Stefater, III et al. |
| 2020/0338233 A1 | 10/2020 | Roth et al. |
| 2021/0007762 A1 | 1/2021 | Chang et al. |
| 2021/0077663 A1 | 3/2021 | Stefater, III et al. |
| 2021/0077664 A1 | 3/2021 | Stefater, III et al. |
| 2021/0187168 A1 | 6/2021 | Stefater, III et al. |
| 2023/0081482 A1 | 3/2023 | Wang |
| 2023/0157988 A1 | 5/2023 | Roth et al. |
| 2023/0263943 A1 | 8/2023 | Myung et al. |
| 2023/0414838 A1 | 12/2023 | Stefater |

FOREIGN PATENT DOCUMENTS

| AU | 2017295715 | 3/2022 | |
| CN | 101338036 B | 11/2010 | |
| CN | 102049067 A | 5/2011 | |
| CN | 102911493 | 2/2013 | |
| EP | 2737908 A1 * | 6/2014 | ........... A61K 31/728 |
| WO | WO-2005072768 A1 | 8/2005 | |
| WO | WO-2006078458 | 7/2006 | |
| WO | WO-2008008859 | 1/2008 | |

(Continued)

OTHER PUBLICATIONS

H. Lee, eta al. "Injectable Self-Crosslinkable Thiolated Hyaluronic Acid for Stem Cell Therapy of Atopic Dermatitis," ACS Biomater. Sci. Eng. 2022, 8, 1613-1622. (Year: 2022).*
"Two Deans' Challenges garner 90 proposals", The Harvard Gazette, https://news.harvard.edu/gazette/story/2016/03/two-deans-challenges-garner-90-proposals/, Mar. 9, 2016, accessed Jan. 8, 2019 (6 pages).
Alarake, N.Z. et al., "Mechanical properties and biocompatibility of in situ enzymatically cross-linked gelatin hydrogels", Int. J Artif Organs, 40(4):159-168. published online Mar. 18, 2017 (10 pages).
Almany, L. et al., "Biosynthetic hydrogel scaffolds made from fibrinogen and polyethylene glycol for 3D cell cultures", Biomaterials, 26:2467-2477, May 2005, available online Aug. 20, 2004 (11 pages).
Artzi, N. et al., "Characterization of Star Adhesive Sealants Based on PEG/Dextran Hydrogels", Macromol. Biosci., 9:754-765, 2009 (12 pages).

(Continued)

*Primary Examiner* — Michael P Cohen
(74) *Attorney, Agent, or Firm* — Wilmer Cutler Pickering Hale and Dorr LLP

(57) ABSTRACT

The invention provides methods and polymer compositions for treating ocular disorders, where the methods and compositions comprise polymer that can form a hydrogel in the eye of a subject. The hydrogel is formed by reaction of (i) a nucleo-functional polymer that is a biocompatible polymer, such as a thiolated hyaluronic acid polymer, containing a plurality of thio-functional groups —$R^1$—SH wherein $R^1$ is hydrolyzable and (ii) an electro-functional polymer that is a biocompatible polymer, such as a poly(ethylene glycol) polymer, containing at least one thiol-reactive group.

17 Claims, 11 Drawing Sheets

(56) References Cited

FOREIGN PATENT DOCUMENTS

| WO | WO-2008066787 |  | 6/2008 |
|----|---------------|------|---------|
| WO | WO-2009006780 |  | 1/2009 |
| WO | WO-2013086015 |  | 6/2013 |
| WO | WO-2013170195 | A1 | 11/2013 |
| WO | WO-2016049791 | A1 | 4/2016 |
| WO | WO-2016197005 | A1 | 12/2016 |
| WO | WO-2018/013819 | A1 | 1/2018 |
| WO | WO-2019/140184 | A1 | 7/2019 |
| WO | WO-2019/140212 | A1 | 7/2019 |
| WO | WO-2021000050 | A1 | 1/2021 |
| WO | WO-2022150497 | A1 | 7/2022 |
| WO | WO-2023097213 | A1 | 6/2023 |

OTHER PUBLICATIONS

Bai, X. et al., "Dual crosslinked chondroitin sulfate injectable hydrogel formed via continuous Diels-Alder (DA) click chemistry for bone repair", Carbohydrate Polymers, 166:123-130, available online Feb. 20, 2017 (8 pages).

Baino, F., "The Use of Polymers in the Treatment of Retinal Detachment: Current Trends and Future Perspectives", Polymers, 2:286-322, Sep. 9, 2010 (37 pages).

Bang, S. et al., "Injectable pullulan hydrogel for the prevention of postoperative tissue adhesion", International Journal of Biological Macromolecules, 87:155-162, Jun. 2016, published online Feb. 12, 2016 (8 pages).

Barth, H. et al., "A cross-linked hyaluronic acid hydrogel (Healaflow®) as a novel vitreous substitute", Graefes Arch Clin Exp Ophthalmol 254:697-703, published online Jan. 8, 2016 (7 pages).

Barth, H. et al., "A new model for in vitro testing of vitreous substitute candidates", Graefes Arch Clin Exp Ophthalmol 252:1581-1592, published online Jul. 25, 2014 (12 pages).

Bernkop-Schnurch, A., "Thiomers: A new generation of mucoadhesive polymers", Advanced Drug Delivery Reviews, 57:1569-1582, available online Sep. 19, 2005 (14 pages).

Bioworld, "Molecular tools and Laboratory Essentials: PBS 5X with Saponin", https://www.bio-world.com/elisa-buffer/pbs-5x-with-saponin-p-40120364, 2020 (2 pages).

Boyd, S. et al., Management of Complications in Ophthalmic Surgery, Boyd and Wu, Eds., Jaypee-Highlights Medical Publishers, Inc., Panama, pp. 85-87, 2009 (5 pages).

Chang, J. et al., "An in situ-forming zwitterionic hydrogel as vitreous substitute", J. Mater. Chem. B, 3:1097-1105 (2015), first published Dec. 4, 2014 (9 pages).

Chang, S. et al., "Giant Retinal Tears - Surgical Techniques and Results Using Perfluorocarbon Liquids", Arch Ophthalmology, 107:761-766, May 1989, accessed Jan. 8, 2019 (6 pages).

Chen, X. et al., "Chitosan-based thermosensitive hydrogel as a promising ocular drug delivery system: Preparation, characterization, and in vivo evaluation", Journal of Biomaterials Applications, 27(4):391-402, 2011 (12 pages).

Chien, H-W. et al., "An in situ poly(carboxybetaine) hydrogel for tissue engineering applications", Biomater. Sci., 5:322-330, published online Jan. 4, 2017 (9 pages).

Chien, Y. et al., "Corneal repair by human corneal keratocyte-reprogrammed iPSCs and amphiphatic carboxymethyl-hexanoyl chitosan hydrogel", Biomaterials, 33:8003-8016, available online Jul. 31, 2012 (14 pages).

Chirila, T.V. et al., "Synthetic Polymers as Materials for Artificial Vitreous Body: Review and Recent Advances", Journal of Biomaterials Applications, 9(2):121-137, Oct. 1994 (17 pages).

Chirila, T.V. et al., "The Use of Hydrophilic Polymers as Artificial Vitreous", Prog. Polym. Sci., 23:475-508, 1998 (34 pages).

Cho, E. et al., "Formulation and characterization of poloxamine-based hydrogels as tissue sealants", Acta Biomaterialia, 8(6):2223-2232, Mar. 8, 2012 (10 pages).

Cho, S-H. et al., "An injectable collagen/poly(γ-glutamic acid) hydrogel as a scaffold of stem cells and α-lipoic acid for enhanced protection against renal dysfunction", Biomater. Sci., 5:285-294, 2017, published online Dec. 15, 2016 (10 pages).

Coseal® Surgical Sealant, Instructions for Use, Baxter Healthcare Corporation, Hayward, California, http://www.coseal.com/us/pdf/COSEAL_IFU.pdf, dated Mar. 2009 (2 pages).

Crafoord, S. et al., "Experimental vitreous tamponade using polyalkylimide hydrogel", Graefes Arch Clin Exp. Ophthalmol, 249(8):1167-1174, published online Mar. 31, 2011 (8 pages).

D'souza, A. et al., "Polyethylene glycol (PEG): a versatile polymer for pharmaceutical applications", Expert Opinion on Drug Delivery, 13(9):1257-1275, Published online May 17, 2016 (20 pages).

Daniele, S. et al., "Glyceryl Methacrylate Hydrogel as a Vitreous Implant: An Experimental Study", Arch of Ophthal, 80(1):120-127, Jul. 1968, accessed Jan. 8, 2019 (7 pages).

Davidorf, F.H. et al., "Ocular Toxicity of Vitreal Pluronic Polyol F-127", Retina, 10(4):297-300, 1990 (4 pages).

De Jong, C. et al., "ADCON®-L Hydrogel as a Vitreous Substitute: Preliminary Results", Bulletin de la Société Belge Ophtalmologie, 278:71-75, 2000 (5 pages).

Deerenberg, E.B. et al., "Polyvinyl Alcohol Hydrogel Decreases Formation of Adhesions in a Rat Model of Peritonitis", Surgical Infections, 13(5):321-325, 2012 (5 pages).

Donati, S. et al., "Vitreous Substitutes: The Present and the Future", BioMed Research International, vol. 2014, Article 351804, pp. 1-12, May 4, 2014 (13 pages).

Dong, D. et al., "In Situ "Clickable" Zwitterionic Starch-Based Hydrogel for 3D Cell Encapsulation", ACS Applied Materials & Interfaces, 8:4442-4455, Jan. 28, 2016 (14 pages).

Dong, Y. et al., "Performance of an in situ formed bioactive hydrogel dressing from a PEG-based hyperbranched multifunctional copolymer", Acta Biomaterialia, 10:2076-2085, May 2014, available online Dec. 31, 2013 (10 pages).

Du, H. et al., "Injectable in situ Physically and Chemically Crosslinkable Gellan Hydrogel", Author Manuscript published in final edited form as Macromol Biosci., 12(7):952-961, Jul. 2012 (24 pages).

Duker, J., "Chapter 6.30: Macular Hole", Ophthalmology, Third Edition, Yanoff, et al., Eds., Mosby Elsevier, pp. 682-685, 2009 (6 pages).

DuraSeal Product Information, Integra LifeSciences Corporation, Plainsboro, New Jersey, www.integralife.com, dated Jun. 2014 (2 pages).

Emoto, S. et al., "Intraperitoneal administration of cisplatin via an in situ cross-linkable hyaluronic acid-based hydrogel for peritoneal dissemination of gastric cancer", Surg Today, 44(5):919-926, 2014, published online Jul. 26, 2013 (8 pages).

Engelbert, M. et al., "Chapter 6.6, Vitrectomy", Ophthalmology, Third Edition, Yanoff, et al., Eds., Mosby Elsevier, pp. 530-533, 2009 (6 pages).

European Extended Search Report issued in European Application No. 19738225.2, dated Sep. 23, 2021 (10 pages).

European Extended Search Report issued in European Application No. 24167099.1, dated Jul. 19, 2024 (11 pages).

European Supplemental Search Report issued in EP17828468.3 dated Feb. 18, 2020 (8 pages).

Falabella, C.A. et al., "Novel Macromolecular Crosslinking Hydrogel to Reduce Intra-Abdominal Adhesions", Journal of Surgical Research, 159(2):772-778, Apr. 2010 (7 pages).

Fathalla, Z. M.A. et al., "Poloxamer-based thermoresponsive ketorolac tromethamine in situ gel preparations: Design, characterisation, toxicity and transcorneal permeation studies", Eur J. Pharm Biopharm, 114:119-134, published online Jan. 24, 2017 (16 pages).

FDA, Medical Devices Databases, Product Classification, Device: Fluid, Intraocular, Mar. 31, 2016, Advisory Committee/Panel Meetings—CDRH, last updated Jan. 1, 2019 (2 pages).

Fernández-Ferreiro, A. et al., "In vitro and in vivo ocular safety and eye surface permanence determination by direct and Magnetic Resonance Imaging of ion-sensitive hydrogels based on gellan gum and kappa-carrageenan", Eur J. Pharm Biopharm, 94:342-351, published online Jun. 14, 2015 (10 pages).

Foster, W.J. et al., "Internal Osmotic Pressure as a Mechanism of Retinal Attachment in a Vitreous Substitute", Journal of Bioactive and Compatible Polymers, 21:221-235, May 1, 2006 (15 pages).

(56) References Cited

OTHER PUBLICATIONS

Gao, Y. et al., "PLGA-PEG-PLGA hydrogel for ocular drug delivery of dexamethasone acetate", Drug Dev Ind Pharm, 36(10):1131-1138, 2010 (9 pages).
Ghobril, C. et al., "A Dendritic Thioester Hydrogel Based on Thiol-Thioester Exchange as a Dissolvable Sealant System for Wound Closure", Angew. Chem. Int. Ed, 52:14070-14074, 2013 (5 pages).
Ghosh, S. et al., "Strong poly(ethylene oxide) based gel adhesives via oxime cross-linking", Acta Biomaterialia, 29:206-214, Jan. 1, 2016, published online Oct. 22, 2015 (9 pages).
Gupta, H. et al., "Physiologically active hydrogel (in situ gel) of sparfloxacin and its evaluation for ocular retention using gamma scintigraphy", J Pharm Bioallied Sci., 7(3):195-200, Jul.-Sep. 2015 (8 pages).
Hahn, et al., "Influence of hydrogel mechanical properties and mesh size on vocal fold fibroblast extracellular matrix production and phenotype," Author Manuscript published in final edited form as: Acta Biomater 4(5):1161-1171, Sep. 2008 (19 pages).
Hassan, W. et al., "Encapsulation and 3D culture of human adipose-derived stem cells in an in-situ crosslinked hybrid hydrogel composed of PEG-based hyperbranched copolymer and hyaluronic acid", Stem Cell Research & Therapy, 4:32, Mar. 21, 2013 (11 pages).
Hawkins, B.S. et al., "Chapter 94—Retina-Related Clinical Trials: A Resource Bibliography", Retina, vol. Two, Fifth Edition, pp. 1589-1613, 2013 (26 pages).
Healaflow, Product Information Brochure, Aptissen S.A., Geneva, Switzerland, accessed Jan. 29, 2019 (12 pages).
Hermann, C.D. et al., "Rapidly polymerizing injectable click hydrogel therapy to delay bone growth in a murine re-synostosis model", Biomaterials, 35(36):9698-9708, Dec. 2014, available online Aug. 28, 2014 (11 pages).
Hogen-Esch, T.E. et al., "Development of Injectable Poly(glyceryl Methacrylate) Hydrogels for Vitreous Prosthesis" Journal of Biomedical Materials Research, 10(6):975-976, 1976 (2 pages).
Hombrebueno, et al., "Intravitreal Injection of Normal Saline Induces Retinal Degeneration in the C57BL/6J Mouse," *Translational Vision Science & Technology*, 3(2):Article 3, Mar. 27, 2014 (10 pages).
Hong, J.H. et al., "Injectable Polypeptide Thermogel as a Tissue Engineering System for Hepatogenic Differentiation of Tonsil-Derived Mesenchymal Stem Cells", Applied Materials & Interfaces, 9:11568-11576, Mar. 14, 2017 (9 pages).
Hong, Y. et al., "Biodegradation in vitro and retention in the rabbit eye of crosslinked poly(1-vinyl-2-pyrrolidinone) hydrogel as a vitreous substitute", Journal of Biomedical Materials Research, 39(4):650-659, 1998 (10 pages).
Hoshi, S. et al., "In Vivo and In Vitro Feasibility Studies of Intraocular Use of Polyethylene Glycol-Based Synthetic Sealant to Close Retinal Breaks in Porcine and Rabbit Eyes", Investigative Ophthalmology & Visual Science, 56(8):4705-4711, Jul. 2015 (7 pages).
Hoshi, S. et al., "Polyethylene Glycol-Based Synthetic Hydrogel Sealant for Closing Vitrectomy Wounds: An In Vivo and Histological Study", Translational Vision Science & Technology, 5(3):Article 7, May 17, 2016 (8 pages).
Huang, W. et al., "Preparation, pharmacokinetics and pharmacodynamics of ophthalmic thermosensitive in situ hydrogel of betaxolol hydrochloride", Biomed Pharmaco, 83:107-113, Oct. 2016 (7 pages).
Huynh, C.T. et al., "Synthesis, Characteristics and Potential Application of Poly(β-Amino Ester Urethane)-Based Multiblock Co-Polymers as an Injectable, Biodegradable and pH/Temperature-Sensitive Hydrogel System", Journal of Biomaterials Science 23:1091-1106, 2012 (17 pages).
International Search Report and Written Opinion as issued by U.S. Patent and Trademark Office as International Search Authority, in International Application PCT/US19/13223, dated Apr. 12, 2019 (9 pages).
International Search Report and Written Opinion issued by the Australian Patent Office as International Searching Authority in International Application No. PCT/US17/41947 dated Aug. 21, 2017 (8 pages).
International Search Report and Written Opinion issued by the U.S. Patent and Trademark Office as International Searching Authority in International Application No. PCT/US22/80314 dated Mar. 22, 2023 (17 pages).
International Search Report and Written Opinion issued by the U.S. Patent and Trademark Office as International Searching Authority, in International Application No. PCT/US19/13185, dated Apr. 15, 2019 (9 pages).
International Search Report and Written Opinion issued by U.S. Patent and Trademark Office as International Searching Authority in International Application No. PCT/US22/11469, dated Mar. 22, 2022 (11 pages).
Ishiyama, N. et al., "The prevention of peritendinous adhesions by a phospholipid polymer hydrogel formed in situ by spontaneous intermolecular interactions", Biomaterials, 31(14):4009-4016, May 2010, published online Feb. 10, 2010 (8 pages).
Kang, W. et al., "Photocrosslinked methacrylated carboxymethyl chitin hydrogels with tunable degradation and mechanical behavior", Carbohydrate Polymers, 160:18-25, 2017, published online Dec. 19, 2016 (8 pages).
Katagiri, Y. et al., "Application of Thermo-setting Gel as Artificial Vitreous", Japanese Journal of Ophthalmology, 49(6):491-496, 2005 (6 pages).
Kim, B.Y. et al., "Dual Enzyme—Triggered In Situ Crosslinkable Gelatin Hydrogels for Artificial Cellular Microenvironments", Macromolecular Bioscience, 16(11):1570-1576, 2016 (7 pages).
Kim, K.D. et al., "Polyethylene Glycol Hydrogel Spinal Sealant (DuraSeal Spinal Sealant) as an Adjunct to Sutured Dural Repair in the Spine: Results of a Prospective, Multicenter, Randomized Controlled Study", Spine, 36(23):1906-1912, Nov. 1, 2011 (7 pages).
Kleinberg, T.T. et al., "Vitreous Substitutes: A Comprehensive Review", Survey of Ophthalmology, 56(4):300-323, Jul.-Aug. 2011 (24 pages).
Kumar, D. et al., "Three-dimensional hypoxic culture of human mesenchymal stem cells encapsulated in a photocurable, biodegradable polymer hydrogel: A potential injectable cellular product for nucleus pulposus regeneration", Acta Biomaterialia, 10:3463-3474, published online May 2, 2014 (12 pages).
Kwon, J.W. et al., "Biocompatibility of poloxamer hydrogel as an injectable intraocular lens: A pilot study", J Cataract Refract Surg, 31:607-613, Mar. 2005 (7 pages).
Lee, H. et al., "Fast in situ enzymatic gelation of PPO-PEO block copolymer for injectable intraocular lens in vivo", J Biomater Appl, 28(8):1247-1263, 2014 (17 pages).
Li, C. et al., "Enhancement in bioavailability of ketorolac tromethamine via intranasal in situ hydrogel based on poloxamer 407 and carrageenan", Int J Pharm, 474(1-2):123-133, published online Aug. 17, 2014 (11 pages).
Li, X. et al., "Engineering In Situ Cross-Linkable and Neurocompatible Hydrogels", J Neurotrauma, 31:1431-1438, Aug. 15, 2014 (8 pages).
Li, L. et al., "Biodegradable and injectable in situ cross-linking chitosan-hyaluronic acid based hydrogels for postoperative adhesion prevention", Biomaterials, 35(12):3903-3917, available online Feb. 4, 2014 (15 pages).
Li, L. et al., "Injectable and Biodegradable pH-Responsive Hydrogels for Localized and Sustained Treatment of Human Fibrosarcoma", Applied Materials & Interfaces, 7:8033-8040, Apr. 2, 2015 (8 pages).
Li, Q. et al., "Biodegradable and photocrosslinkable polyphosphoester hydrogel", Biomaterials, 27:1027-1034, Mar. 2006, available online Aug. 24, 2005 (8 pages).
Li, S. et al., "Injectable PAMAM/ODex double-crosslinked hydrogels with high mechanical strength", Biomed. Mater, 12:015012, 2017, published online Dec. 9, 2016 (12 pages).

(56) References Cited

OTHER PUBLICATIONS

Li, X. et al., "A covalently crosslinked polysaccharide hydrogel for potential applications in drug delivery and tissue engineering", J Mater Sci: Mater Med, 23:2857-2865, published online Oct. 4, 2012 (9 pages).

Li, X. et al., "In situ gel-forming AP-57 peptide delivery system for cutaneous wound healing", Int J Pharm, 495(1):560-571, available online Sep. 9, 2015 (12 pages).

Liang, Y. et al., "An in situ formed biodegradable hydrogel for reconstruction of the corneal endothelium", Colloids and Surfaces B: Biointerfaces, 82(1):1-7, 2011, available online Jul. 30, 2010 (7 pages).

Lin, C-Y. et al., "In situ forming hydrogel composed of hyaluronate and polygalacturonic acid for prevention of peridural fibrosis", J Mater Sci: Mater Med, 26:168, published online Mar. 20, 2015 (12 pages).

Linh, N.T.B. et al., "Enzymatic in situ formed hydrogel from gelatin-tyramine and chitosan-4-hydroxylphenyl acetamide for the co-delivery of human adipose-derived stem cells and platelet-derived growth factor towards vascularization", Biomedical Materials, 12:015026, Feb. 24, 2017 (12 pages).

Liu, H et al., "Thermosensitive injectable in-situ forming carboxymethyl chitin hydrogel for three-dimensional cell culture", Acta Biomaterialia, 35:228-237, published online Feb. 18, 2016 (10 pages).

Luo, Z et al., "Thermosensitive PEG-PCL-PEG (PECE) hydrogel as an in situ gelling system for ocular drug delivery of diclofenac sodium", Drug Delivery, 23(1):63-68, 2016, published online Apr. 24, 2014 (7 pages).

Lutolf, M.P. et al., "Synthetic matrix metalloproteinase-sensitive hydrogels for the conduction of tissue regeneration: Engineering cell-invasion characteristics," PNAS, 100(9):5413-5418, Apr. 29, 2003 (6 pages).

Lv, Z. et al., "Thermosensitive in situ hydrogel based on the hybrid of hyaluronic acid and modified PCL/PEG triblock copolymer", Carbohydrate Polymers, 108:26-33, published online Mar. 21, 2014 (8 pages).

Mah, F.S. "Effect on Gel Formation Time of Adding Topical Ophthalmic Medications to ReSure Sealant, an In Situ Hydrogel", J Ocul Pharmacol Ther, 32(6):396-399, 2016 (5 pages).

Mamor, M., "Retinal detachment from hyperosmotic intravitreal injection", Investigative Ophthalmology & Visual Science, vol. 18, No. 12, pp. 1237-1244, Dec. 1979 (8 pages).

Marticorena, J. et al., "Sterile Endophthalmitis after Intravitreal Injections," Mediators of Inflammation, vol. 2012, Article ID 928123, 2012 (6 pages).

Maruoka, S. et al., "Biocompatibility of Polyvinylalcohol Gel as a Vitreous Substitute", Current Eye Research, 31(7-8):599-606, 2006 (9 pages).

Masket, S. et al., "Hydrogel sealant versus sutures to prevent fluid egress after cataract surgery", J Cataract Refract Surg, 40:2057-2066, 2014 (10 pages).

Mazza, E. et al., "Mechanical biocompatibility of highly deformable biomedical materials", J Mech Behav Biomed Mater, 48:100-124, available online Apr. 1, 2015 (25 pages).

McKay, C.A. et al., "An Injectable, Calcium Responsive Composite Hydrogel for the Treatment of Acute Spinal Cord Injury", ACS Applied Materials & Interfaces, 6(3):1424-1438, Jan. 3, 2014 (15 pages).

Migliavacca, L. et al., "Experimental short-term tolerance to perfluorodecalin in the rabbit eye: a histopathologic study", Current Eye Research, 17(8):828-835, 1998 (9 pages).

Miki, D. et al., "A Photopolymerized Sealant for Corneal Lacerations", Cornea, 21(4):393-399, May 2002 (7 pages).

Miles, D.E. et al., "*Peptide: glycosaminoglycan hybrid hydrogels as an injectable intervention for spinal disc degeneration*", J Materials Chemistry B, Materials for Biology and Medicine, 4(19):3225-3231, May 11, 2016 (8 pages).

Morelli, A. et al., "Design, preparation and characterization of ulvan based thermosensitive hydrogels", Carbohydrate Polymers, 136:1108-1117, 2016, available online Oct. 13, 2015 (10 pages).

Na, S.Y. et al., "Hyaluronic acid/mildly crosslinked alginate hydrogel as an injectable tissue adhesion barrier", J Mater Sci: Mater Med, 23:2303-2313, published online Jun. 3, 2012 (11 pages).

Naderi-Meshkin, H. et al., "Chitosan-based injectable hydrogel as a promising in situ forming scaffold for cartilage tissue engineering", Cell Biol Int, 38(1):72-84, Jan. 2014, published online Oct. 15, 2013 (14 pages).

Nam, K. et al., "Modeling of swelling and drug release behavior of spontaneously forming hydrogels composed of phospholipid polymers", Int J. Pharm, 275(1-2):259-269, May 2004 (11 pages).

Nam, K. et al., "pH-modulated release of insulin entrapped in a spontaneously formed hydrogel system composed of two water-soluble phospholipid polymers", J Biomater. Sci. Polymer Edn, 13(11):1259-1269, 2002 (12 pages).

Nie, W. et al., "Rapidly in situ forming chitosan/E-polylysine hydrogels for adhesive sealants and hemostatic materials", Carbohydrate Polymers, 96:342-348, available online Apr. 15, 2013 (7 pages).

Ossipov, D.A. et al., "Poly(vinyl alcohol) Cross-Linkers for in Vivo Injectable Hydrogels", Macromolecules, 41(11):3971-3982, 2008 (12 pages).

Parel, J-M. et al., "Chapter 129: Silicone Oils: Physicochemical Properties", Retina: vol. I, Fourth Edition, Ryan, Editor, Mosby Elsevier, pp. 2191-2210, 2006 (22 pages).

Patel, S.P. et al., "Novel Thermosensitive Pentablock Copolymers for Sustained Delivery of Proteins in the Treatment of Posterior Segment Diseases", Author Manuscript published in final edited form as Protein Pept Lett, 21(11):1185-1200, 2014 (34 pages).

Peyman, G.A. et al., "Diagnostic and Surgical Techniques: Perfluorocarbon Liquids in Ophthalmology", Kramer, et al., eds., Survey of Ophthalmology, 39(5):375-395, Mar.-Apr. 1995 (21 pages).

Quinteros, D.A. et al., "Evaluation of the Performance of an Ophthalmic Thermosensitive Hydrogel Containing Combination of Suramin and Bevacizumab", Current Pharmaceutical Design, 22:1-9, 2016 (9 pages).

Ramakumar, S. et al., "Local Hemostasis during Laparoscopic Partial Nephrectomy Using Biodegradable Hydrogels: Initial Porcine Results", Journal of Endourology, 16(7):489-494, Sep. 2002 (6 pages).

Ren, X.J. et al., "Patching Retinal Breaks with Healaflow in 27-Gauge Vitrectomy for the Treatment of Rhegmatogenous Retinal Detachment", Retina, The Journal of Retinal and Vitreous Diseases, 40(10):1900-1908, 2020 (9 pages).

ReSure® Sealant Product Information, Instructions for Use, Ocular Therapeutix, Bedford, Massachusetts, https://www.resuresealant.com/wp-content/uploads/2017/05/LCN-80-1004-011-Rev-C-ReSure-Sealant-Instructions-for-Use.pdf, accessed Jan. 29, 2019 (2 pages).

Sakai, S. et al., "Peritoneal adhesion prevention by a biodegradable hyaluronic acid-based hydrogel formed in situ through a cascade enzyme reaction initiated by contact with body fluid on tissue surfaces", Acta Biomaterialia, 24:152-158, published online Jun. 20, 2015 (7 pages).

Sanders, L. et al., "Mechanical Characterization of a Bi-functional Tetronic Hydrogel Adhesive for Soft Tissues", Author Manuscript published in final edited form as J Biomed Mater Res A., 103(3):861-868, Mar. 2015 (19 pages).

Santhanam, S. et al., "Biomimetic hydrogel with tunable mechanical properties for vitreous substitutes", Acta Biomaterialia, 43:327-337, published online Jul. 29, 2016 (11 pages).

Shazly, T.M. et al., "Augmentation of postswelling surgical sealant potential of adhesive hydrogels", Journal of Biomedical Materials Research A, 95A(4):1159-1169, published online Sep. 28, 2010 (11 pages).

Shu, X.Z. et al., "Disulfide Cross-Linked Hyaluronan Hydrogels", Biomacromolecules, 3:1304-1311, 2002 (8 pages).

Sinapis, C.I. et al., "Pharmacokinetics of intravitreal bevacizumab (Avastin®) in rabbits", Clinical Ophthalmology, 5:697-704, May 23, 2011 (8 pages).

Steffensen, S.L. et al., "Soft hydrogels interpenetrating silicone—A polymer network for drug-releasing medical devices", J Biomed Mater Res Part B, 104B(2):402-410, Feb. 2016, published online Apr. 17, 2015 (9 pages).

(56) References Cited

OTHER PUBLICATIONS

Suchaoin, W. et al., "Mucoadhesive polymers: Synthesis and in vitro characterization of thiolated poly(vinyl alcohol)," International Journal of Pharmaceutics, 503(1):141-149, available online Mar. 7, 2016, DOI: 10.1016/j.ijpharm.2016.03.006 (9 total pages).
Supplementary European Search Report and Search Opinion, for EP Application No. 19738225.2, dated Sep. 23, 2021, (10 pages).
Svirkin, Y. et al., "Biodegradable thiol-modified poly(vinyl alcohol) hydrogels", Materials Research Society, MRS 2013, Cambridge Polymer Group, Presentation 7-17, Oct. 1, 2010 (14 pages).
Swindle, K. et al., "Recent advances in polymeric vitreous substitutes", Expert Review of Ophthalmology, 2(2):255-265, 2007 (11 pages).
Swindle-Reilly, K.E. et al., "Chapter 13: Designing hydrogels as vitreous substitutes in ophthalmic surgery", Biomaterials and Regenerative Medicine in Ophthalmology, Traian Chirila, Ed., Woodhead Publishing, Sawston, Cambridge, Great Britain, pp. 339-373, 2010 (36 pages).
Swindle-Reilly, K.E. et al., "Rabbit Study of an In Situ Forming Hydrogel Vitreous Substitute", Investigative Ophthalmology & Visual Science, 50(10):4840-4846, Oct. 2009 (7 pages).
Taich, P. et al., "Sustained-release hydrogels of topotecan for retinoblastoma", Colloids and Surfaces B: Biointerfaces, 146:624-631, published online Jul. 2, 2016 (8 pages).
Takahashi, A. et al., "In Situ Cross-Linkable Hydrogel of Hyaluronan Produced via Copper-Free Click Chemistry", Biomacromolecules, 14:3581-3588, Sep. 4, 2013 (8 pages).
Tan, J. et al., "Improved cell adhesion and proliferation on synthetic phosphonic acid-containing hydrogels", Biomaterials, 26:3663-3671, Jun. 2005 (9 pages).
Tao, Y. et al., "Evaluation of an in situ chemically crosslinked hydrogel as a long-term vitreous substitute material", Acta Biomaterialia, 9:5022-5030, Feb. 2013, available online Sep. 27, 2012 (9 pages).
Teruya, K., et al., "Patching retinal breaks with Seprafilm® in experimental rhegmatogenous retinal detachment of rabbit eyes", Eye, 23:2256-2259, published online Jan. 23, 2009 (4 pages).
Thakral, S., et al., "Stabilizers and their interaction with formulation components in frozen and freeze-dried protein formulations", Advanced Drug Delivery Reviews, 173:1-19, published online Mar. 17, 2021 (19 pages).
Tortora, M. et al., "Michael-Type Addition Reactions for the In Situ Formation of Poly(vinyl alcohol)-Based Hydrogels", Biomacromolecules, 8(1):209-214, 2007 (6 pages).
Transparency Market Research, "Vitreous Tamponades Market: (By Types: Gases, Silicone Oil and Perfluorocarbons)—Global Industry Analysis, Size, Growth, Trends and Forecast, 2014-2020", 2015 (73 pages).
Vaziri, K. et al., "Tamponade in the surgical management of retinal detachment", Clinical Ophthalmology, 10:471-476, 2016 (6 pages).
Vijayasekaran, S. et al., "Poly(1-Vinyl-2-Pyrrolidinone) hydrogels as vitreous substitutes: Histopathological evaluation in the animal eye", Journal of Biomaterials Science, Polymer Edition, 7(8):685-696, 1996 (13 pages).
Villa-Camacho, J.C. et al., "The efficacy of a lysine-based dendritic hydrogel does not differ from those of commercially available tissue sealants and adhesives: an ex vivo study", BMC Musculoskeletal Disorders, 16:116, May 2015 (6 pages).
Vulpe, R. et al., "Rheological study of in-situ crosslinkable hydrogels based on hyaluronanic acid, collagen and sericin", Materials Science and Engineering C, 69:388-397, published online Jul. 5, 2016 (10 pages).
Wallace, D.G. et al., "A Tissue Sealant Based on Reactive Multifunctional Polyethylene Glycol", J Biomed Mater Res (Appl Biomater), 58(5):545-555, 2001 (11 pages).
Wang, F. et al., "Acute Intraocular Inflammation Caused by Endotoxin after Intravitreal Injection of Counterfeit Bevacizumab in Shanghai, China," Ophthalmology 120(2):355-361, Feb. 2013 (7 pages).
Wang, J. et al., "In Situ-Forming Polyamidoamine Dendrimer Hydrogels with Tunable Properties Prepared via Aza-Michael Addition Reaction", Applied Materials & Interfaces, 9:10494-10503, Mar. 6, 2017 (10 pages).
Wang, R. et al., "Fast in situ generated &-polylysine-poly (ethylene glycol) hydrogels as tissue adhesives and hemostatic materials using an enzyme-catalyzed method", Journal of Biomaterials Applications, 29(8):1167-1179, 2015 (13 pages).
Wang, T. et al., "Preparation and properties of a novel thermosensitive hydrogel based on chitosan/hydroxypropyl methylcellulose/glycerol", International Journal of Biological Macromolecules, 93:775-782, published online Sep. 14, 2016 (8 pages).
Wathier, M. et al., "Dendritic Macromers as in Situ Polymerizing Biomaterials for Securing Cataract Incisions", Journal of American Chemical Society, 126(40):12744-12745, published online Sep. 21, 2004 (9 pages).
Wei, C.-Z. et al., "A thermosensitive chitosan-based hydrogel barrier for post-operative adhesions' prevention", Biomaterials, 30:5534-5540, published online Aug. 3, 2009 (7 pages).
Weng, L. et al., "An in situ forming biodegradable hydrogel-based embolic agent for interventional therapies", Acta Biomaterialia, 9:8182-8191, published online Jun. 19, 2013 (10 pages).
Wu, H. et al., "Novel self-assembled tacrolimus nanoparticles cross-linking thermosensitive hydrogels for local rheumatoid arthritis therapy", Colloids and Surfaces B: Biointerfaces, 149:97-104, published online Oct. 6, 2016 (8 pages).
Xia, et al., DaCihai, General knowledge evidence 1, Materials Science, Shanghai Lexicographical Publishing House, vol. 37:499, Dec. 31, 2015 (5 pages)—with English Translation.
Xiao, J. et al., "Synthesis of Polymerizable Protein Monomers for Protein-Acrylamide Hydrogel Formation", Biomacromolecules, 10(7):1939-1946, 2009 (8 pages).
Xu, Y. et al., "Spontaneous Packaging and Hypothermic Storage of Mammalian Cells with a Cell-Membrane-Mimetic Polymer Hydrogel in a Microchip", Applied Materials & Interfaces, 7:23089-23097, Oct. 5, 2015 (9 pages).
Xu, Y. et al., "Synthesis, characterization, biodegradability and biocompatibility of a temperature-sensitive PBLA-PEG-PBLA hydrogel as protein delivery system with low critical gelation concentration", Drug Development and Industrial Pharmacy, 40(9):1264-1275, 2014, published online Jul. 15, 2013 (13 pages).
Yin, H. et al., "Toxicity Evaluation of Biodegradable and Thermosensitive PEG-PCL-PEG Hydrogel as a Potential In Situ Sustained Ophthalmic Drug Delivery System", J Biomed Mater Res B: Appl Biomater, 92B(1):129-137, 2010, published online Oct. 2, 2009 (9 pages).
Yu, J. et al., "In situ covalently cross-linked PEG hydrogel for ocular drug delivery applications", International Journal of Pharmaceutics, 470(1-2):151-157, available online Apr. 23, 2014 (7 pages).
Yu, Y. et al., "Injectable Chemically Crosslinked Hydrogel for the Controlled Release of Bevacizumab in Vitreous: A 6-Month In Vivo Study", http://tvstjournal.org/doi/full/10.1167/tvst.4.2.5, TVST, 4(2):Article 5, Mar. 2015 (11 pages).
Zarembinski, T.I. et al., "Thiolated hyaluronan-based hydrogels crosslinked using oxidized glutathione: An injectable matrix designed for ophthalmic applications", Acta Biomaterialia, 10:94-103, 2014, published online Oct. 1, 2013 (10 pages).
Zawaneh, P.N. et al., "Design of an injectable synthetic and biodegradable surgical biomaterial", PNAS, 107(24):11014-11019, Jun. 15, 2010 (6 pages).
Zhao, X. et al., "Photocrosslinkable Gelatin Hydrogel for Epidermal Tissue Engineering", Advanced Healthcare Materials, 5:108-118, 2016 (11 pages).
Zhou, Y. et al., "Rapid Gelling Chitosan/Polylysine Hydrogel with Enhanced Bulk Cohesive and Interfacial Adhesive Force: Mimicking Features of Epineurial Matrix for Peripheral Nerve Anastomosis", Biomacromolecules, 17(2):622-630, Jan. 18, 2016 (9 pages).
International Search Report and Written Opinion issued by U.S. Patent and Trademark Office as International Searching Authority in

(56) References Cited

OTHER PUBLICATIONS

International Application No. PCT/US24/39416, dated Nov. 22, 2024 (11 pages).

* cited by examiner

Thiolated Hyaluronic Acid

PEG Diacrylate

Crosslinking ‑ ‑ ‑ ‑ ‑ TO FIG. 5B

Thiolated Hyaluronic Acid tHA derivative by hydrolytic degradation

Hydrazine        Acetic acid

Hyaluronic acid

Polyethylene glycol 3-(2-carboxyethylthio)propionic acid

β-D-glucuronic acid (GlcA)

N-acetyl-β-D-glucosamine (GlcNAc)

HYDROGEL FORMULATIONS AND METHODS AND DEVICES FOR ADMINISTRATION OF THE SAME

FIELD OF THE INVENTION

The invention is directed to formulations comprising polymers and polymer compositions that form hydrogels for the treatment of ocular disorders. The invention is also directed to formulations comprising polymers and polymer compositions that form hydrogels, including extended-release hydrogels, comprising a pharmaceutically active agent (e.g., a drug) and methods of using the hydrogels comprising a pharmaceutically active agent for providing targeted release of the pharmaceutically active agent to a site of interest for focal treatment within the eye of a subject for a variety of disorders. The invention is also directed to medical devices and methods for focal delivery of the hydrogel-forming polymer formulations and compositions comprising application to a targeted site of interest within the eye of a subject.

BACKGROUND

Despite advances in vitreoretinal surgical techniques over the last 40 years, the methods available for retinal tamponade have changed very little. Limitations associated with current methods of tamponade (i.e. post-operative gas or silicone oil), including the burden of face down positioning, limited effectiveness in the inferior retina, poor post-operative vision, cataract progression, flying/travel restrictions and other limitations.

Many attempts have been made to abrogate these limitations, but no viable replacement has yet emerged. If one could develop a method of successfully performing retinal surgery for retinal detachments without requiring gas or oil tamponade, the patient's post-operative experience would be radically improved. As such, there remains a large unmet need for a safe, easily injectable, and biodegradable polymer that would seal the retinal surface and eliminate the post-operative burden currently imposed on patients by gas and oil.

Pykus Therapeutics has for several years been investigating multiple hydrogel formulations to identify a viable lead formulation for advancement to late-stage clinical development.

A subject of the present disclosure is a formulation we have named PYK-2101, which is a second-generation formulation of a prior generation hydrogel product, both of which form by Michael's addition reaction between a nucleophile and an electrophile. Previous generation hydrogel products and methods of using the same are described in U.S. Pat. No. 11,883,378 B2; 11,547,779 B2; 11,077,232 B2; 10,973,955 B2; 10,973,954 B2; 10,874,767 B2, each of which is incorporated by reference in its entirety herein. An exemplary prior generation hydrogel product is referred to herein as PYK-1107, which comprises thiolated poly(vinyl) alcohol and polyethylene glycol diacrylate (PEGDA). In contrast, PYK-2101, an exemplary hydrogel product of the present disclosure, comprises thiolated hyaluronic acid (tHA) and polyethylene glycol diacrylate (PEGDA), and in certain embodiments may be formulated as an ~3% hydrogel. PYK-1107, which is also formulated as a ~3% hydrogel, was used in a pilot clinical trial of patients with retinal detachment (PYK-1107-RD003).

In the previously conducted clinical study using PYK-1107 (PYK-1107-RD003), a total of 3 patients with rhegmatogenous retinal detachment were enrolled. In all 3 patients, no significant post-operative inflammation (anterior chamber cell/flare or vitreous cell/flare) was observed. Given the absence of intraocular gas, all patients reported better-than-anticipated vision within days following surgery and no special post-operative positioning/bedrest was required. However, unexpectedly, all patients treated with PYK-1107 experienced acute elevation of intraocular pressure (IOP) at the time of product breakdown at approximately post-operative week 4. The consistent incidence of elevated IOP was determined to be a barrier for future clinical development of PYK-1107. The IOP development was peculiar, as it was not related to volume (as little as 10 microliters of investigational product could trigger elevation) nor the molecular weight of the degraded components, which were less than 100 kDa.

Given, however, the preliminary demonstration of efficacy in human eyes with retinal detachment, development of a formulation change was undertaken to improve the IOP tolerance of the product while maintaining the other desired performance characteristics. This led to the development and use of a tHA-containing formulation, as described herein. Despite its larger initial molecular weight compared to PYK-1107, PYK-2101 unexpectedly demonstrates significantly improved ocular biocompatibility and reduced risk of IOP elevation, as it breaks down by enzymatic degradation of the hyaluronic acid as well as, to a lesser extent, hydrolysis of the crosslink between the hyaluronic acid and the polyethylene glycol. Additionally, the presence of hyaluronic acid, which is a polysaccharide that is naturally present in the vitreous cavity, in the formulation described herein lowers the risk of immune-mediated trabeculitis mechanisms that may elevate intraocular pressure.

The greatest challenge for the development of a polymer composition that can act as a tamponade/retinal sealant has been identifying a substrate that is well tolerated in the eye both before and after degradation. Such a polymer composition, and any resulting hydrogels formed from it, offers opportunities for safe and effective delivery of certain pharmaceutical agents to the vitreous cavity as well.

Delivering a pharmaceutically active agent (e.g., a drug) to the body, including the vitreous cavity, in a safe and effective manner is desirable yet challenging. Such delivery may also be in an extended-release fashion, which provides many benefits to the subject, including more specific delivery, less off-site side-effects, more consistent and targeted control of drug dose over time, decreased frequency of drug administration, and better subject compliance. Importantly, a formulation for forming an extended-release hydrogel that can be injected through a cannula or needle, in particular a cannula or needle with a smaller diameter, could be directed into a wide variety of anatomical spaces, which would be clinically advantageous. For example, formulations for forming an extended-release hydrogel comprising a pharmaceutically active agent could be administered nearly anywhere in the body in a variety of ways, including but not limited to, topical, epidermal, subdermal, intra-adipose, intramuscular, intra-peritoneal, intravenous, intra-arterial, intracranial, intranasal, and/or intrauterine. In addition, targeted therapy through injection of a formulation that forms an extended-release hydrogel comprising a pharmaceutically active agent into an organ directly, the wall of an organ, or into the surrounding fascia or connective tissue of an organ would be desirable and beneficial.

Targeted extended release of a pharmaceutically active agent is particularly compelling when the target tissue is difficult to access clinically, a sensitive area, and/or where repeat access is invasive or burdensome to the subject. One compelling example is the eye. The structure of the mammalian eye is divided into two segments: the anterior and posterior. The anterior segment or anterior cavity is the front third of the eye and includes the cornea, iris, ciliary body, and lens. The posterior segment or posterior cavity is the back two-thirds of the eye and includes the choroid, retina, optic nerve, and vitreous humor. There are a number of disease conditions that affect the back of the eye and impact vision, including age-related macular degeneration (AMD), proliferative diabetic retinopathy, proliferative vitreoretinopathy, ocular malignancies, inherited retinal diseases, diabetic macular edema, macular edema from retinal vein occlusions, choroidal neovascularization, uveitis, amongst others.

Typical routes for administration of pharmaceutically active agents (e.g., drugs) to the eye include topical, systemic, subcutaneous, intravitreal, subretinal, intraocular, intracameral, suprachoroidal, subconjunctival, subtenon, intracanalicular, periobulbar and retrobulbar.

Effective delivery of pharmaceutically active agents for treatment of back-of-the-eye diseases remains a challenge. Delivery to the posterior segment of the eye is typically achieved via an intravitreal injection, the periocular route, implant, or by systemic administration. However, physiologic barriers to transport of the pharmaceutically active agents to the posterior segment from routes other than intravitreal injection often make their use impractical.

Intravitreal injection is often carried out with a 30 gauge or similar needle. While intravitreal injections offer high concentrations of pharmaceutically active agent to the vitreous chamber and retina, they can be associated with various short-term complications such as retinal detachment, inflammation, elevated intraocular pressure, endophthalmitis and intravitreal hemorrhage. Injection of small particles within the vitreous may lead to wide dispersal of the particles which can obstruct vision (experienced by the patient as "floaters"). Additionally, many current formulations for administration of a pharmaceutically active agent to the eye often require frequent repeat injections (e.g., monthly), thus increasing the risk of complications and resulting in a substantial burden on both the patient and the healthcare system in general.

In addition to the need for a safe and effective retinal tamponade/retinal sealant, a profound need exists for targeted extended-release pharmaceutically active agent delivery formulations, in particular, formulations that can be injected into sensitive/delicate tissues, including the eye. Formulations that provide for in-situ formation of hydrogels that provide extended-release of pharmaceutically active agents within the body can provide for longer-lasting drug delivery, minimize the risks of repeated administrations, such as injections, deliver more consistent and targeted doses, limit side effects, and decrease the substantial burden placed on the patient by repeat drug administration.

SUMMARY OF THE INVENTION

Polymer formulations for treating ocular disorders, wherein the polymer formulations form a hydrogel in the eye of a subject, are provided. The hydrogel is formed by reaction of (a) a nucleo-functional polymer containing a plurality of thio-functional groups —$R^1$—SH and (b) an electro-functional polymer that is a biocompatible polymer containing at least one thiol-reactive group. In certain embodiments, the nucleo-functional polymer is a naturally occurring polymer capable of enzymatic degradation. In other embodiments the nucleo-functional polymer contains a thio-functional group, —$R^1$—SH, wherein $R^1$ is hydrolyzable. In certain embodiments, formulations are provided comprising a nucleo-functional polymer, an electro-functional polymer and a pharmaceutically active agent in a pharmaceutically acceptable carrier. In some embodiments, formulations are provided comprising a nucleo-functional polymer and a pharmaceutically active agent in a pharmaceutically acceptable carrier. In certain embodiments, formulations are provided comprising an electro-functional polymer and a pharmaceutically active agent in a pharmaceutically acceptable carrier.

In some embodiments, formulations are provided that form an extended-release hydrogel to allow for safe and effective release of pharmaceutically active agents from the hydrogel over time. During degradation of such an extended-release hydrogel, the pharmaceutically active agent diffuses out of the hydrogel and into the local environment over a period of time, i.e., extended-release, that provides for therapeutically effective longer-term therapy than what would be achieved by injection of the pharmaceutically active agent alone. In certain embodiments the pharmaceutically active agent may be dissolved in the extended-release hydrogel-forming formulation, suspended within the extended-release hydrogel-forming formulation and/or encapsulated within a particle and dispersed within the extended-release hydrogel-forming formulation. In certain embodiments, features of the extended-release hydrogel-forming formulation and/or extended-release hydrogel include: materials that are non-toxic, varying crosslink density or porosity, varying reaction kinetics and varying biodegradation rate, all of which are appropriate to the desired method of administration, the desired target site in the subject, and the timeframe desired for the extended-release of the pharmaceutical into the environment surrounding the target site.

The following embodiments recite non-limiting permutations of combinations of features of the inventions described. Other permutations of combinations of features are also contemplated and/or described throughout the disclosure. In particular, each of these numbered embodiments is contemplated as depending from or relating to every previous or subsequent numbered embodiment, independent of the listed order.

E1. A method of contacting retinal tissue in an eye of a subject, the method comprising: injecting into the vitreous cavity of the eye of the subject an effective amount of a nucleo-functional polymer and an electro-functional polymer; and allowing the nucleo-functional polymer and the electro-functional polymer to react to form a hydrogel in the vitreous cavity, which hydrogel contacts the retinal tissue in the eye, thereby providing a retinal tamponade; wherein the nucleo-functional polymer is a biocompatible polymer comprising hyaluronic acid containing a plurality of thio-functional groups —$R^1$—SH, wherein $R^1$ is hydrolyzable, and the electro-functional polymer is a biocompatible polymer comprising poly(ethylene glycol) containing at least one thiol-reactive group.

E2. The method of embodiment E1, wherein —$R^1$—SH is

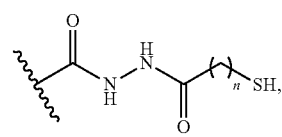

and n=1-3 or n=2.

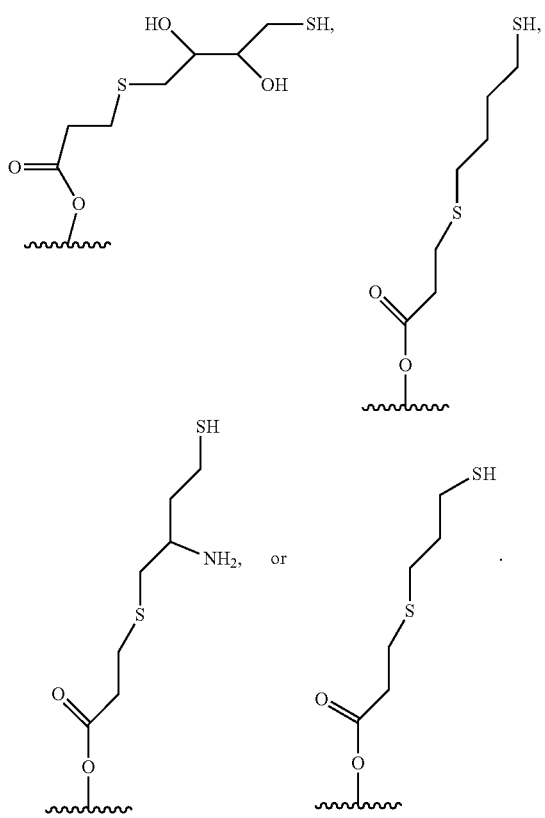

E3. The method of embodiment E1, wherein —R¹—SH is

E4. The method of any one of embodiments E1-E3, wherein up to about 200 µL of the nucleo-functional polymer, the electro-functional polymer, or a combination thereof is administered. E5. The method of any one of embodiments E1-E4, wherein the nucleo-functional polymer and the electro-functional polymer are focally applied in the vitreous cavity. E6. The method of any one of embodiments E1-E5, wherein the subject is having undergone a vitrectomy for repair of a retinal detachment or macular hole. E7. The method of any one of embodiments E1-E6, wherein the subject has a physical discontinuity in the retinal tissue, a tear in the retinal tissue, a break in the retinal tissue, or a hole in the retinal tissue. E8. The method of any one of embodiments E1-E7, wherein the nucleo-functional polymer and the electro-functional polymer are injected separately as liquid aqueous pharmaceutical compositions or together as a single, liquid aqueous pharmaceutical composition to the vitreous cavity of the eye of the subject. E9. The method of embodiment E8, wherein the separate liquid aqueous pharmaceutical compositions or single liquid aqueous pharmaceutical composition has a pH in the range of about 6.9 to about 7.2 or about 6.8 to about 7.6. E10. The method of any one of embodiments E1-E9, wherein the hydrogel has a transparency of at least 95% for light in the visible spectrum when measured through the hydrogel having a thickness of 1 cm. E11. The method of any one of embodiments E1-E10, wherein the hydrogel has a gelation time of less than about 10 minutes. E12. The method of any one of embodiments E1-E11, wherein the hydrogel undergoes complete biodegradation from the eye of the subject within about 3 days to about 7 days, about 2 weeks to about 8 weeks, or about 4 months to about 6 months, or within 12 months or 24 months. E13. The method of any one of embodiments E1-E12, wherein the hydrogel has a biodegradation half-life in the range of from about 1 week to about 3 weeks or from about 8 weeks to about 15 weeks when disposed within the vitreous cavity of an eye. E14. The method of any one of embodiments E1-E13, wherein the hydrogel generates a pressure within the eye of less than 25 mmHg. E15. The method of any one of embodiments E1-E14, wherein the nucleo-functional polymer has a weight-average molecular weight in the range of from about 75 kDa to about 300 kDa; and the electro-functional polymer has a weight-average molecular weight in the range of from about 500 g/mol to about 1,000,000 g/mol. E16. The method of any one of embodiments E1-E15, wherein the mole ratio of (i) thio-functional groups —R¹—SH to (ii) thiol-reactive groups is about 0.5:1 to about 1.2:1, about 0.6:1 to about 1.2:1, or about 0.67:1. E17. The method of any one of embodiments E1-E16, wherein the poly(ethylene glycol) is linear, branched, a dendrimer, or multi-armed.

E18. A method of providing a retinal tamponade in an eye of a subject, the method comprising: injecting an effective amount of a nucleo-functional polymer, an electro-functional polymer, and a pharmaceutical composition into the vitreous cavity of the eye of the subject; and allowing the nucleo-functional polymer and the electro-functional polymer to react to form a hydrogel, which forms the retinal tamponade comprising the pharmaceutical composition in the vitreous cavity; wherein the nucleo-functional polymer is a biocompatible polymer comprising hyaluronic acid containing a plurality of thio-functional —R¹—SH, wherein R¹ is hydrolyzable, and the electro-functional polymer is a biocompatible polymer comprising poly(ethylene glycol) containing at least one thiol-reactive group.

E19. The method of embodiment E18, wherein —R¹—SH is

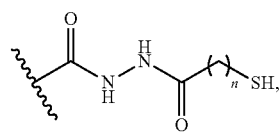

and n=1-3 or n=2. E20. The method of embodiment E18,

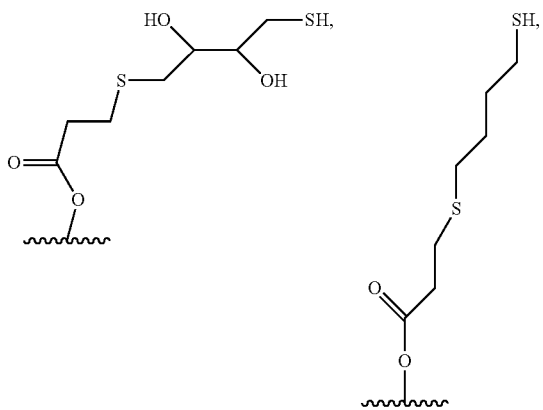

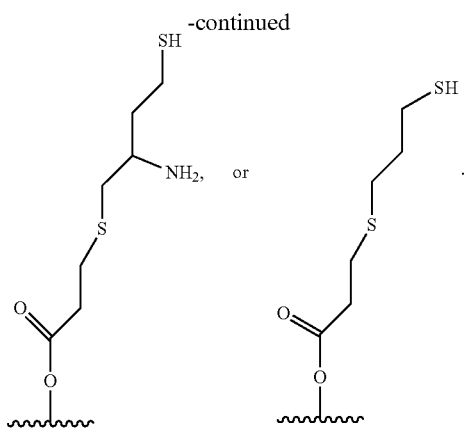

wherein —R$^1$—SH is

E21. The method of any one of embodiments E18-E20, wherein the nucleo-functional polymer and the electro-functional polymer are focally applied in the vitreous cavity. E22. The method of any one of embodiments E18-E21, wherein up to about 200 μL of the nucleo-functional polymer, the electro-functional polymer, or a combination thereof is administered. E23. The method of any one of embodiments E18-E22, wherein the retinal tamponade comprises a pharmaceutical agent. E24. The method of any one of embodiments E18-E23, wherein the retinal tamponade is provided in the eye of a subject having a physical discontinuity in retinal tissue, a tear in retinal tissue, a break in retinal tissue, or a hole in retinal tissue. E25. The method of any one of embodiments E18-E24, wherein the retinal tamponade is provided in the eye of a subject having undergone surgery for a macular hole, having undergone surgery to remove at least a portion of an epiretinal membrane, having undergone a vitrectomy for vitreomacular traction, having a rhegmatogenous retinal detachment, having tractional retinal detachment, or having serous retinal detachment. E26. The method of any one of embodiments E18-E25, wherein the retinal tamponade is provided in the eye of a subject having undergone a fluid-air exchange. E27. The method of any one of embodiments E18-E26, wherein the eye is an air-filled eye. E28. The method of any one of embodiments E18-E27, wherein the hydrogel is formed on retinal tissue. E29. The method of any one of embodiments E18-E28, wherein the hydrogel forms the retinal tamponade by contacting an area of physical discontinuity in the retina. E30. The method of embodiment E29, wherein the physical discontinuity in the retina comprises a detachment, tear, break, hole, or combination thereof, in retinal tissue. E31. The method of any one of embodiments E18-E30, wherein the nucleo-functional polymer and the electro-functional polymer are injected separately as liquid aqueous pharmaceutical compositions or together as a single, liquid aqueous pharmaceutical composition to the vitreous cavity of the eye of the subject. E32. The method of embodiment E31, wherein the separate liquid aqueous pharmaceutical compositions or single liquid aqueous pharmaceutical composition has a pH in the range of about 6.9-7.2 to about 6.8 to about 7.6. E33. The method of any one of embodiments E18-E32, wherein the hydrogel has a transparency of at least 90% for light in the visible spectrum when measured through the hydrogel having a thickness of 2 cm. E34. The method of any one of embodiments E18-E33, wherein the hydrogel has a gelation time of less than about 10 minutes. E35. The method of any one of embodiments E18-E34, wherein the hydrogel undergoes complete biodegradation from the eye of the subject within about 3 days to about 7 days, about 2 weeks to about 8 weeks, or about 4 months to about 6 months, or within 12 months or 24 months. E36. The method of any one of embodiments E18-E35, wherein the hydrogel has a biodegradation half-life in the range of from about 1 week to about 3 weeks or from about 8 weeks to about 15 weeks when disposed within the vitreous cavity of an eye. E37. The method of any one of embodiments E18-E36, wherein the hydrogel generates a pressure within the eye of less than 25 mmHg. E38. The method of any one of embodiments E18-E37, wherein the nucleo-functional polymer has a weight-average molecular weight in the range of from about 75 kDa to about 300 kDa; and wherein the electro-functional polymer has a weight-average molecular weight in the range of from about 500 g/mol to about 1,000,000 g/mol. E39. The method of any one of embodiments E18-E38, wherein the mole ratio of (i) thio-functional groups —R$^1$—SH to (ii) thiol-reactive groups is about 0.5:1 to about 1.2:1, about 0.6:1 to about 1.2:1, or about 0.67:1. E40. The method of any one of embodiments E18-E39, wherein the retinal tamponade is provided in the eye of a subject having undergone a vitrectomy. E41. The method of any one of embodiments E18-E40, wherein the poly(ethylene glycol) is linear, branched, a dendrimer, or multi-armed. E42. A method of forming a hydrogel in an eye of a subject, the method comprising: injecting an effective amount of a nucleo-functional polymer and an electro-functional polymer into the eye of the subject; and allowing the nucleo-functional polymer and the electro-functional polymer to react to form a hydrogel in the eye of the subject; wherein the nucleo-functional polymer is a biocompatible polymer comprising hyaluronic acid containing a plurality of thio-functional —R$^1$—SH, wherein R$^1$ is hydrolyzable, and the electro-functional polymer is a biocompatible polymer comprising poly(ethylene glycol) containing at least one thiol-reactive group.

E43. The method of embodiment E42, wherein —R$^1$—SH is

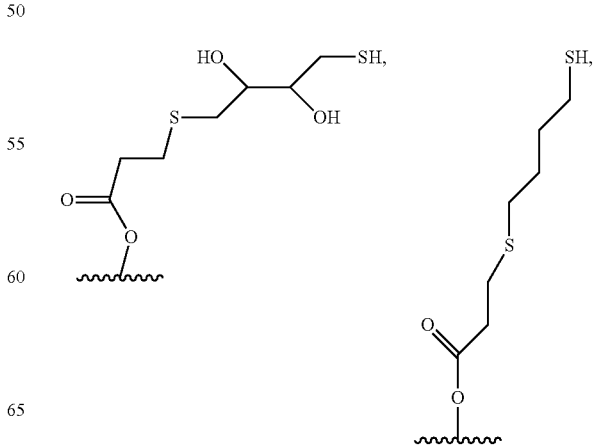

-continued

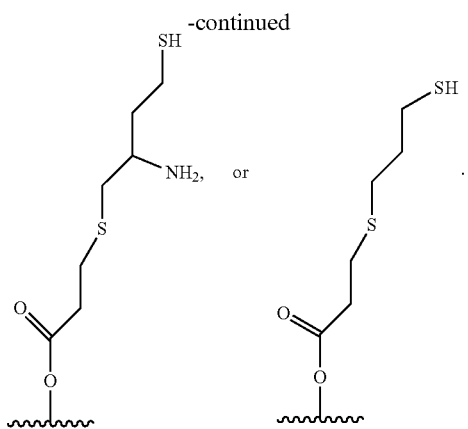

and n=1-3 or n=2. E44. The method of embodiment E42, wherein —R¹—SH is

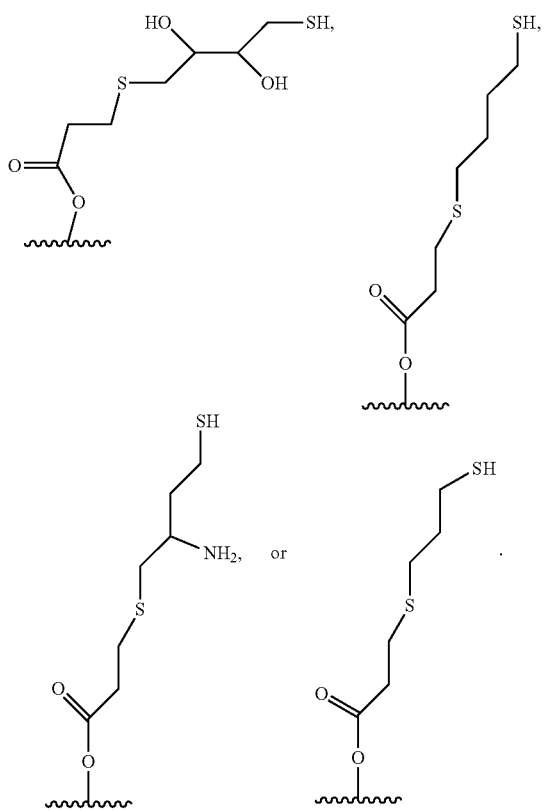

E45. The method of any one of embodiments E42-E44, wherein the nucleo-functional polymer and the electro-functional polymer are focally applied in the eye. E46. The method of any one of embodiments E42-E45, wherein up to about 200 μL of the nucleo-functional polymer, the electro-functional polymer, or a combination thereof is administered. E47. The method of any one of embodiments E42-E46, wherein the hydrogel is formed in the vitreous cavity of the eye of the subject. E48. The method of any one of embodiments E42-E47, wherein the hydrogel is formed in the eye of a subject having a physical discontinuity in the retinal tissue, a tear in the retinal tissue, a break in the retinal tissue, or a hole in the retinal tissue. E49. The method of any one of embodiments E42-E48, wherein the hydrogel is formed in the eye of a subject having undergone surgery for a macular hole, having undergone surgery to remove at least a portion of a epiretinal membrane, having undergone a vitrectomy, having a rhegmatogenous retinal detachment, having tractional retinal detachment, or having serous retinal detachment. E50. The method of any one of embodiments E42-E49, wherein the nucleo-functional polymer and the electro-functional polymer are injected into the eye separately as liquid aqueous compositions or together as a single, liquid aqueous composition. E51. The method of any one of embodiments E42-E50, wherein the nucleo-functional polymer and the electro-functional polymer are injected into the vitreous cavity of the eye. E52. The method of embodiment E50 or E51, wherein the separate liquid aqueous compositions or single liquid aqueous composition has a pH in the range of about 6.9 to about 7.2 or about 6.8 to about 7.6. E53. The method of any one of embodiments E42-E52, wherein the hydrogel has a transparency of at least 90% for light in the visible spectrum when measured through the hydrogel having a thickness of 2 cm. E54. The method of any one of embodiments E42-E53, wherein the hydrogel has a gelation time of less than about 10 minutes. E55. The method of any one of embodiments E42-E54, wherein the hydrogel undergoes complete biodegradation from the eye of the subject within about 3 days to about 7 days, about 2 weeks to about 8 weeks, or about 4 months to about 6 months, or within 12 months or 24 months. E56. The method of any one of embodiments E42-E55, wherein the hydrogel has a biodegradation half-life in the range of from about 1 week to about 3 weeks or from about 8 weeks to about 15 weeks when disposed within the eye. E57. The method of any one of embodiments E42-E56, wherein the hydrogel generates a pressure within the eye of less than 25 mmHg. E58. The method of any one of embodiments E42-E57, wherein the nucleo-functional polymer has a weight-average molecular weight in the range of from about 75 kDa to about 300 kDa; and the electro-functional polymer has a weight-average molecular weight in the range of from about 500 g/mol to about 1,000,000 g/mol. E59. The method of any one of embodiments E42-E58, wherein the mole ratio of (i) thio-functional groups —R¹—SH to (ii) thiol-reactive groups is about 0.5:1 to about 1.2:1, about 0.6:1 to about 1.2:1, or about 0.67:1. E60. The method of any one of embodiments E42-E59, wherein the poly(ethylene glycol) is linear, branched, a dendrimer, or multi-armed. E61. The method of any one of embodiments E42-E60, further comprising injecting a pharmaceutical composition into the eye. E62. The method of embodiment E61, wherein the pharmaceutical composition is injected into the eye together with the nucleo-functional polymer, together with the electro-functional polymer, or together with both the nucleo-functional polymer and the electro-functional polymer.

E63. An injectable, ocular formulation for forming a hydrogel in an eye of a subject, the formulation comprising: a nucleo-functional polymer that is a biocompatible polymer comprising hyaluronic acid containing a plurality of thio-functional groups —R¹—SH, wherein R¹ is hydrolyzable; an electro-functional polymer that is a biocompatible polymer comprising poly(ethylene glycol) containing at least one thiol-reactive group; and a liquid pharmaceutically acceptable carrier comprising 5X phosphate buffered saline (PBS) that is suitable for administration of the ocular formulation to the eye of the subject; wherein the ocular formulation has a pH in the range of about 6.9 to about 7.2 or about 6.8 to about 7.6, an osmolality in the range of about 260 mOsm/kg to about 310 mOsm/kg and the formulation forms a hydrogel in the eye of the subject.

E64. The formulation of embodiment E63, wherein —R¹—SH is

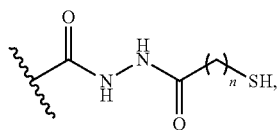

and n=1-3 or n=2.

E65. The formulation of embodiment E63, wherein —R¹—SH is

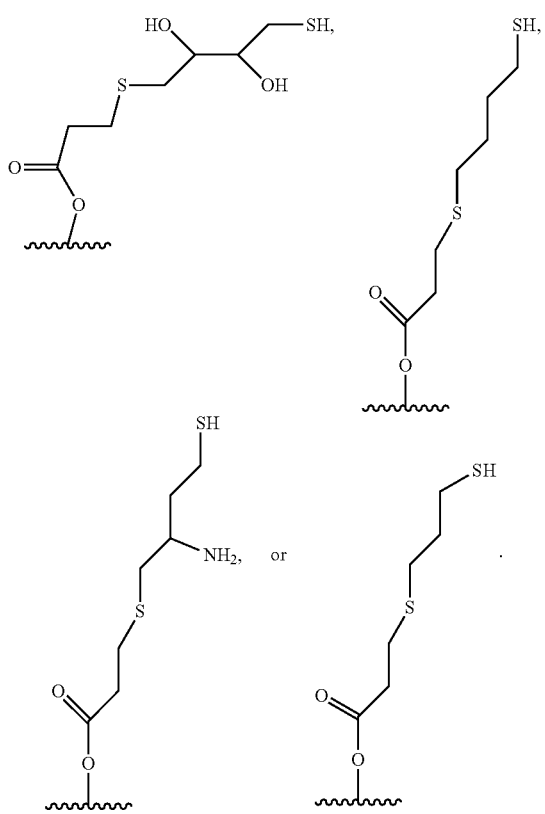

E66. The formulation of any one of embodiments E63-E65, wherein the formulation has a viscosity of about 500 cP to about 10,000 cP. E67. The formulation of anyone of embodiments 63-66, wherein a first solution comprising the nucleo-functional polymer and a second solution comprising the electro-functional polymer are mixed to form the formulation. E68. The formulation of any one of embodiments E63-E67, wherein the 5×PBS comprises about 50 mM to about 90 mM sodium chloride, about 2.5 mM to about 3 mM potassium, about 50 mM sodium phosphate, about 9 nM potassium phosphate, or combinations thereof. E69. The formulation of any one of embodiments E63-E68, wherein the formulation has an osmolality in the range of about 260 mOsm/kg to about 310 mOsm/kg. E70. The formulation of any one of embodiments E63-E69, wherein the formulation has an osmolality in the range of about 300 mOsm/kg to about 320 mOsm/kg. E71. The formulation of any one of embodiments E63-E70, wherein the formulation has a viscosity of between about 500 cP and about 10,000 cP at around 8-13 minutes after mixing the first and second solutions to form the formulation. E72. The formulation of any one of embodiments E63-E71, wherein the formulation has a viscosity of between about 500 cP and about 10,000 cP at around 17-18 minutes after mixing the first and second solutions to form the formulation. E73. The formulation of any one of embodiments E63-E72, wherein the formulation has an initial, low viscosity after mixing the first and second solutions to form the formulation such that the formulation can be administered through a needle having a gauge of less than or equal to 23 using a force of no more than 15 N. E74. The formulation of any one of embodiments E63-E73, wherein the formulation is formed following separate injection of the nucleo-functional polymer and the electro-functional polymer into the vitreous cavity of the eye of the subject. E75. The formulation of any one of embodiments E63-E74, wherein the nucleo-functional polymer, the electro-functional polymer, or both, are reconstituted in 5×PBS. E76. The formulation of embodiment E75, wherein the reconstituted nucleo-functional polymer, the reconstituted electro-functional polymer, or both, has a pH between about 6.9 to about 7.2 or about 6.8 to about 7.6. E77. The formulation of any one of embodiments E63-E76, wherein the nucleo-functional polymer, the electro-functional polymer, or both, are reconstituted after having been stored for at least 1 week, at least 1 month, at least 2 months, at least 6 months, at least 12 months, at least 15 months, at least 18 months, at least 20 months, or at least 24 months. E78. The formulation of any one of embodiments E63-E77, wherein the poly(ethylene glycol) is linear, branched, a dendrimer, or multi-armed. E79. The formulation of any one of embodiments E63-E78, wherein the hydrogel formed in the eye of the subject undergoes complete biodegradation from the eye of the subject within about 3 days to about 7 days, about 2 weeks to about 8 weeks, about 4 months to about 6 months, or within 12 months or 24 months. E80. The formulation of any one of embodiments E63-E79, wherein the hydrogel formed in the eye of the subject results in a pressure within the eye of less than 25 mmHg.

E81. A kit comprising an injectable ocular formulation for forming a hydrogel in an eye of a subject, the kit comprising: a nucleo-functional polymer that is a biocompatible polymer comprising hyaluronic acid containing a plurality of thio-functional —R¹—SH, wherein R¹ is hydrolyzable; an electro-functional polymer that is a biocompatible polymer comprising poly(ethylene glycol) containing at least one thiol-reactive group; and a liquid pharmaceutically acceptable carrier comprising phosphate buffered saline (PBS) that is suitable for administration of the ocular formulation to the eye of the subject; wherein the ocular formulation has a pH in the range of about 6.9 to about 7.2 or about 6.8 to about 7.6, an osmolality in the range of about 260 mOsm/kg to about 310 mOsm/kg and the formulation forms a hydrogel in the eye of the subject.

E82. The kit of embodiment E81, wherein —R¹—SH is

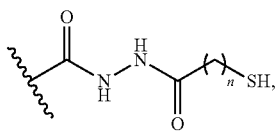

and n=1-3 or n=2.

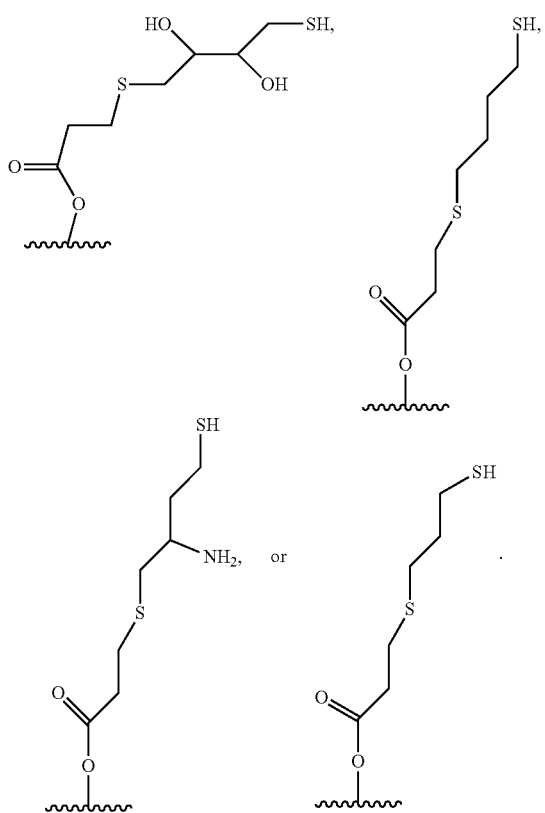

E83. The kit of embodiment E81, wherein —R¹—SH is

E84. The kit of any one of embodiments E81-E83, wherein the liquid pharmaceutically acceptable carrier comprises 1X or 5X phosphate buffered saline (PBS). E85. The kit of any one of embodiments E81-E84, wherein a first solution comprises the nucleo-functional polymer and a second solution comprises the electro-functional polymer; and the first and second solutions are mixed to form the injectable ocular formulation. E86. The kit of any one of embodiments E81-E85, wherein the PBS comprises about 50 mM to about 90 mM sodium chloride, about 2.5 mM to about 3 mM potassium, about 50 mM sodium phosphate, about 9 nM potassium phosphate, or combinations thereof. E87. The kit of any one of embodiments E81-E86, wherein the injectable ocular formulation has an osmolality in the range of about 260 mOsm/kg to about 310 mOsm/kg. E88. The kit of any one of embodiments E81-E87, wherein the injectable ocular formulation has an osmolality in the range of about 300 mOsm/kg to about 320 mOsm/kg. E89. The kit of any one of embodiments E81-E88, wherein the injectable ocular formulation has a viscosity of between about 500 cP and about 10,000 cP at around 8-13 minutes after mixing the first and second solutions to form the injectable ocular formulation. E90. The kit of any one of embodiments E81-E89, wherein the injectable ocular formulation has a viscosity of between about 500 cP and about 10,000 cP at around 17-18 minutes after mixing the first and second solutions to form the injectable ocular formulation. E91. The kit of any one of embodiments E81-E90, wherein the injectable ocular formulation has an initial, low viscosity after mixing the first and second solutions to form the injectable ocular formulation such that the injectable ocular formulation can be administered through a needle having a gauge of less than or equal to 23 using a force of no more than 15 N. E92. The kit of any one of embodiments E81-E91, wherein the injectable ocular formulation is formed following separate injection of the nucleo-functional polymer and the electro-functional polymer into a vitreous cavity of the eye of the subject. E93. The kit of any one of embodiments E81-E92, wherein the nucleo-functional polymer, the electro-functional polymer, or both, are reconstituted in 5x PBS. E94. The kit of embodiment E93, wherein the reconstituted nucleo-functional polymer, the reconstituted electro-functional polymer, or both, has a pH between about 6.9 to about 7.2 or about 6.8 to about 7.6. E95. The kit of any one of embodiments E81-E94, wherein the nucleo-functional polymer, the electro-functional polymer, or both, are reconstituted after having been stored for at least 1 week, at least 1 month, at least 2 months, at least 6 months, at least 12 months, at least 15 months, at least 18 months, at least 20 months, or at least 24 months. E96. The kit of any one of embodiments E81-E95, wherein the poly(ethylene glycol) is linear, branched, a dendrimer, or multi-armed. E97. The kit of any one of embodiments E81-E96, wherein the hydrogel formed in the eye of the subject undergoes complete biodegradation from the eye of the subject within about 3 days to about 7 days, about 2 weeks to about 8 weeks, about 4 months to about 6 months, or within 12 months or 24 months. E98. The kit of any one of embodiments E81-E97, wherein the hydrogel formed in the eye of the subject results in a pressure within the eye of less than 25 mmHg.

Various aspects and embodiments of the invention are described in further detail below, along with further description of multiple advantages provided by the invention.

DETAILED DESCRIPTION OF THE INVENTION

Figure 1:
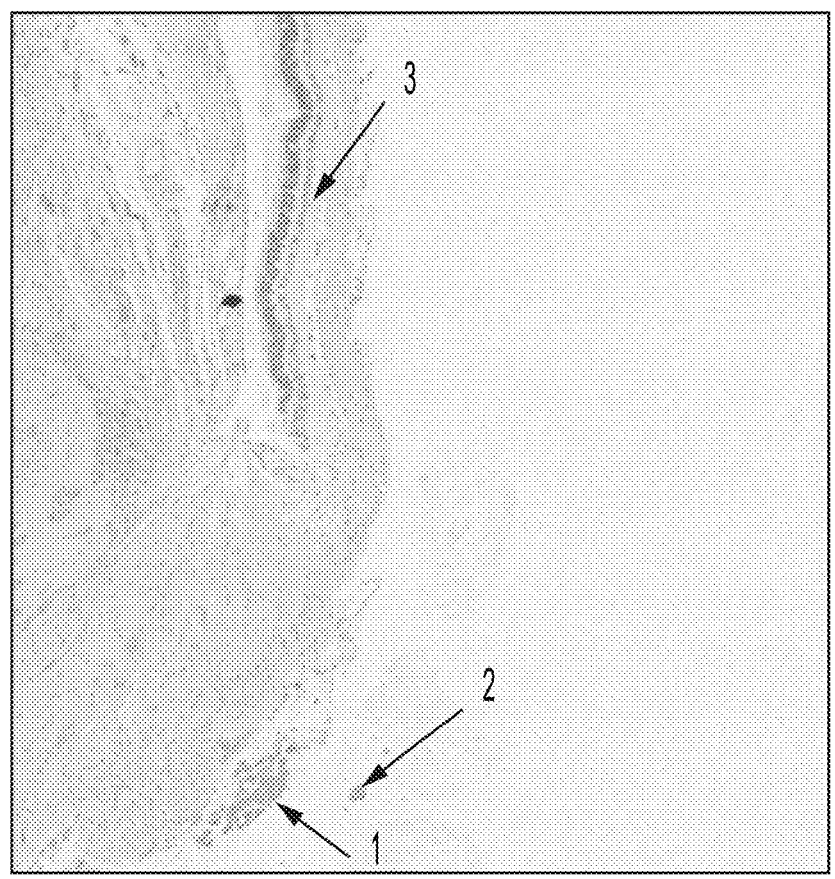
FIG. 1 shows macrophages containing basophilic material observed in the connective tissue adjacent to the optic nerve (1), including within multinucleated giant cells (2) in that location in rabbits treated with a tPVA-based formulation and hydrogel (PYK-1107), and the retina (3) appears normal.

Various aspects of the invention are set forth below in sections; however, aspects of the invention described in one particular section are not to be limited to any particular section and are applicable to other sections as appropriate and as would be understood by those of ordinary skill in the art.

Definitions

To facilitate an understanding of the present invention, a number of terms and phrases are defined below.

The terms "a" and "an" as used herein mean "one or more" and include the plural unless the context is inappropriate.

The term "about," when used to modify a numerical value herein, means ±10% of that numerical value. For example, "about 100" refers to any number between, and including, 90 to 110.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$ alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc.

The term "aryl" is art-recognized and refers to a carbocyclic aromatic group. Representative aryl groups include phenyl, naphthyl, anthracenyl, and the like. Unless specified otherwise, the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. In certain embodiments, the aromatic ring is substituted at one or more ring positions with halogen, alkyl, hydroxyl, or alkoxyl. In certain other embodiments, the aromatic ring is not substituted, i.e., it is unsubstituted.

The term "aralkyl" refers to an alkyl group substituted with an aryl group.

The term "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. Unless specified otherwise, the heteroaryl ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO$_2$alkyl, carbonyl, carboxyl, alkylthio, sulfonyl, sulfonamido, sulfonamide, ketone, aldehyde, ester, heterocyclyl, aryl or heteroaryl moieties, —CF$_3$, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls. In certain embodiments, the heteroaryl ring is substituted at one or more ring positions with halogen, alkyl, hydroxyl, or alkoxyl. In certain other embodiments, the heteroaryl ring is not substituted, i.e., it is unsubstituted.

The term "heteroaralkyl" refers to an alkyl group substituted with a heteroaryl group.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The terms "amine" and "amino" are art-recognized and refer to both unsubstituted and substituted amines, e.g., a moiety represented by the general formula -N($R^{50}$)($R^{51}$), wherein $R^{50}$ and $R^{51}$ each independently represent hydrogen, alkyl, cycloalkyl, heterocyclyl, alkenyl, aryl, aralkyl, or —(CH$_2$)$_m$—$R^{61}$; or $R^{50}$ and $R^{51}$, taken together with the N atom to which they are attached complete a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, $R^{50}$ and $R^{51}$ each independently represent hydrogen, alkyl, alkenyl, or —(CH$_2$)$_m$—$R^{61}$.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH$_2$)$_m$—$R^{61}$, where m and $R^{61}$ are described above.

The term "amide" or "amido" as used herein refers to a radical of the form —R$_a$C(O)N(R$_b$)—, —R$_a$C(O)N(R$_b$)R$_c$—, —C(O)NR$_b$R$_c$, or —C(O)NH$_2$, wherein R$_a$, R$_b$ and R$_c$ are each independently alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, or nitro. The amide can be attached to another group through the carbon, the nitrogen, R$_b$, R$_c$, or R$_a$. The amide also may be cyclic, for example R$_b$ and R$_c$, R$_a$ and R$_b$, or R$_a$ and R$_c$ may be joined to form a 3- to 12-membered ring, such as a 3- to 10-membered ring or a 5- to 6-membered ring.

As used herein, the terms "subject" and "patient" refer to organisms to be treated by the methods of the present invention. In certain embodiments, such organisms are mammals (e.g., murines, simians, equines, bovines, porcines, canines, felines, primates, and the like), and in some embodiments, such organisms are humans.

As used herein, the term "effective amount" refers to the amount of a compound, composition, or formulation (e.g., a compound, composition, or formulation of the present invention) sufficient to effect beneficial or desired results. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. In certain embodiments, the pharmaceutically acceptable carrier is, or comprises, balanced salt solution. The compositions or formulations also can include stabilizers and preservatives. For examples of carriers, stabilizers and adjuvants/excipients, see, e.g., Seema Thakral, Jayesh Sonje, Bhushan Munjal, Raj Suryanarayanan, Stabilizers and their interaction with formulation components in frozen and freeze-dried protein formulations, Advanced Drug Delivery Reviews, Volume 173, 2021, Pages 1-19, ISSN 0169-409X, https://doi.org/10.1016/j.addr.2021.03.003, the disclosure of which is incorporated by reference herein in its entirety. The compositions or formulations may optionally contain a dye. Accordingly, in certain embodiments, the composition or formulation further comprises a dye.

Throughout the description, the molecular weight of a polymer is weight-average molecular weight unless the context clearly indicates otherwise, such as clearly indicating that the molecular weight of the polymer is the number-average molecular weight.

Throughout the description, where compositions or formulations and kits are described as having, including, or comprising specific components, or where processes and methods are described as having, including, or comprising specific steps, it is contemplated that, additionally, there are compositions or formulations and kits of the present invention that consist essentially of, or consist of, the recited components, and that there are processes and methods according to the present invention that consist essentially of, or consist of, the recited processing steps.

As a general matter, compositions or formulations specifying a percentage are by weight unless otherwise specified. Further, if a variable is not accompanied by a definition, then the previous definition of the variable controls.

Formulations for Forming a Retinal Tamponade/Retinal Sealant

One aspect of the invention provides an injectable formulation, the formulation comprising: (a) a nucleo-functional polymer that is a biocompatible polymer containing a plurality of thio-functional —$R^1$—SH, wherein $R^1$ is hydrolyzable; (b) an electro-functional polymer that is a biocompatible polymer containing at least one thiol-reactive group; and (c) a liquid pharmaceutically acceptable carrier for administration to the eye of a subject. In certain embodiments, the formulation may comprise a pharmaceutical agent. The formulation can be further characterized by, for example, the identity and structure of the nucleo-functional polymer, the identity and structure of the electro-functional polymer, the identity of the pharmaceutical agent, physical characteristics of the hydrogel formed and other features described herein below. In certain embodiments, the site of interest of the subject is the eye and the formulation is an ocular formulation.

The hydrogel is formed by reaction of the nucleo-functional polymer and electro-functional polymer, and the subsequent uptake of water from the subject (e.g., the subject's eye or other tissue of interest). In certain embodiments, the thio-functional group —$R^1$—SH is

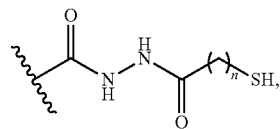

where n=1-3. In some embodiments, n=2.

In certain embodiments, the thio-functional group —$R^1$—SH is:

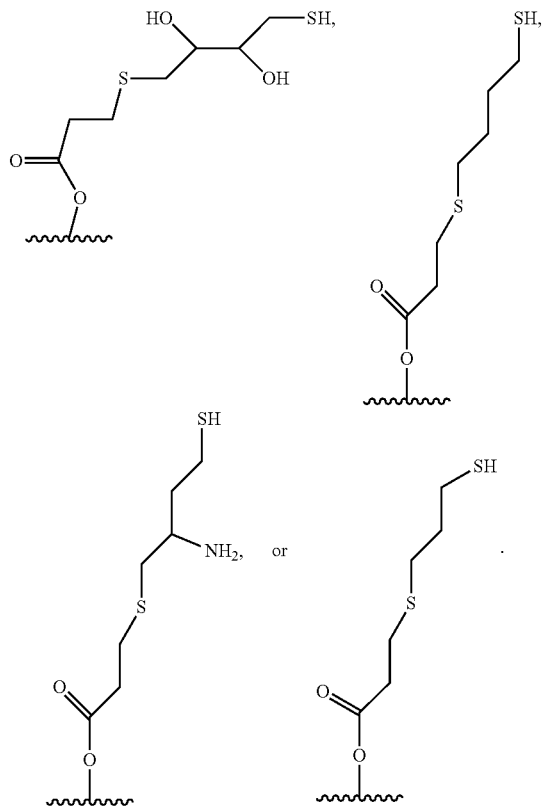

In certain embodiments, the nucleo-functional polymer is a thiolated hyaluronic acid (tHA) polymer and the electro-functional group is a poly(ethylene glycol) (PEG) polymer comprising thiol-reactive groups. In the more specific embodiment of a tHA polymer as the nucleo-functional polymer and a PEG polymer comprising thiol-reactive groups as the electro-functional polymer, the hydrogel is formed by a cross-linking reaction of tHA with PEG comprising thiol-reactive groups. In certain embodiments, the tHA polymer can be prepared as disclosed in the literature. See, e.g., Shu et al, Biomacromolecules 2002, 3, 1304-1311 and US 2023/0081482 for descriptions of the potential tHA polymer structures. In some embodiments, poly(ethylene glycol) polymers containing thiol-reactive groups (e.g., an acrylate, methacrylate, maleimidyl, or vinyl-sulfone) may be used. In certain embodiments, crosslinking of the tHA and the PEG comprising thiol-reactive groups occurs through a Michael addition, without use of initiators or an external energy source (e.g., UV light).

Therapeutic Methods and Injectable, Ocular Formulations for Forming A Hydrogel

The invention provides methods and polymer compositions for treating retinal detachment and other ocular disorders, where the methods employ polymer compositions that can form a hydrogel in the eye of a subject. The methods include, for example, methods for contacting retinal tissue in the eye of a subject with a hydrogel, methods for supporting retinal tissue, methods for treating a subject with a retinal detachment, methods for treating hypotony, methods for treating a choroidal effusion, methods for supporting tissue in or adjacent to the anterior chamber of the eye, and methods of maintaining or expanding a nasolacrimal duct, and injectable, ocular formulations for forming a hydrogel. The methods and compositions are described in more detail herein.

Methods for Contacting Retinal Tissue in the Eye of a Subject with a Hydrogel

One aspect of the invention provides a method of contacting retinal tissue in the eye of a subject with a hydrogel. The method comprises (a) administering to the vitreous cavity of an eye of the subject an effective amount of a nucleo-functional polymer and an electro-functional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —$R^1$—SH wherein $R^1$ is hydrolyzable, and the electro-functional polymer is a biocompatible polymer containing at least one thiol-reactive group. In certain embodiments, the thio-functional group —$R^1$—SH is

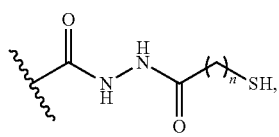

where n=1-3. In some embodiments, n=2.

In certain embodiments, the thio-functional group —$R^1$—SH is:

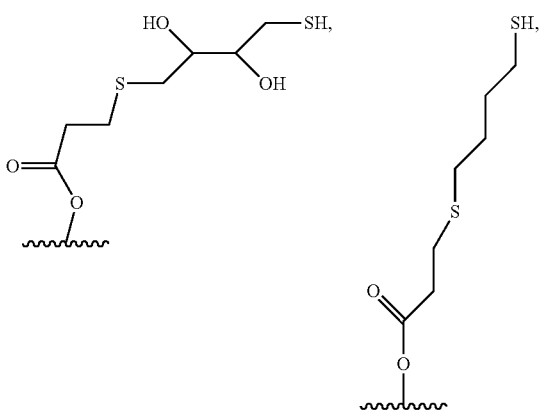

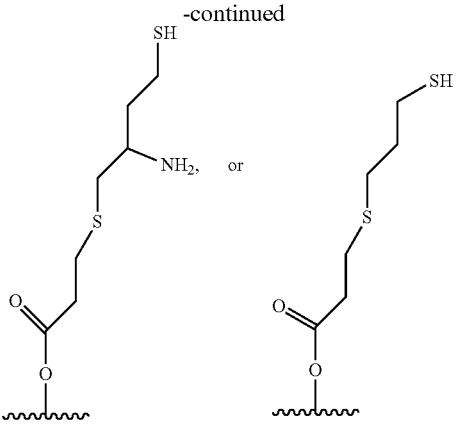

In certain embodiments, the nucleo-functional polymer is a thiolated hyaluronic acid (tHA) polymer and the electro-functional group is a poly(ethylene glycol) (PEG) polymer comprising thiol-reactive groups. In certain embodiments, the hydrogel is an extended-release hydrogel. In some embodiments, the hydrogel comprises a pharmaceutical agent.

The method can be further characterized by, for example, the identity of the subject. In certain embodiments, subject has a physical discontinuity in the retinal tissue. In certain embodiments, the physical discontinuity is a tear in the retinal tissue, a break in the retinal tissue, or a hole in the retinal tissue. In other embodiments, the subject has undergone surgery for a macular hole, has undergone surgery to remove at least a portion of a epiretinal membrane, or has undergone a vitrectomy for vitreomacular traction. In other embodiments, the subject has a detachment of at least a portion of the retinal tissue. The retinal detachment may be, for example, a rhegmatogenous retinal detachment. Alternatively, the retinal detachment may be tractional retinal detachment or serous retinal detachment.

The nucleo-functional polymer and an electro-functional polymer are administered to the eye of the subject in an amount effective to produce a hydrogel that contacts retinal tissue. This effective amount may vary depending on the volume of the eye cavity to be filled, such that a large eye cavity will require more nucleo-functional polymer and an electro-functional polymer to produce a hydrogel occupying more volume, as can be readily determined by those of skill in the art based on the teachings provided herein. In some embodiments, the polymers and/or hydrogel is administered focally to an area or tissue in the eye, for example the retina.

The method can also be further characterized by, for example, the identity of the nucleo-functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups. In certain embodiments, the nucleo-functional polymer is a biocompatible polymer containing a plurality of thio-functional groups —$R^1$—SH wherein $R^1$ is hydrolyzable, and the electro-functional polymer is a biocompatible polymer containing at least one thiol-reactive group. In certain embodiments, the thio-functional group —$R^1$—SH is

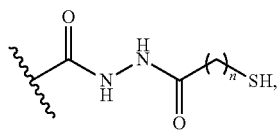

where n=1-3. In some embodiments, n=2.

In certain embodiments, the thio-functional group —R$^1$—SH is:

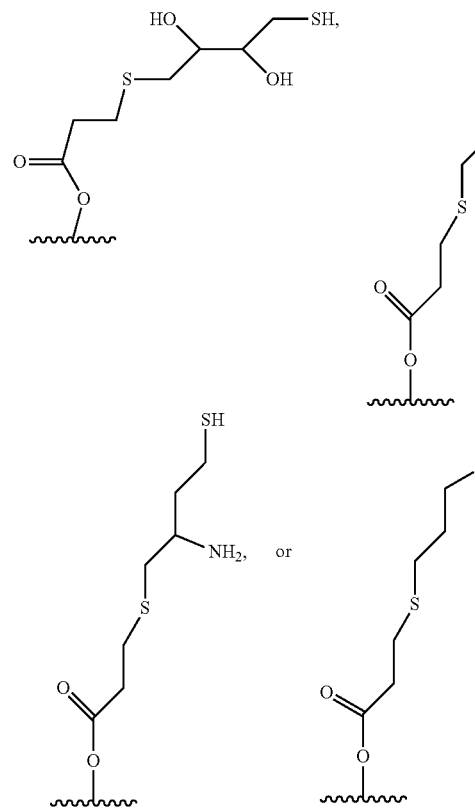

In certain embodiments, the nucleo-functional polymer is a thiolated hyaluronic acid (tHA) polymer and the electro-functional group is a poly(ethylene glycol) (PEG) polymer comprising thiol-reactive groups.

Methods for Contacting or Supporting Retinal Tissue

Another aspect of the invention provides a method of contacting or supporting retinal tissue in the eye of a subject, the method comprising: (a) administering to the vitreous cavity of an eye of the subject an effective amount of nucleo-functional polymer and an electro-functional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —R$^1$—SH wherein R$^1$ is hydrolyzable, and the electro-functional polymer is a biocompatible polymer containing at least one thiol-reactive group. In certain embodiments, the thio-functional group —R$^1$—SH is

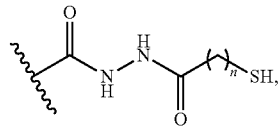

where n=1-3. In some embodiments, n=2.

In certain embodiments, the thio-functional group —R$^1$—SH is:

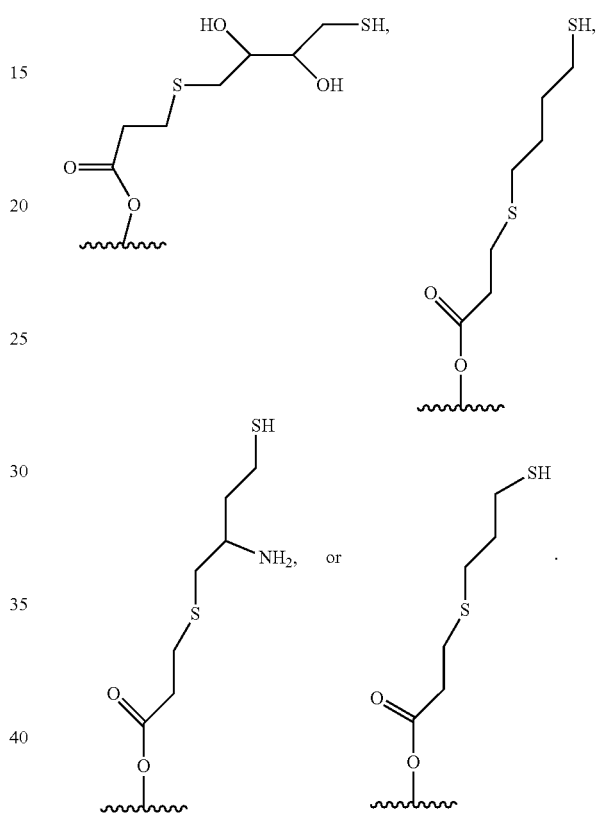

In certain embodiments, the nucleo-functional polymer is a thiolated hyaluronic acid (tHA) polymer and the electro-functional group is a poly(ethylene glycol) (PEG) polymer comprising thiol-reactive groups. In certain embodiments, the hydrogel is an extended-release hydrogel. In some embodiments, the hydrogel comprises a pharmaceutical agent.

The method can be further characterized by, for example, the identity of the subject. In certain embodiments, subject has a physical discontinuity in the retinal tissue. In certain embodiments, the physical discontinuity is a tear in the retinal tissue, a break in the retinal tissue, or a hole in the retinal tissue. In other embodiments, the subject has undergone surgery for a macular hole, has undergone surgery to remove at least a portion of an epiretinal membrane, or has undergone a vitrectomy for vitreomacular traction. In other embodiments, the subject has a detachment of at least a portion of the retinal tissue. The retinal detachment may be, for example, a rhegmatogenous retinal detachment. Alternatively, the retinal detachment may be tractional retinal detachment or serous retinal detachment.

The nucleo-functional polymer and an electro-functional polymer are administered to the eye of the subject in an amount effective to contact or support the retinal tissue, such as an amount that upon formation of the hydrogel, the hydrogel contacts the retinal tissue. In some embodiments, the polymers and/or hydrogel is administered focally to a portion of the retina.

The method can also be further characterized by, for example, the identity of the nucleo-functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

Methods for Treating a Subject with a Retinal Detachment

Another aspect of the invention provides a method of treating a subject with a retinal detachment, the method comprising: (a) administering a nucleo-functional polymer and an electro-functional polymer to the vitreous cavity of an eye of the subject with a detachment of at least a portion of retinal tissue; and (b) allowing the nucleo-functional polymer and the electro-functional polymer to react to form a hydrogel in the vitreous cavity; wherein the hydrogel contacts or supports the retinal tissue during reattachment of the portion of the retinal tissue, the nucleo-functional polymer is a biocompatible polymer containing a plurality of thio-functional groups —R$^1$—SH wherein R is hydrolyzable, and the electro-functional polymer is a biocompatible polymer containing at least one thiol-reactive group. In some embodiments, the polymers and/or hydrogel is administered focally to a portion of the retina. In certain embodiments, the hydrogel is an extended-release hydrogel. In some embodiments, the hydrogel comprises a pharmaceutical agent.

The method can be further characterized by, for example, the nature of the retinal detachment. In certain embodiments, the retinal detachment is a rhegmatogenous retinal detachment. In other embodiments, the subject has tractional retinal detachment or serous retinal detachment.

The nucleo-functional polymer and an electro-functional polymer are administered to the eye of the subject in an amount effective to support the retinal tissue, thereby facilitating treatment of the retinal detachment.

The method can also be further characterized by, for example, the identity of the nucleo-functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups. In certain embodiments, the nucleo-functional polymer is a biocompatible polymer containing a plurality of thio-functional groups —R$^1$—SH wherein R$^1$ is hydrolyzable, and the electro-functional polymer is a biocompatible polymer containing at least one thiol-reactive group. In certain embodiments, the thio-functional group —R$^1$—SH is

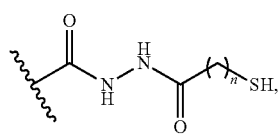

where n=1-3. In some embodiments, n=2.

In certain embodiments, the thio-functional group —R$^1$—SH is:

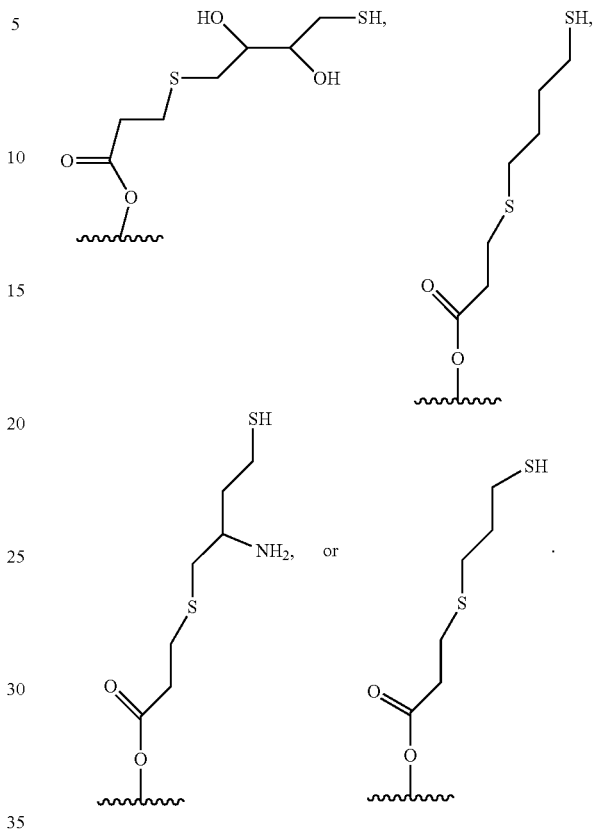

In certain embodiments, the nucleo-functional polymer is a thiolated hyaluronic acid (tHA) polymer and the electro-functional group is a poly(ethylene glycol) (PEG) polymer comprising thiol-reactive groups. In some embodiments, the polymers and/or hydrogel is administered focally to a portion of the retina. In certain embodiments, the hydrogel is an extended-release hydrogel. In some embodiments, the hydrogel comprises a pharmaceutical agent.

Methods for Treating Hypotony

Another aspect of the invention provides a method of treating a subject with low pressure in the eye (i.e., hypotony), the method comprising: (a) administering an effective amount of a nucleo-functional polymer and an electro-functional polymer to the vitreous cavity of an eye of the subject; and (b) allowing the nucleo-functional polymer and the electro-functional polymer to react to form a hydrogel in the vitreous cavity; to thereby treat the subject with low pressure in the eye, wherein the nucleo-functional polymer is a biocompatible polymer containing a plurality of thio-functional groups —R$^1$—SH wherein R$^1$ is hydrolyzable, and the electro-functional polymer is a biocompatible polymer containing at least one thiol-reactive group.

In certain embodiments, the thio-functional group —R$^1$—SH is

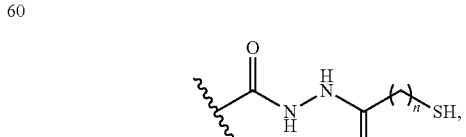

where n=1-3. In some embodiments, n=2.

In certain embodiments, the thio-functional group —R$^1$—SH is

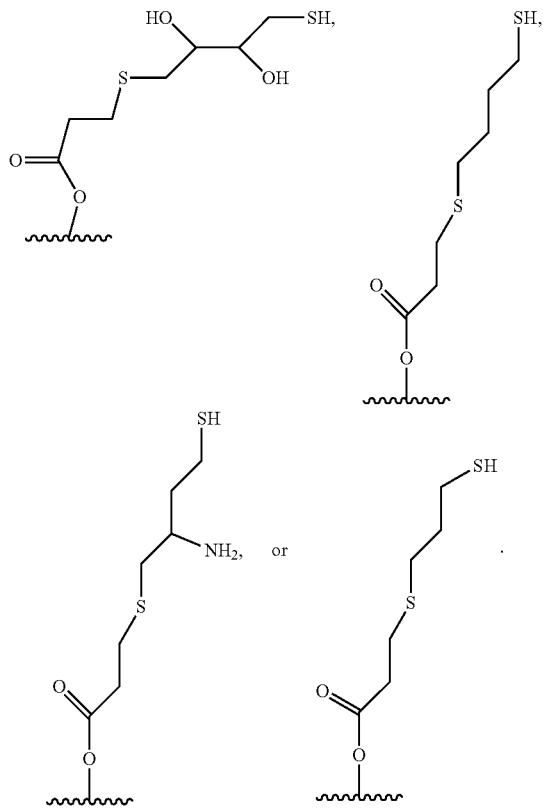

In certain embodiments, the nucleo-functional polymer is a thiolated hyaluronic acid (tHA) polymer and the electro-functional group is a poly(ethylene glycol) (PEG) polymer comprising thiol-reactive groups. In certain embodiments, the method causes an increase in pressure of at least about 1 mmHg, 2 mmHg, 5 mmHg, 7 mmHg, or 10 mmHg in the eye of the subject. In certain embodiments, the hydrogel is an extended-release hydrogel. In some embodiments, the hydrogel comprises a pharmaceutical agent.

The method can also be further characterized by, for example, the identity of the nucleo functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

Methods for Treating Choroidal Effusion

Another aspect of the invention provides a method of treating a choroidal effusion, the method comprising: (a) administering an effective amount of a nucleo-functional polymer and an electro-functional polymer to an eye of the subject having a choroidal effusion; and (b) allowing the nucleo-functional polymer and the electro-functional polymer to react to form a hydrogel; to thereby treat the choroidal effusion, wherein the nucleo-functional polymer is a biocompatible polymer containing a plurality of thio-functional groups —R$^1$—SH wherein R$^1$ is hydrolyzable, and the electro-functional polymer is a biocompatible polymer containing at least one thiol-reactive group. In certain embodiments, the thio-functional group —R$^1$—SH is

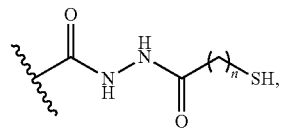

where n=1-3. In some embodiments, n=2.

In certain embodiments, the thio-functional group —R$^1$—SH is:

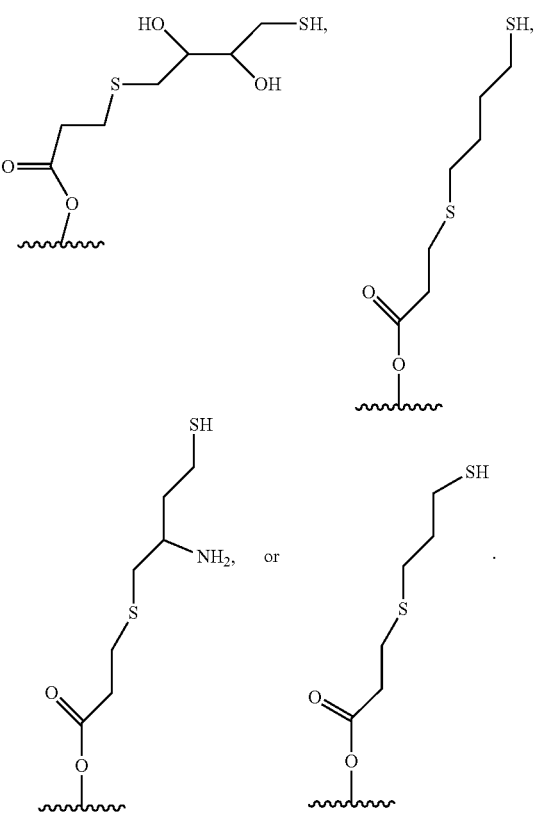

In certain embodiments, the nucleo-functional polymer is a thiolated hyaluronic acid (tHA) polymer and the electro-functional group is a poly(ethylene glycol) (PEG) polymer comprising thiol-reactive groups. In some embodiments, the polymers and/or hydrogel is administered focally to a portion of the retina. In certain embodiments, the hydrogel is an extended-release hydrogel. In some embodiments, the hydrogel comprises a pharmaceutical agent.

In certain embodiments, the subject suffers from a choroidal effusion (e.g., a serous choroidal effusion or hemorrhagic choroidal effusion). In certain embodiments, the choroidal effusion is a serous choroidal effusion or hemorrhagic choroidal effusion.

The method can also be further characterized by, for example, the identity of the nucleo functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

Methods for Improving Visual Performance

Another aspect of the invention provides a method of improving visual performance in a patient suffering from a retinal detachment, the method comprising: (a) administering to the vitreous cavity of an eye of the subject an effective amount of nucleo-functional polymer and an electro-functional polymer; and (b) allowing the nucleo-functional polymer and the electro-functional polymer to react to form a hydrogel in the vitreous cavity; wherein the nucleo-functional polymer is a biocompatible polymer containing a plurality of thio-functional groups —$R^1$—SH wherein $R^1$ is hydrolyzable, and the electro-functional polymer is a biocompatible polymer containing at least one thiol-reactive group. In certain embodiments, the thio-functional group —$R^1$—SH is

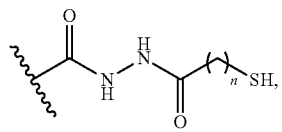

where n=1-3.

In some embodiments, n=2. In certain embodiments, the thio-functional group —$R^1$—SH is:

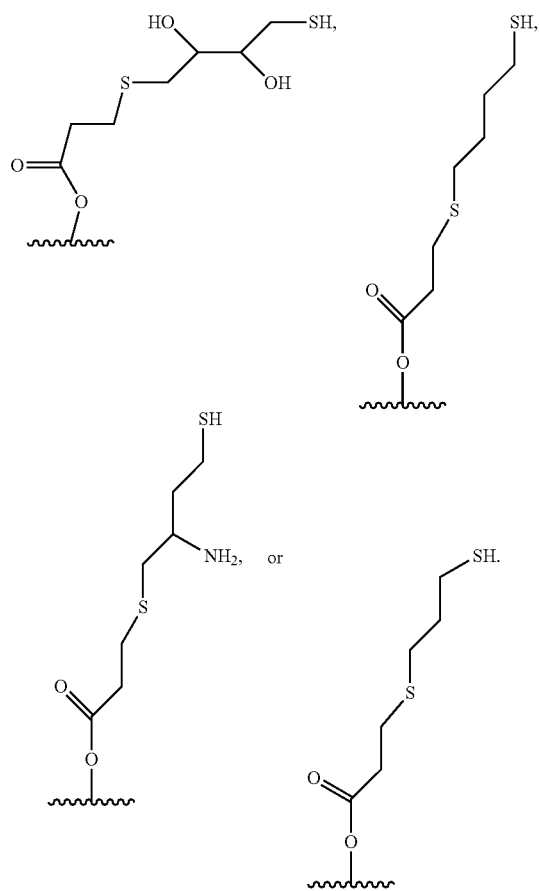

In certain embodiments, the nucleo-functional polymer is a thiolated hyaluronic acid (tHA) polymer and the electro-functional group is a poly(ethylene glycol) (PEG) polymer comprising thiol-reactive groups. In some embodiments, the polymers and/or hydrogel is administered focally to a portion of the retina. In certain embodiments, the hydrogel is an extended-release hydrogel. In some embodiments, the hydrogel comprises a pharmaceutical agent.

The method can be further characterized by, for example, the identity of the subject. In certain embodiments, the subject may have suffered from a retinal detachment that is a rhegmatogenous retinal detachment. Alternatively, the retinal detachment may be tractional retinal detachment or serous retinal detachment.

The nucleo-functional polymer and an electro-functional polymer are administered to the eye of the subject in an amount effective to contact or support the retinal tissue, such as an amount that upon formation of the hydrogel, the hydrogel contacts the retinal tissue.

Visual performance pertains to the patient's overall vision quality and includes a patient's ability to see clearly, as well as ability to distinguish between an object and its background. One aspect of visual performance is visual acuity, which is a measure of a patient's ability to see clearly. Visual acuity can be assessed, for example, by using conventional "eye charts" in which visual acuity is evaluated by the ability to discern letters of a certain size, with five letters of a given size present on each line (see, e.g., the "ETDRS" eye chart described in the Hawkins, B. S., & Chakravarthy, U. (2013). Chapter 94-Retina-Related Clinical Trials: A Resource Bibliography. (S. J. Ryan, Ed.) Retina (Retina, Fifth Edition, pp. 1589-1613). Elsevier Inc. http://doi.org/10.1016/B978-1-4557-0737-9.00094-1). Evaluation of visual acuity may also be achieved by measuring reading speed and reading time. Visual acuity may be measured to evaluate whether administration of a necrosis inhibitor and/or an apoptosis inhibitor to the affected eye preserves or permits improvement of visual acuity (e.g., to 20/40 vision or to 20/20 vision). In certain embodiments, a Snellen chart can be used to measure a patient's visual acuity, and the measurement can be taken under conditions that test low-contrast visual acuity or under conditions that test high-contrast visual acuity. Also, the visual acuity measurement can be taken under scotopic conditions, mesopic conditions, and/or photopic conditions.

Another aspect of visual performance is contrast sensitivity, which is a measure of the patient's ability to distinguish between an object and its background. The contrast sensitivity can be measured under various light conditions, including, for example, photopic conditions, mesopic conditions, and scotopic conditions. In certain embodiments, the contrast sensitivity is measured under mesopic conditions.

In certain embodiments, the improvement in visual performance provided by the method is improved visual acuity. In certain embodiments, the improvement in visual performance provided by the method is improved visual acuity under scotopic conditions. In certain embodiments, the improvement in visual performance provided by the method is improved visual acuity under mesopic conditions. In certain embodiments, the improvement in visual performance provided by the method is improved visual acuity under photopic conditions. In certain embodiments, the improvement in visual acuity is a two-line improvement in the patient's vision as measured using the Snellen chart. In certain other embodiments, the improvement in visual acuity is a one-line improvement in the patient's vision as measured using the Snellen chart.

In certain embodiments, the improvement in visual performance provided by the method is improved contrast sensitivity. The improvement in contrast sensitivity can be measured under various light conditions, such as photopic conditions, mesopic conditions, and scotopic conditions. In certain embodiments, the improvement in visual performance provided by the method is improved contrast sensitivity under photopic conditions. In certain embodiments, the improvement in visual performance provided by the method is improved contrast sensitivity under mesopic conditions. In certain embodiments, the improvement in visual performance provided by the method is improved contrast sensitivity under scotopic conditions.

Results achieved by the methods can be characterized according to the patient's improvement in contrast sensitivity. For example, in certain embodiments, the improvement in contrast sensitivity is at least a 10%, 20%, 30%, 50%, 60%, 70%, 80%, 90%, or 100% improvement measured under mesopic conditions using an art-recognized test, such as a Holladay Automated Contrast Sensitivity System. In certain embodiments, the improvement in contrast sensitivity is at least a 10%, 20%, 30%, 50%, 60%, 70%, 80%, 90%, or 100% improvement measured under photopic conditions using an art-recognized test, such as a Holladay Automated Contrast Sensitivity System. In certain other embodiments, the improvement in contrast sensitivity is at least a 10%, 20%, 30%, 50%, 60%, 70%, 80%, 90%, or 100% improvement measured under mesopic conditions or scotopic conditions using an art-recognized test, such a Holladay Automated Contrast Sensitivity System.

Visual performance may also be measured by determining whether there is an increase in the thickness of the macula (e.g., macula thickness is 15% thicker than, 35% thicker than, 50% thicker than, 60% thicker than, 70% thicker than, or 80% thicker than a macula without the treatment as measured by optical coherence tomography (OCT); an improvement of the photoreceptor cell layer or its subdivisions as seen in the OCT; an improvement of visual field (e.g., by at least 10% in the mean standard deviation on the Humphrey Visual Field Test; an improvement of an electroretinograph (ERG), a measurement of the electrical response of the retina to light stimulation, (e.g., to increase ERG amplitude by at least 15%); and or preservation or improvement of multifocal ERG, which evaluates the response of the retina to multifocal stimulation and allows characterization of the function of a limited area of the retina.

Visual performance may also be measured by electrooculography (EOG), which is a technique for measuring the resting potential of the retina. EOG is particularly useful for the assessment of RPE function. EOG may be used to evaluate whether administration of a necrosis inhibitor and/or an apoptosis inhibitor to the retina of the affected eye preserves or permits improvement in, for example, the Arden ratio (e.g., an increase in Arden ratio of at least 10%).

Visual performance may also be assessed through fundus autofluorescence (AF) imaging, which is a clinical tool that allows evaluation of the interaction between photoreceptor cells and the RPE. For example, increased fundus AF or decreased fundus AF has been shown to occur in AMD and other ocular disorders. Fundus AF imaging may be used to evaluate whether administration of a necrosis inhibitor and/or an apoptosis inhibitor to the retina of the affected eye slows disease progression.

Visual performance may also be assessed by microperimetry, which monitors retinal visual function against retinal thickness or structure and the condition of the subject's fixation over time. Microperimetry may be used to assess whether administration of a necrosis inhibitor and/or an apoptosis inhibitor to the retina of the affected eye preserves or permits improvement in retinal sensitivity and fixation.

The method can also be further characterized by, for example, the identity of the nucleo-functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

Methods for Contacting or Supporting Tissue in or Adjacent to the Anterior Chamber of the Eye Another aspect of the invention provides a method of supporting tissue in or adjacent to the anterior chamber of the eye of a subject, the method comprising: (a) administering an effective amount of a nucleo-functional polymer and an electro-functional polymer to the anterior chamber of an eye of the subject; and (b) allowing the nucleo-functional polymer and the electro-functional polymer to react to form a hydrogel in the anterior chamber; wherein the nucleo-functional polymer is a biocompatible polymer containing a plurality of thio-functional groups —R$^1$—SH wherein R$^1$ is hydrolyzable, and the electro-functional polymer is a biocompatible polymer containing at least one thiol-reactive group. In certain embodiments, the thio-functional group —R$^1$—SH is

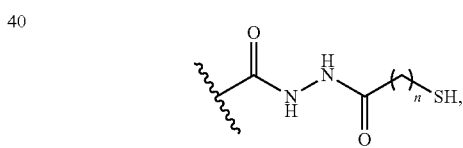

where n=1-3. In some embodiments, n=2.

In certain embodiments, the thio-functional group —R$^1$—SH is:

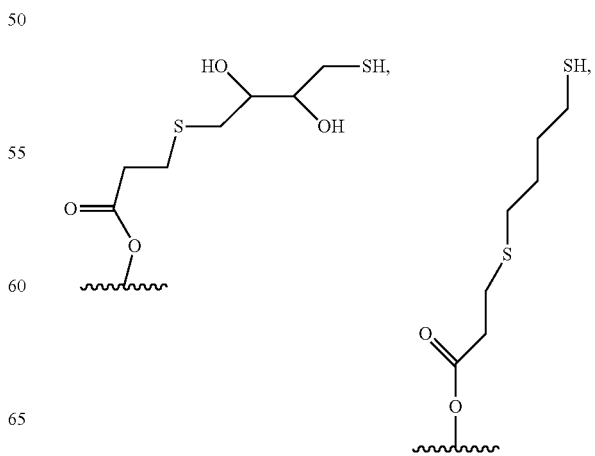

-continued

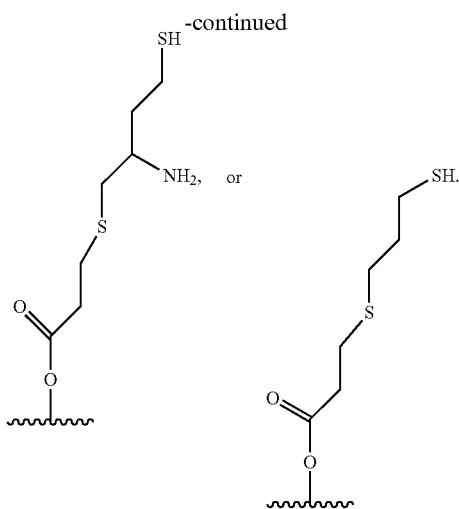

In certain embodiments, the nucleo-functional polymer is a thiolated hyaluronic acid (tHA) polymer and the electro-functional group is a poly(ethylene glycol) (PEG) polymer comprising thiol-reactive groups. In certain embodiments, the method supports a graft in the anterior chamber of the eye. The hydrogel achieves contacting or supporting tissue in or adjacent to the anterior chamber of the eye by coming into contact with such tissue and optionally exerting a force (e.g., 0.1, 0.5, 1.0, or 2.0 N) against such tissue. In certain embodiments, the hydrogel is an extended-release hydrogel. In some embodiments, the hydrogel comprises a pharmaceutical agent.

The method can also be further characterized by, for example, the identity of the nucleofunctional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

Methods for Maintaining or Expanding a Nasolacrimal Duct

Another aspect of the invention provides a method of maintaining or expanding a nasolacrimal duct in a subject, the method comprising: (a) administering an effective amount of a nucleo-functional polymer and an electro-functional polymer to a nasolacrimal duct in a subject; and (b) allowing the nucleo-functional polymer and the electro-functional polymer to react to form a hydrogel in the nasolacrimal duct; wherein the nucleo-functional polymer is a biocompatible polymer containing a plurality of thio-functional groups —$R^1$—SH wherein $R^1$ is hydrolyzable, and the electro-functional polymer is a biocompatible polymer containing at least one thiol-reactive group. In certain embodiments, the thio-functional group —$R^1$—SH is

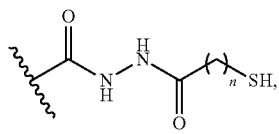

where n=1-3. In some embodiments, n=2.

In certain embodiments, the thio-functional group —$R^1$—SH is

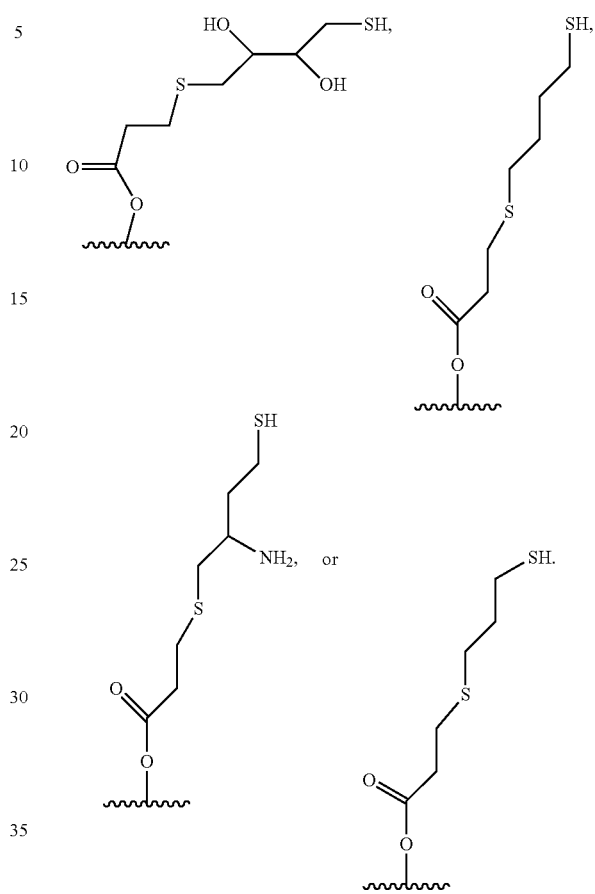

In certain embodiments, the nucleo-functional polymer is a thiolated hyaluronic acid (tHA) polymer and the electro-functional group is a poly(ethylene glycol) (PEG) polymer comprising thiol-reactive groups. The hydrogel achieves maintaining or expanding a nasolacrimal duct by coming into contact with such tissue and optionally exerting a force (e.g., 0.1, 0.5, 1.0, or 2.0 N) against such tissue. In certain embodiments, the hydrogel is an extended-release hydrogel. In some embodiments, the hydrogel comprises a pharmaceutical agent.

The method can also be further characterized by, for example, the identity of the nucleo-functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

Injectable, Ocular Formulation for Forming a Hydrogel

Another aspect of the invention provides an injectable, ocular formulation for forming a hydrogel in the eye of a subject, the formulation comprising: (a) a nucleo-functional polymer that is a biocompatible polymer containing a plurality of thio-functional groups —$R^1$—SH wherein $R^1$ is hydrolyzable; (b) an electro-functional polymer that is a biocompatible polymer containing at least one thiol-reactive group; and (c) a liquid pharmaceutically acceptable carrier for administration to the eye of a subject. In certain embodiments, the thio-functional group —$R^1$—SH is

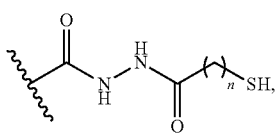

where n=1-3.

In some embodiments, n=2. In certain embodiments, the thio-functional group —R$^1$—SH is:

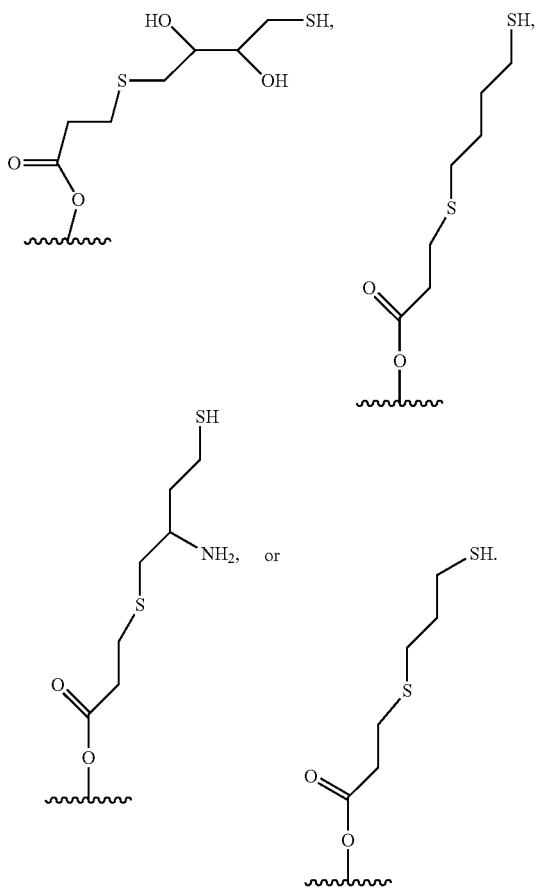

In certain embodiments, the nucleo-functional polymer is a thiolated hyaluronic acid (tHA) polymer and the electro-functional group is a poly(ethylene glycol) (PEG) polymer comprising thiol-reactive groups. In some embodiments, the polymers and/or hydrogel is administered focally to a portion of the retina. In certain embodiments, the hydrogel formed by the formulation is an extended-release hydrogel. In some embodiments, the formulation for forming a hydrogel comprises a pharmaceutical agent.

The formulation can be further characterized by, for example, the identity of the nucleo-functional polymer, the identity of the electro-functional polymer, physical characteristics of the hydrogel formed, and other features described herein. In certain embodiments, the nucleo-functional polymer is a thiolated hyaluronic acid (tHA) polymer and the electro-functional polymer is a poly(ethylene glycol) (PEG) polymer comprising thiol-reactive groups.

General Features of the Methods and Injectable Ocular Formulation

General features of the methods and injectable ocular formulation are further described herein.

Exemplary Features of the Hydrogel

The therapeutic methods and compositions for forming hydrogels can be further characterized according to features of the hydrogel. Exemplary features of the hydrogel include, for example, refractive index, transparency, density, gelation time, elastic modulus, viscosity (e.g., dynamic viscosity), biodegradation, and pressure generated by the hydrogen within the eye or other location into which the polymers for forming a hydrogel are inserted.

The hydrogel is formed by reaction of the nucleo-functional polymer and electro-functional polymer, and the subsequent update of water from the subject (e.g., the subject's eye). In the more specific embodiment of a thiolated hyaluronic acid (tHA) polymer as the nucleo-functional polymer and a poly(ethylene glycol) (PEG) containing thiol-reactive groups as the electro-functional polymer, the hydrogel is formed by a cross-linking reaction of thiolated hyaluronic acid (tHA) with poly(ethylene glycol) (PEG) containing thiol-reactive groups. The thiolated hyaluronic acid (tHA) polymer can be prepared according to procedures described in the literature (see, for example, Shu et al, Biomacromolecules 2002, 3, 1304-1311 and US 2023/0081482 for descriptions of the potential tHA polymer structures, which is hereby incorporated by reference in its entirety), whereby thiol groups are incorporated into hyaluronic acid (HA) by coupling thiol functionalities to the hydroxyl groups of the hyaluronic acid, or through use of protected thiol functionalities with subsequent deprotection. Certain poly(ethylene glycol) polymers containing thiol-reactive groups (e.g., an acrylate, methacrylate, maleimidyl, or N-hydroxysuccinimidyl) have been described in the literature (see, for example, U.S. Patent Application Publication No. 2016/0009872).

Crosslinking of the thiolated hyaluronic acid (tHA) and the poly(ethylene glycol) containing thiol-reactive groups occurs through a Michael addition, without formation of byproducts and does not require use of toxic initiators or a UV source. Further, there is no medically significant release of heat during the cross-linking reaction. Moreover, a freeze-thaw process is not required, as is commonly used to form other types of hydrogels, for example poly(vinyl alcohol) hydrogels. Therefore, the nucleo-functional polymer and electro-functional polymer can be mixed easily in an operating room. Also, to the extent there are any unreacted nucleo-functional polymer and/or electro-functional polymer, the molecular weight of these components is desirably low enough that they will be readily cleared from the eye by natural processes.

Transparency

The therapeutic methods and compositions can be characterized according to the transparency of the hydrogel formed. For example, in certain embodiments, the hydrogel has a transparency of at least 95% for light in the visible spectrum when measured through hydrogel having a thickness of 1 cm. In certain embodiments, the hydrogel has a transparency of at least 90%, 94%, or 98% for light in the visible spectrum when measured through hydrogel having a thickness of 2 cm.

Density

The therapeutic methods and compositions can be characterized according to the density of the hydrogel formed. For example, in certain embodiments, the hydrogel has a density in the range of about 1 to about 1.5 g/mL. In certain other embodiments, the hydrogel has a density in the range of about 1 to about 1.2 g/mL, about 1.1 to about 1.3 g/mL, about 1.2 to about 1.3 g/mL, or about 1.3 to about 1.5 g/mL. In certain other embodiments, the hydrogel has a density in the range of about 1 to about 1.2 g/mL. In certain other embodiments, the hydrogel has a density in the range of about 1 to about 1.1 g/mL.

Gelation Time

The therapeutic methods and compositions can be characterized according to the gelation time of the hydrogel (i.e., how long it takes for the hydrogel to form once the nucleo-functional polymer has been combined with the electro-functional polymer). For example, in certain embodiments, the hydrogel has a gelation time from about 1 minute to about 30 minutes after combining the nucleo-functional polymer and the electro-functional polymer. In certain embodiments, the hydrogel has a gelation time from about 5 minutes to about 30 minutes after combining the nucleo-functional polymer and the electro-functional polymer. In certain other embodiments, the hydrogel has a gelation time from about 5 minutes to about 20 minutes after combining the nucleo-functional polymer and the electro-functional polymer. In certain other embodiments, the hydrogel has a gelation time from about 5 minutes to about 10 minutes after combining the nucleo-functional polymer and the electro-functional polymer. In certain other embodiments, the hydrogel has a gelation time of less than about 1, 5, 10, 15, 20, 25, 30, 35, 40, 45, 50, 55 or 60 minutes.

Elastic Modulus

The therapeutic methods and compositions can be characterized according to the elastic modulus of the hydrogel formed. For example, in certain embodiments, the hydrogel has an elastic modulus in the range of from about 200 Pa to about 15 kPa at a temperature of 25° C. In certain embodiments, the hydrogel has an elastic modulus in the range of from about 600 Pa to about 7 kPa at a temperature of 25° C.

Biodegradation

The therapeutic methods and compositions can be characterized according to whether the hydrogel is biodegradable. Accordingly, in certain embodiments, the hydrogel is biodegradable. A biodegradable hydrogel can be further characterized according to the rate at which the hydrogel undergoes biodegradation from the eye. In certain embodiments, the hydrogel undergoes complete biodegradation from the eye of the subject within about 2 weeks to about 8 weeks. In certain embodiments, the hydrogel undergoes complete biodegradation from the eye of the subject within about 3 weeks to about 5 weeks. In certain embodiments, the hydrogel undergoes complete biodegradation from the eye of the subject within about 4 months to about 6 months. In certain embodiments, the hydrogel undergoes complete biodegradation from the eye of the subject within about 3 days to about 7 days. In certain embodiments, the hydrogel undergoes complete biodegradation from the eye of the subject within 1, 2, 3, 4, 5, 6, 7, 8, 9, 10, 11, 12, 13, 14, 15, 16, 17, 18, 19, 20, 21, 22, 23, or 24 weeks. In certain embodiments, the hydrogel undergoes complete biodegradation from the eye of the subject within 1, 2, 3, 4, 5, 6, 7, 8, 9, 10, 11, 12, 13, 14, 15, 16, 17, 18, 19, 20, 21, 22, 23, or 24 months.

In certain embodiments, the hydrogel has a biodegradation half-life in the range of from about 4 days to about 20 days when disposed within the vitreous cavity of an eye. In certain embodiments, the hydrogel has a biodegradation half-life in the range of from about 1 month to about 2 months when disposed within the vitreous cavity of an eye. In certain embodiments, the hydrogel has a biodegradation half-life in the range of from about 1 week to about 3 weeks when disposed within the vitreous cavity of an eye. In certain embodiments, the hydrogel has a biodegradation half-life in the range of from about 8 weeks to about 15 weeks when disposed within the vitreous cavity of an eye. In certain embodiments, the hydrogel has a biodegradation half-life of less than 1, 2, 3, 4, 5, 6, 7, 8, 9, 10, 11, 12, 13, 14, 15, 16, 17, 18, 19, 20, 21, 22, 23, or 24 weeks when disposed within the vitreous cavity of an eye. In certain embodiments, the hydrogel has a biodegradation half-life of less than 1, 2, 3, 4, 5, 6, 7, 8, 9, 10, 11, 12, 13, 14, 15, 16, 17, 18, 19, 20, 21, 22, 23, or 24 months when disposed within the vitreous cavity of an eye.

In yet other embodiments, the hydrogel turns into liquid after approximately 5 weeks at a temperature in the range of 20° C. to 25° C., or within from about 4 weeks to 10 weeks, including all values and ranges therein. In certain embodiments, the ester bonds remaining in the hydrogel may degrade at room temperature in solution, such as in a phosphate buffered saline solution, including for example 1X or 5X PBS. In certain embodiments, degradation of the hydrogel by hydrolysis may occur at a temperature in the range of about 30° C. to about 40° C., and/or within from about 4 to 5 months. In certain embodiments, degradation of the hydrogel in the presence of certain enzymes, for example hyaluronidase, may occur at a temperature in the range of about 30° C. to about 40° C., and/or within from about 4 to 8 weeks. In certain embodiments, degradation may begin after a few days and the hydrogel may be almost fully degraded, that is they form soluble products and the hydrogel turns in to liquid at around five weeks at a temperature in the range of 20° C. to 25° C. The rate of degradation will depend on a number of parameters, including total crosslink density, number of hydrolyzable linkages in the crosslinks, its ability to be degraded by hyaluronidase and other native enzymes, and the specifics of the environment.

Deliberate inclusion of degradable constituents into the nucleo-functional polymer and/or electro-functional polymer permits tuning of the degradability and longevity of these materials in their chosen application. Examples of degradable constituents can be in the crosslinks, or elsewhere and can include, for example, any molecule or group that contains an ester bond (e.g. carbamate, amide, carbonate, lactic acid, glycolic acid, caprolactone or others). In particular embodiments, the degradable elements may be incorporated at an amount in the range of 1 to 6 per crosslinker. Similarly, incorporation of other functional groups into the hydrogel, such as through modification of the hyaluronic acid or poly(ethylene glycol) provide further degrees of tuning of the properties of the hydrogel.

Features of the Nucleo-Functional Polymer

The compositions or formulations for forming a hydrogel described herein for treatment of various ocular disorders, can be characterized according to features of the nucleo-functional polymer. Accordingly, in certain embodiments, the nucleo-functional polymer is a naturally occurring biocompatible polymer comprising hyaluronic acid substituted by a plurality of thio-functional groups —$R^1$—SH. In certain embodiments, the thio-functional group —$R^1$—SH is —OC(O)—($C_1$-$C_6$ alkylene)—SH. In certain embodiments, the thio-functional group —$R^1$—SH is —OC(O)—($CH_2CH_2$)—SH. In certain embodiments, the thio-functional group —$R^1$—SH is

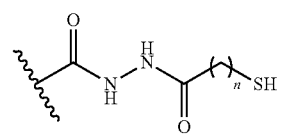

where n=1-3. In some embodiments, n=2.

In certain embodiments, the thio-functional group —R¹—SH is:

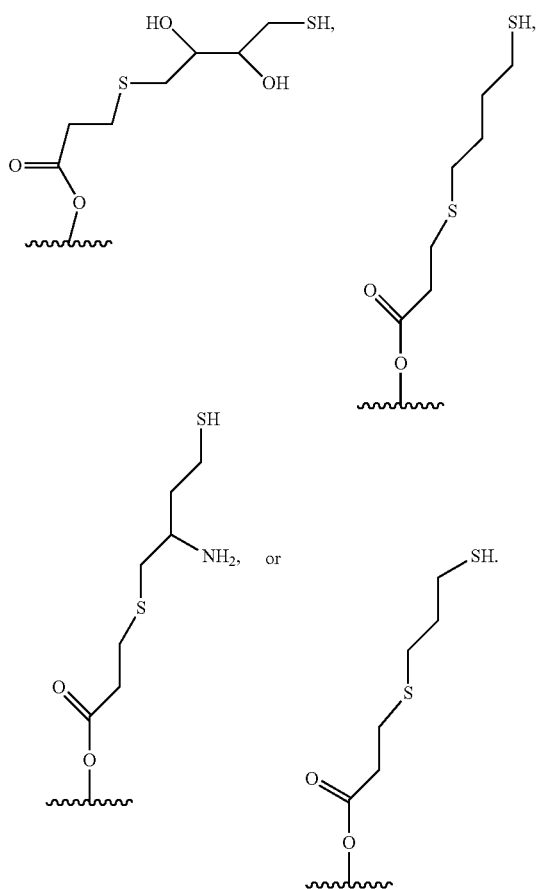

The nucleo-functional polymer may be further characterized according to its molecular weight, such as the weight-average molecular weight of the polymer. In certain embodiments, the nucleo-functional polymer has a weight-average molecular weight in the range of from about 75 kDa to about 300 kDa.

The amount of thiol groups on the HA can be controlled by the number of carboxyl groups on the HA that undergo reaction with the thiolating agent to generate the tHA. In certain embodiments, the HA molecules have 20-30% thiol-modification. In some embodiments, the HA molecules have about 25% thiol-modification. In certain embodiments, the amount of thiol functional groups on the HA may be characterized according to the molar ratio of thiol functional groups to HA polymer, such as from about 0.1:1 to about 10.0:1, including all values and ranges therein. In certain embodiments, the amount of thiol functional groups is from about 5.0:1 to about 7.0:1, including all values and ranges therein.

More generally, the nucleo-functional polymer containing a plurality of thio-functional groups can be prepared based on procedures described in the literature, such as reaction of carboxyl groups on the HA molecule with cysteamine (2-aminoethanethiol) using carbodiimide chemistry, resulting in the formation of amide bonds between the HA backbone and cysteamine, such as HA—COO—NH—CH$_2$—CH$_2$—SH, or through the use of Traut's reagent (2-iminothiolane), which can introduce thiol groups to primary amines on HA, forming thiol groups through a stable thioimidate bond, such as HA-NH—C(S)—CH$_2$—CH$_2$—SH.

Features of the Electro-Functional Polymer

The compositions or formulations for forming a hydrogel for ocular disorders can also be characterized according to the features of the electro-functional polymer. Accordingly, in certain embodiments, the electro-functional polymer is a biocompatible poly(ethylene glycol) polymer substituted by at least one thiol-reactive group.

In certain embodiments, the thiol-reactive group is an alpha-beta unsaturated ester, maleimidyl, or sulfone, each of which is optionally substituted by one or more occurrences of alkyl, aryl, or aralkyl. In certain embodiments, the thiol-reactive group is an alpha-beta unsaturated ester optionally substituted by one or more occurrences of alkyl, aryl, or aralkyl.

In certain embodiments, the thiol-reactive group is acrylate

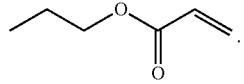

In certain embodiments, the thiol-reactive group is maleimide

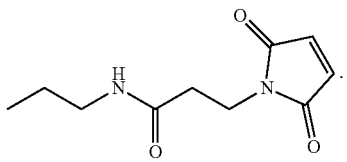

In certain embodiments the, the thiol-reactive group is vinyl sulfone

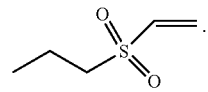

The electro-functional polymer may be further characterized according to its molecular weight, such as the weight-average molecular weight of the polymer. Accordingly, in certain embodiments, the electro-functional polymer has a weight-average molecular weight in the range of from about 500 g/mol to about 100,000 g/mol. In certain embodiments, the electro-functional polymer has a weight-average molecular weight in the range of from about 1,000 g/mol to about 50,000 g/mol. In certain embodiments, the electro-functional polymer has a weight-average molecular weight in the range of from about 2,000 g/mol to about 20,000 g/mol. In certain embodiments, the electro-functional polymer has a weight-average molecular weight less than about 100,000 g/mol. In certain embodiments, the electro-functional polymer has a weight-average molecular weight in the range of from about 2,700 g/mol to about 3,300 g/mol. In certain embodiments, the electro-functional polymer has a weight-average molecular weight in the range of from about 9,000 g/mol to about 11,000 g/mol. In certain embodiments, the electro-functional polymer has a weight-average molecular weight in the range of from about 18,000 g/mol to about 22,000 g/mol.

The electro-functional polymer may be a straight-chain polymer or a branched chain polymer. In yet other embodiments, the electro-functional polymer may be a multi-arm polymer, such as 4-arm polyethylene glycol malcimide, 4-arm polyethylene glycol acrylate, 4-arm polyethylene glycol vinyl sulfone, 8-arm polyethylene glycol maleimide, 8-arm polyethylene glycol acrylate, or 8-arm polyethylene glycol vinyl sulfone or combinations thereof.

In another embodiment, the electro-functional polymer may be a poly(ethylene glycol) end-capped with at least two thiol-reactive groups. The poly(ethylene glycol) may be linear, branched, a dendrimer, or multi-armed. The thiol reactive group may be, for example, an acrylate, methacrylate, malcimidyl, vinyl sulfone, haloacetyl, pyridyldithiol, N-hydroxysuccinimidyl. An exemplary poly(ethylene glycol) end-capped with thiol-reactive groups may be represented by the formula Y—[—O—CH$_2$CH$_2$—]$_n$—O—Y wherein each Y is a thiol-reactive group, and n is, for example, in the range of about 200 to about 20,000. In another embodiment, the electro-functional polymer may be CH$_2$=CHC(O)O—[—CH$_2$CH$_2$—O-]b-C(O)CH=CH$_2$, wherein b is, for example, in the range of about 200 to about 20,000. Alternatively or additionally to the linear embodiments depicted above, the poly(ethylene glycol) may be a dendrimer. For example, the poly(ethylene glycol) may be a 4 to 32 hydroxyl dendron. In further embodiments, the poly(ethylene glycol) may be multi-armed. In such embodiments, the poly(ethylene glycol) may be, for example, 4, 6 or 8 arm and hydroxy-terminated. The molecular weight of the poly(ethylene glycol) may be varied, and in some cases one of the thiol-reactive groups may be replaced with other structures to form dangling chains, rather than crosslinks. In certain embodiments, the molecular weight (Mw) is less than about 25,000, including all values and ranges from about 200 to about 20,000, such as about 200 to about 1,000, about 1,000 to about 10,000, etc. In addition, the degree of functionality may be varied, meaning that the poly(ethylene glycol) may be mono-functional, di-functional or multi-functional.

More generally, the electro-functional polymer can be purchased from commercial sources or prepared based on procedures described in the literature, such as by treating a nucleo-functional polymer with reagent(s) to install one or more electrophilic groups (e.g., by reacting polyethylene glycol with acrylic acid in an esterification reaction to form polyethylene glycol diacrylate, using procedures described in U.S. Pat. No. 6,828,401, which is incorporated by reference herein in its entirety, to form polyethylene glycol-maleimide, and using methods described in Lutolf, et al., "Synthetic matrix metalloproteinase-sensitive hydrogels for the conduction of tissue regeneration: engineering cell-invasion characteristics," *Proc. Natl. Acad. Sci. U.S.A.* (2003), which is incorporated by reference herein in its entirety, to form polyethylene glycol-vinyl sulfone by coupling PEG-OH with an excess of divinyl sulfone).

Relative Amount of Nucleo-Functional Polymer and Electro-Functional Polymer

In certain embodiments, the compositions or formulations for forming a hydrogel, as described herein, for treatment of various ocular disorders, can be characterized according to the relative amount of nucleo-functional polymer and electro-functional polymer used. Accordingly, in certain embodiments, the mole ratio of (i) thio-functional groups —R—SH to (ii) thiol-reactive groups is in the range of about 2:1 to about 1:2. In some embodiments the mole ratio of (i) thio-functional groups —R$^1$—SH to (ii) thiol-reactive groups is in the range of about 0.5:1 to about 1.2:1 or about 0.6:1 to about 1.2:1. In certain embodiments the mole ratio of (i) thio-functional groups —R$^1$—SH to (ii) thiol-reactive groups is about 0.67:1.

Once combined, the combination of the nucleo-functional polymer and the electro-functional polymer in certain embodiments are present in solution in the range of about 15 mg/mL to about 50 mg/mL, including all values and ranges therein, and in some embodiments are present in solution in the range of about 20 mg/mL to about 30 mg/mL.

Features of the Hydrogel System
Administration of the Formulations

In certain embodiments, the compositions or formulations for forming a hydrogel, as described herein, for treatment of various ocular disorders, can be characterized according to the features of administration. In certain embodiments, the nucleo-functional polymer, electro-functional polymer and a pharmaceutical carrier may be administered to the eye of a subject (e.g., by injection). In some embodiments, the nucleo-functional polymer, electro-functional polymer and a pharmaceutical carrier may be administered to the vitreal cavity of the eye of a subject. In certain embodiments, the nucleo-functional polymer, electro-functional polymer and a pharmaceutical carrier may be administered onto the surface of the retina of a subject following a vitrectomy. In certain embodiments, the nucleo-functional polymer, electro-functional polymer and a pharmaceutical carrier may be administered in a manner as to cover the surface, or a portion of the surface, of a defect (naturally occurring, i.e. retinal tear or man-made, ie. retinotomy) in the retina to prevent fluid leakage from the vitreal cavity. In either case the amount of formulation that is delivered could be, for example, in a range between about 25 uL to about 500 uL, including all values and ranges therein.

Additional Ocular-Specific Formulation Considerations

A major risk with the use of products administered to the eye (e.g., intravitreally-administered products) is the risk of a sterile inflammatory reaction due to unacceptably high levels of endotoxin. (Wang, et al., "Acute intraocular inflammation caused by endotoxin after intravitreal injection of counterfeit bevacizumab in Shanghai, China," *Ophthalmology* 120 (2): 355-61 (2013)). The ocular environment is particularly sensitive to endotoxins and sterile inflammatory reactions can be seen with formulations not specifically developed for intravitreal use. (Marticorena, et al., "Sterile endophthalmitis after intravitreal injections," *Mediators Inflamm.* 2012:928123 (2012)) In certain embodiments, the compositions and formulations described herein comprise less than or equal to about 0.2 endotoxin units (EU)/mL or 0.2 EU/device, a limit even lower than ISO standards 15798 & 11979-8 which recommend no more than (NMT) 0.5 EU/ml. In some embodiments, the compositions and formulations described herein comprises less than or equal to about 0.5 endotoxin units (EU)/mL. In addition, safety concerns of using unbuffered saline as a vehicle for intravitreal injection have been raised in the literature. Intravitreal injection of normal saline has been observed to induce vacuoles in the photoreceptor outer segments and RPE cells, as well as upregulation of inflammatory mediators including TNF-α, IL-1β, IL-6, and VEGF. These histopathological and cytokine markers have not been observed in mouse eyes that were injected with phosphate buffered vehicle (PBS) (Hombrebueno, et al., "Intravitreal Injection of Normal Saline Induces Retinal Degeneration in the C57BL/6J Mouse," *Transl Vis Sci Technol.* 3 (2): 3 (2014)), which in certain embodiments is the vehicle used for administration of the formulations described herein.

Features of the Pharmaceutical Agent for Hydrogel-Forming Formulations

Hydrogels formed by the formulations described herein, including extended-release hydrogels, may act as a drug sources and/or depots that may be used to deliver various pharmaceutical agents to a target site, including over an extended period of time. The pharmaceutical agents that may be use in the formulations and hydrogels, including extended-release hydrogels, described herein include anti-inflammatory agents, steroids, NSAIDS, intraocular pressure lowering drugs, antibiotics, pain relievers, inhibitors of vascular endothelial growth factor (VEGF), inhibitors of abnormal vascular growth or vascular leakage, inhibitors of abnormal cell proliferation, chemotherapeutics, anti-viral drugs, gene therapy viral vectors, etc., and combinations thereof. The pharmaceutical agents may be small molecules, proteins, DNA/RNA fragments, glycosaminoglycans, carbohydrates, nucleic acid, inorganic and organic biologically active compounds or other configurations, active portions of any of the proceeding molecules, and combinations thereof. The pharmaceutical agent may be soluble or non-soluble, or combinations thereof in the pharmaceutically acceptable carrier. The pharmaceutical agent may be dissolved in the composition or formulation, suspended as particles or encapsulated in particles (e.g., liposomes, amphiphilic polymer or solid polymer particles) and suspended, and combinations thereof. In some embodiments, the formulations, hydrogel, and/or extended-release hydrogel comprises more than one pharmaceutical agent. In certain embodiments, one or more pharmaceutical agent is included in the formulation comprising the nucleo-functional polymer. In certain embodiments, one or more pharmaceutical agent is included in the formulation comprising the electro-functional polymer. In certain embodiments, one or more pharmaceutical agents is included in the formulation comprising the nucleo-functional polymer and in the formulation comprising the electro-functional polymer. In some embodiments, one or more pharmaceutical agents is included in a formulation comprising both the nucleo-functional polymer and the electro-functional polymer.

Features of the Hydrogels for Controlling Drug Delivery

The compositions or formulations for forming hydrogels, including extended-release hydrogel, as described herein, for release and/or extended-release of a drug for the treatment of various disorders, including ocular disorders, can be further characterized according to the features of the hydrogel that control the release of the pharmaceutical agent into the local environment. Features of the hydrogel formulation for controlling the release of the pharmaceutical agent include: crosslink density or porosity, biodegradation rate, and a combination thereof.

Crosslink Density or Porosity of the Hydrogel

Following administration of a composition or formulation comprising a nucleo-functional polymer, an electro-functional polymer and one or more pharmaceutical agents within the target site (e.g., the eye) as described herein, the one or more pharmaceutical agents will diffuse out of the hydrogel, including extended-release hydrogels as provided herein, into the surrounding environment. The crosslink density of a resultant hydrogel, including an extended-release hydrogel, acts as a barrier to the diffusion of the one or more pharmaceutical agents within the hydrogel. A higher crosslink density results in a smaller pore size (i.e., distance between crosslinks). If the pore size is close to or less than the hydrodynamic radius of the pharmaceutical agent, then diffusion of the agent will be impeded and release from the hydrogel will be delayed. The crosslinking density of a hydrogel, including an extended-release hydrogel can be controlled by the molecular weight of the nucleo-functional and electro-functional polymers and the number of functional groups present on each polymer. A lower molecular weight between crosslinks will yield a higher crosslinking density as compared to a higher molecular weight. As previously described, in certain embodiments, the nucleo-functional polymer has a weight-average molecular weight in the range of from about 75 kDa to about 125 kDa and the electro-functional polymer has a molecular weight in the range of from about 500 g/mol to about 100,000 g/mol. Similarly, the molecular weight of each arm in a multi-arm electro-functional polymer has an impact on the porosity of the hydrogel, including an extended-release hydrogel. Therefore, a multi-arm electro-functional polymer with a lower molecular weight has a higher crosslink density and smaller pore size than a higher molecular weight multi-arm polymer.

The crosslinking density may also be controlled by the concentrations of the nucleo-functional polymer and the electro-functional polymer. Increasing the total concentration increases the cross-linking density as the likelihood or probability that an electro-functional group will combine with a nucleo-functional group and form a crosslink increases. Crosslink density may also be controlled by adjusting the relative amount of nucleo-functional polymer and electro-functional polymer used. A molar ratio of thio-functional groups to thiol-reactive groups of about 1:1 leads to the highest crosslink density.

Degradation Rate of Hydrogels

The length of time over which the one or more pharmaceutical agents can be delivered within the target site (e.g., the eye) and surrounding environment is also a function of the length of time a hydrogel, including an extended-release hydrogel, is present within the site, i.e., degradation rate or degradation time of the hydrogel, including an extended-release hydrogel. Degradation rate or time can be thought of as the rate or length of time it takes for the hydrogel to be completely in solution, i.e., for no solid mass to remain or be observed. In certain embodiments, degradation rate or time can be measured by placing the hydrogel in a solution of PBS, including for example PBS, and assaying for the presence of the hydrogel (solid mass) over time. Degradation rate or time may also be driven by the amount of endogenous enzymes (for example hyaluronidase in the case of an HA based hydrogel) in the local tissues. Degradation rate or time may also be measured at different temperatures (e.g., 37° C. or 60° C.) with higher temperature leading to a faster degradation rate and faster time to complete degradation. In certain embodiments, the degradation time of the hydrogels described herein, including extended-release hydrogels, is greater than or equal to about 20, 40, 60, 69, 80, 90, 94, 100, 120, 140, or 158 days at 37° C. In some embodiments, the degradation time of the hydrogels described herein, including extended-release hydrogels, is greater than or equal to about 3, 5, 8, 10, 14, 19, 20, 25, 30, or 32 days at 60° C.

Pharmaceutical Compositions or Formulations

One aspect of the invention provides pharmaceutical compositions or formulations. In certain embodiments, the pharmaceutical composition or formulation comprises (i) a nucleo-functional polymer; (ii) a pharmaceutical agent; and (iii) a pharmaceutically acceptable carrier for administration to the desired target site. In some embodiments, the pharmaceutical composition or formulation comprises (i) an electro-functional polymer; (ii) a pharmaceutical agent; and (iii) a pharmaceutically acceptable carrier for administration to the desired target site. In certain embodiments, the pharmaceutical composition or formulation comprises (i) a nucleo-functional polymer; (ii) an electro-functional polymer; (iii) a pharmaceutical agent; and (iv) a pharmaceutically acceptable carrier for administration to the desired target site. In some embodiments, the target site is the eye of a subject. In certain embodiments, the target site is the eye of a human. In some embodiments, the pharmaceutical composition or formulation is a liquid pharmaceutical composition or composition. In certain embodiments, the pharmaceutical composition or formulation is a lyophilized pharmaceutical composition or formulation. In some embodiments, the pharmaceutically acceptable carrier is PBS, water, or a combination thereof. In certain embodiments, the pharmaceutically acceptable carrier is 5X PBS, water, or a combination thereof.

In certain embodiments, the pharmaceutical composition or formulation is sterile and may optionally comprise a preservative, antioxidant, and/or other excipients. Exemplary excipients include, for example, acacia, agar, alginic acid, bentonite, carbomers, carboxymethylcellulose calcium, carboxymethylcellulose sodium, carrageenan, *ceratonia*, cetostearyl alcohol, chitosan, colloidal silicon dioxide, cyclomethicone, ethylcellulose, gelatin, glycerin, glyceryl behenate, guar gum, hectorite, hyaluronic acid, hydrogenated vegetable oil type I, hydroxyethyl cellulose, hydroxyethylmethyl cellulose, hydroxypropyl cellulose, hydroxypropyl starch, hypromellose, magnesium aluminum silicate, maltodextrin, methylcellulose, polydextrose, polyethylene glycol, poly(methylvinyl ether/maleic anhydride), polyvinyl acetate phthalate, polyvinyl alcohol, potassium chloride, povidone, propylene glycol alginate, saponite, sodium alginate, sodium chloride, stearyl alcohol, sucrose, sulfobutylether (3-cyclodextrin, tragacanth, xanthan gum, and derivatives and mixtures thereof. In some embodiments, the excipient is a bioadhesive or comprises a bioadhesive polymer.

In some embodiments, the concentration of the excipient in the pharmaceutical composition or formulation ranges from about 0.1 to about 20% by weight. In certain embodiments, the concentration of the excipient in the pharmaceutical composition or formulation ranges from about 5 to about 20% by weight. In certain embodiments, the concentration of the excipient in the pharmaceutical composition or formulation is less than about 20%, less than about 15%, less than about 10%, less than about 9%, less than about 8%, less than about 7%, less than about 6%, less than about 5%), less than about 4%, less than about 3%, less than about 2%, less than about 1.8%, less than about 1.6%, less than about 1.5%, less than about 1.4%, less than about 1.2%, less than about 1%, less than about 0.9%, less than about 0.8%, less than about 0.7%, less than about 0.6%, less than about 0.5%, less than about 0.4%, less than about 0.3%, less than about 0.2%, or less than about 0.1% by weight.

The pharmaceutical composition or formulation may be further characterized according to its viscosity. In certain embodiments, the viscosity of the pharmaceutical composition is less than about 4000 cP, less than about 2000 cP, less than about 1000 cP, less than about 800 cP, less than about 600 cP, less than about 500 cP, less than about 400 cP, less than about 200 cP, less than about 100 cP, less than about 80 cP, less than about 60 cP, less than about 50 cP, less than about 40 cP, less than about 20 cP, less than about 10 cP, less than about 8 cP, less than about 6 cP, less than about 5 cP, less than about 4 cP, less than about 3 cP, less than about 2 cP, less than about 1 cP. In some embodiments, the viscosity of the pharmaceutical composition or formulation is at least about 4,000 cP, at least about 2,000 cP, at least about 1,000 cP, at least about 800 cP, at least about 600 cP, at least about 500 cP, at least about 400 cP, at least about 200 cP, at least about 100 cP, at least about 80 cP, at least about 60 cP, at least about 50 cP, at least about 40 cP, at least about 20 cP, at least about 10 cP, at least about 8 cP, at least about 6 cP, at least about 5 cP, at least about 4 cP, at least about 3 cP, at least about 2 cP, at least about 1 cP. In certain embodiments, the viscosity of the pharmaceutical composition or formulation is about 4,000 cP, about 2,000 cP, about 1,000 cP, about 800 cP, about 600 cP, about 500 cP, about 400 cP, about 200 cP, about 100 cP, about 80 cP, about 60 cP, about 50 cP, about 40 cP, about 20 cP, about 10 cP, about 8 cP, about 6 cP, about 5 cP, about 4 cP, about 3 cP, about 2 cP, about 1 cP. In some embodiments, the viscosity of the viscosity of the pharmaceutical composition or formulation is between about 5 cP and about 50 cP.

In some embodiments, the pharmaceutical composition or formulation may be further characterized according to its pH. In certain embodiments, the pharmaceutical composition or formulation has a pH in the range of from about 5 to about 9, or about 6 to about 8. In certain embodiments, the pharmaceutical composition or formulation has a pH in the range of from about 6.9 to about 7.2 or about 6.8 to about 7.6. In certain embodiments, the pharmaceutical composition or formulation has a pH of about 7.

In certain embodiments, the pharmaceutical composition or formulation comprises water, and the composition or formulation has a pH in the range of about 6.9 to about 7.7. In certain embodiments, the pharmaceutical composition or formulation comprises water, and the composition or formulation has a pH in the range of about 7.1 to about 7.6, about 7.1 to about 7.5, about 7.1 to about 7.4, about 7.2 to about 7.6, about 7.2 to about 7.5, about 7.2 to about 7.4, about 7.2 to about 7.3, about 7.3 to about 7.7, about 7.3 to about 7.6, about 7.3 to about 7.5, about 7.3 to about 7.4, about 7.4 to about 7.7, about 7.4 to about 7.6, or about 7.4 to about 7.5. In certain embodiments, the pharmaceutical composition or formulation comprises water, and the composition or formulation has a pH in the range of about 7.3 to about 7.5. In certain embodiments, the pharmaceutical composition or formulation comprises water, and the composition or formulation has a pH of about 7.4.

The pharmaceutical composition or formulation may be further characterized according to its osmolality and the presence and/or identity of salts. For example, in certain embodiments, the pharmaceutical composition or formulation has an osmolality in the range of about 200 mOsm/kg to about 400 mOsm/kg. In certain embodiments, the pharmaceutical composition or formulation has an osmolality in the range of about 250 mOsm/kg to about 350 mOsm/kg. In certain embodiments, the pharmaceutical composition or formulation has an osmolality in the range of about 260 mOsm/kg to about 310 mOsm/kg. In certain embodiments, the pharmaceutical composition or formulation has an osmolality of about 300 mOsm/kg. In certain embodiments, the pharmaceutical composition or formulation further comprises an alkali metal salt. In certain embodiments, the pharmaceutical composition or formulation further comprises an alkali metal halide salt, an alkaline earth metal halide salt, or a combination thereof. In certain embodiments, the pharmaceutical composition or formulation further comprises sodium chloride. In certain embodiments, the pharmaceutical composition or formulation further comprises sodium chloride, potassium chloride, calcium chloride, magnesium chloride, or a combination of two or more of the foregoing. In certain embodiments, the pharmaceutical composition or formulation comprises phosphate buffered saline (PBS), including for example 1X or 5X PBS. In some embodiments, the PBS comprises one or more of sodium chloride, potassium chloride, sodium phosphate and potassium phosphate.

The pharmaceutical composition or formulation may be further characterized according to the level of endotoxins present in the composition or formulation. In certain embodiments, the composition or formulation has an endotoxin level of less than about 20 endotoxin units/ml, less than about 15 endotoxin units/ml, less than about 10 endotoxin units/ml, less than about 5 endotoxin units/ml, less than about 2.5 endotoxin units/ml, less than about 1.0 endotoxin units/ml, less than about 0.8 endotoxin units/ml, less than about 0.5 endotoxin units/ml, less than about 0.2 endotoxin units/ml, or less than about 0.1 endotoxin units/ml.

The pharmaceutical composition or formulation may also be characterized by the size and number of any particles, including any drug particles, present in the composition or formulation. In certain embodiments, the composition or formulation has less than about 50 particles per mL with a size of ≥10 µm. In some embodiments, the composition or formulation has less than about 5 particles per mL with a size of ≥25 µm.

Kits for Use in Medical Applications

Another aspect of the invention provides a kit for treating a disorder. In certain embodiments, the kit comprises: i) a formulation comprising a nucleo-functional polymer and ii) a formulation comprising an electro-functional polymer. In certain embodiments, the kit comprises: i) a formulation comprising a nucleo-functional polymer and a pharmaceutical agent and ii) a formulation comprising an electro-functional polymer. In some embodiments, the kit comprises: i) a formulation comprising a nucleo-functional polymer and ii) a formulation comprising an electro-functional polymer and a pharmaceutical agent. In some embodiments, the kit comprises: i) a formulation comprising a nucleo-functional polymer and a pharmaceutical agent and ii) a formulation comprising an electro-functional polymer and a pharmaceutical agent. In certain embodiments, the kit comprises: i) a formulation comprising a nucleo-functional polymer; ii) a formulation comprising a pharmaceutical agent, and iii) a formulation comprising an electro-functional polymer. In some embodiments the one or more the formulations provided in the kit comprises a pharmaceutically acceptable carrier. In certain embodiments, the pharmaceutically acceptable carrier comprises PBS. In certain embodiments, the pharmaceutically acceptable carrier is 1X PBS. In some embodiments, the pharmaceutically acceptable carrier is 5X PBS. In some embodiments, the kit further comprises instructions for administering the formulations to a target site of interest in a subject, for example, the eye of a subject. In some embodiments, the kit further comprises the components and/or accessories required to prepare and administer the formulations to a target site of interest in a subject, for example the eye of a subject.

The description above describes multiple aspects and embodiments of the invention. The patent application specifically contemplates all combinations and permutations of the aspects and embodiments.

Medical Devices and Methods for Focal Delivery of Hydrogel-Forming Formulations and Compositions Certain embodiments for forming a hydrogel in a tissue of interest, for example, forming a hydrogel that acts as a retinal tamponade in the vitreous cavity of the eye comprise forming the hydrogel by filling the majority of the air-filled posterior chamber cavity of the eye with the polymer composition or formulation that forms that hydrogel. In such embodiments, the air-filled vitreous cavity becomes a largely hydrogel-filled area with a small layer of air or saline above the gel line in the posterior chamber of the eye. For such embodiments, pre-clinical work was conducted and determined that the gel is well tolerated and does not result in adverse events in an animal vitrectomy model.

Figure 6:
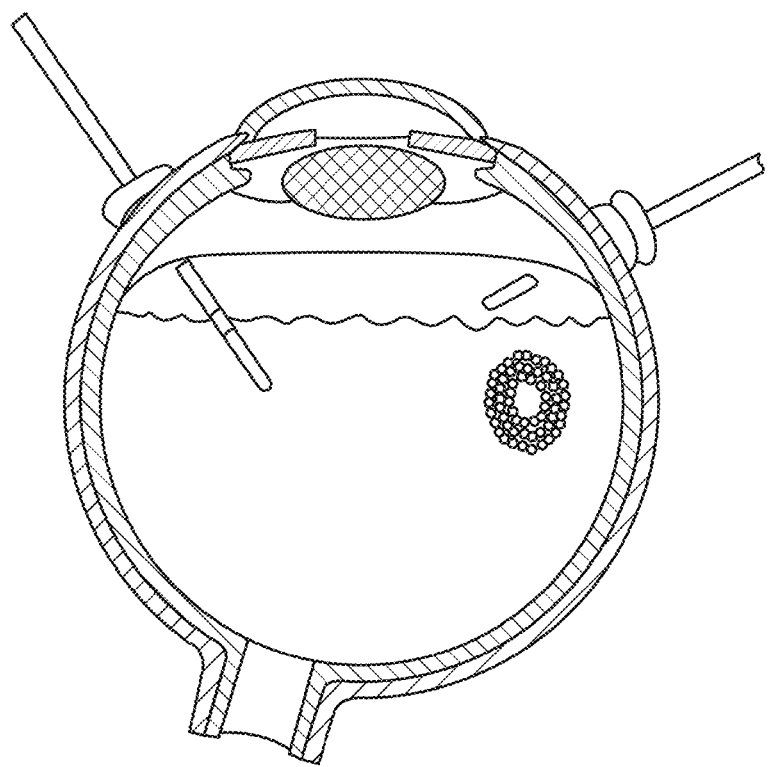
FIG. 6 shows injection of an exemplary hydrogel-forming composition filling the eye and covering a retinal break.

In some embodiments, however, large volumes of hydrogel may result in certain adverse events, namely elevated intraocular pressure as the large amount of hydrogel breaks down and is cleared from the eye. In some embodiments, these adverse events appear to correlate with the large volume of polymer composition or formulation introduced in the eye and the large amount of resulting hydrogel in the eye in order for the gel to fill the posterior chamber and seal all the retinal breaks; retinal breaks typically occur on the edges of the retina, therefore one has to use a significant amount of hydrogel to cover the breaks completely (FIG. 6).

In certain embodiments, mitigation efforts to reduce the risk of elevated intraocular pressure in the design of the hydrogel may be implemented at a molecular level and/or in the surgical technique employed to deliver the gel intraoperatively. Molecular level changes may include the chemical structure of the polymer backbones used, length and weight of the polymer backbones described herein, percent thiolation, percent of solids, and degree of cross linking density that may be used as described herein. In certain embodiments, surgical technique and intraoperative considerations to reduce these adverse events may include not filling the eye completely with the hydrogel-forming polymer or hydrogel itself to the pars plana (the anatomical structure at the edge of the retina), thereby reducing the volume of the formulations and compositions disclosed herein injected and subsequently cleared from the eye. However, these mitigation efforts may not be enough to control elevated intraocular pressure from the hydrogel in certain circumstances and, as described further below, different and new approaches may be required for developer a more clinically useful product.

In certain embodiments, to mitigate the potential risk of intraocular pressure rise, that the inventors determined that one may need to inject less foreign material (e.g., the disclosed polymer formulations and compositions) into the eye. Thus, in certain embodiments in order to target only the site of hydrogel deposition, for example, the site of a retinal tear in the eye, minimal amounts of the hydrogel material formed by the polymer compositions and formulations described herein may be used. Therefore, in certain embodiments a delivery device that allows for focal administration of the hydrogel formed by the polymer compositions and formulations described herein, to specific areas of interest may be employed. Such areas include the vitreous cavity and formation of a retinal tamponade at a target site in order to minimize the amount of hydrogel injected into the target tissue, such as the eye. In certain embodiments, specialized applicators are used to provide the polymer compositions described herein at a target site, including devices to mist or spray, atomize, brush on, roll on, or any other mechanism by which the hydrogel-forming compositions and formulations are mechanically directed or targeted to a specific area of the tissue (e.g., retinal surface).

Devices and methods for focally applying the polymers and hydrogels described herein to tissue target sites of interest, including the vitreous cavity, just to the areas requiring the hydrogel, such as the formation of a retinal tamponade at a target site of pathology are described herein. The unique features of the herein described polymer formulations and compositions and hydrogels may prevent the application of the hydogel "as-is" in a focal manner to a target site, such as a retinal break. In certain embodiments, the hydrogel-forming polymer compositions and formulations described herein at time of initial application are a non-viscous liquid and retinal breaks are almost always at the anterior aspect of the retina (vertically, on the sides of the eye wall). Application of any appreciable volume of a non-viscous liquid to a retinal break would then result in the composition and/or resulting hydrogel running down the eye wall posteriorly. This would result in a failure to apply the gel to the site of pathology and would not satisfy the requirement, in certain embodiments, of introducing a minimal amount of polymer formulation or composition or hydrogel to ensure improved clinical safety. Although the hydrogel-forming compositions or formulations described herein could be made to be viscous by increasing the molecular weight of the individual components, adding a viscosity modifier excipient, or by increasing the percent solids, in certain embodiments this would be undesired as it would increase the overall amount of solid material in the eye and increase the risk of an intraocular pressure rise. Thus, in certain embodiments there is a need to transform the flow properties of the polymer formulations and compositions described herein without changing its chemical constituents.

In the specific example of the eye, others have recognized that retinal breaks may be sealed by applying a "patch" to the retinal break. (See Ren, X. J., Bu, S. C., Wu, D., Liu, B. S., Yang, F. H., Hu, B. J., et al. (2019). PATCHING RETINAL BREAKS WITH HEALAFLOW IN 27-GAUGE VITRECTOMY FOR THE TREATMENT OF RHEGMATOGENOUS RETINAL DETACHMENT; K Teruyal, J Sucdal, M Arai 1, N Tsurumarul, R Yamakawa!, A Hirata2 and T Hirose3. Patching retinal breaks with Seprafilms in experimental rhegmatogenous retinal detachment of rabbit eyes Eye (2009) 23, 2256-2259; Schwartz 2000, Medicus 2017). The unique features of the hydrogel system described herein, however, generally do not allow for application as a solid patch and therefore, the inventors have developed methods and devices. In certain embodiments, using the herein described polymers and hydrogel systems as a patch may have undesirable results. For example, in certain embodiments due to the non-viscous nature of the polymer compositions and hydrogel prior to cross-linking, a jet stream may emerge when attempting to gently "patch" retinal breaks. Such a jet stream could potentially damage the very sensitive retina or underlying structures. In certain embodiments, even single drops of the polymer formulation or hydrogel system may be too watery (of low viscosity), causing the formulation to roll down the side of the peripheral retinal wall down to the posterior pole of the eye rendering it ineffective at providing any sealant effect at the site of the peripheral retinal wall.

Figure 8:
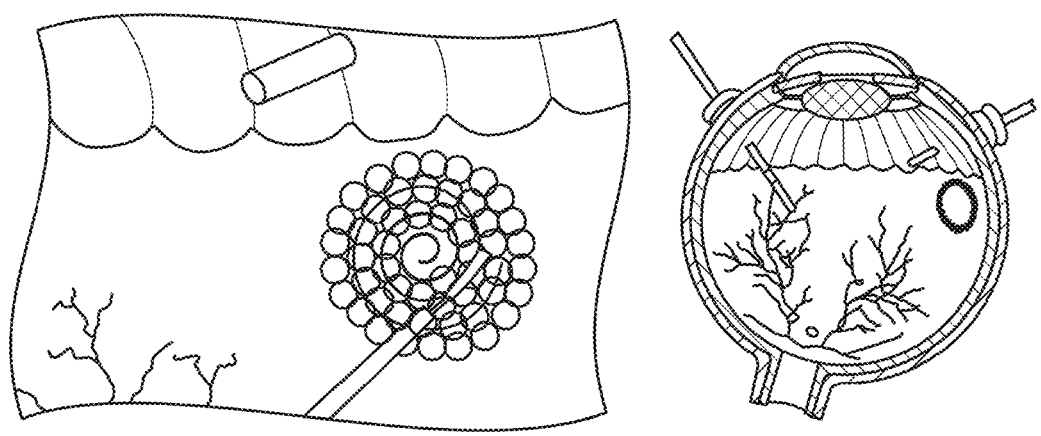
FIG. 8 shows focal administration of an exemplary hydrogel-forming composition that acts as a tamponade agent and focal retinal sealant that remains in place when applied to the retinal surface.

Through the course of experimentation, the inventors have found that the unique features of the polymers and hydrogels described herein may be employed in a method to focally apply the formulations and/or hydrogel to a retinal break by gently brushing the polymer formulation or composition, or the hydrogel, onto the site while the material is in its viscous phase, but before it becomes a semi-solid gel. As described above, in certain embodiments the gel solution is initially a non-viscous liquid immediately after mixing. However, in some embodiments as the solution begins to crosslink, the viscosity begins to increase. Based on the particular formulation employed as described herein (percent polymer in the solution, molecular weight of the polymers, number of reactive side groups, etc.) the change in viscosity at room temperature, the temperature under which the solution is being applied, occurs over ~ 5-20 minutes. In certain embodiments, once the viscosity of the formulation or gel solution reaches a certain level, in the range of 500-1000 cps, the formulation or gel solution will stay where placed on the retina and not run down the eye wall posteriorly (FIG. 8). This is referred to as the beginning of the "application window."

Figure 9:
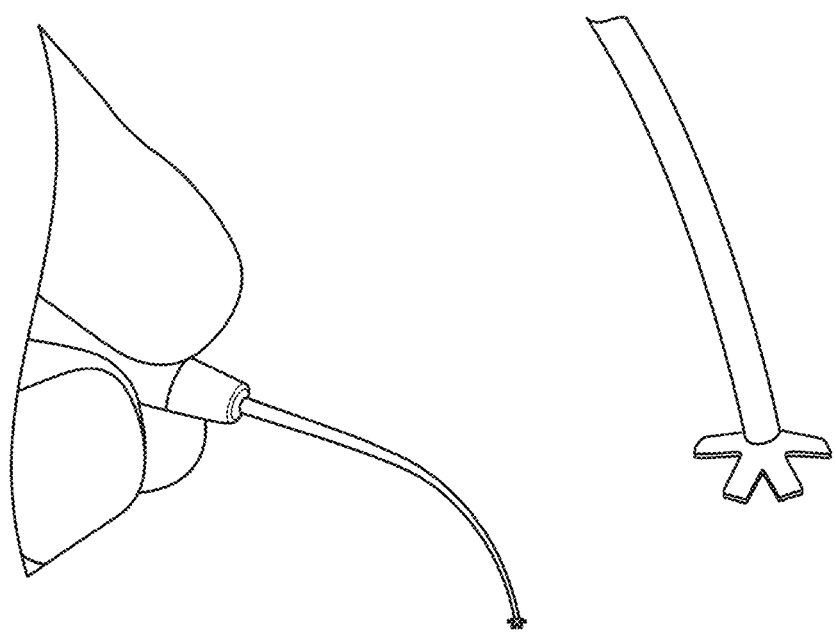
FIG. 9 shows an exemplary curved, brush-tip cannula for intraocular manipulation of a polymer formulation or hydrogel on the retinal surface.

In some embodiments, once the formulation or gel solution reaches a viscosity of greater than ~ 5,000-10,000 cps, it becomes too viscous to apply in a smooth layer and will not adhere effectively to the site of application. This is referred to as the end of the application window. The formulation or hydrogel in this manner may be applied by using a soft-tip cannula with or without slits in the soft-tip acting as brush bristles, thus applying the formulation or hydrogel by brushing it into place, to allow for a targeted and precise application. (FIG. 9). Alternatively, in certain embodiments the distal tip may be comprised of a soft porous foam through which the viscous formulation or hydrogel solution may be injected and brushed onto the surface of the target site, such as the retina.

Figure 7:
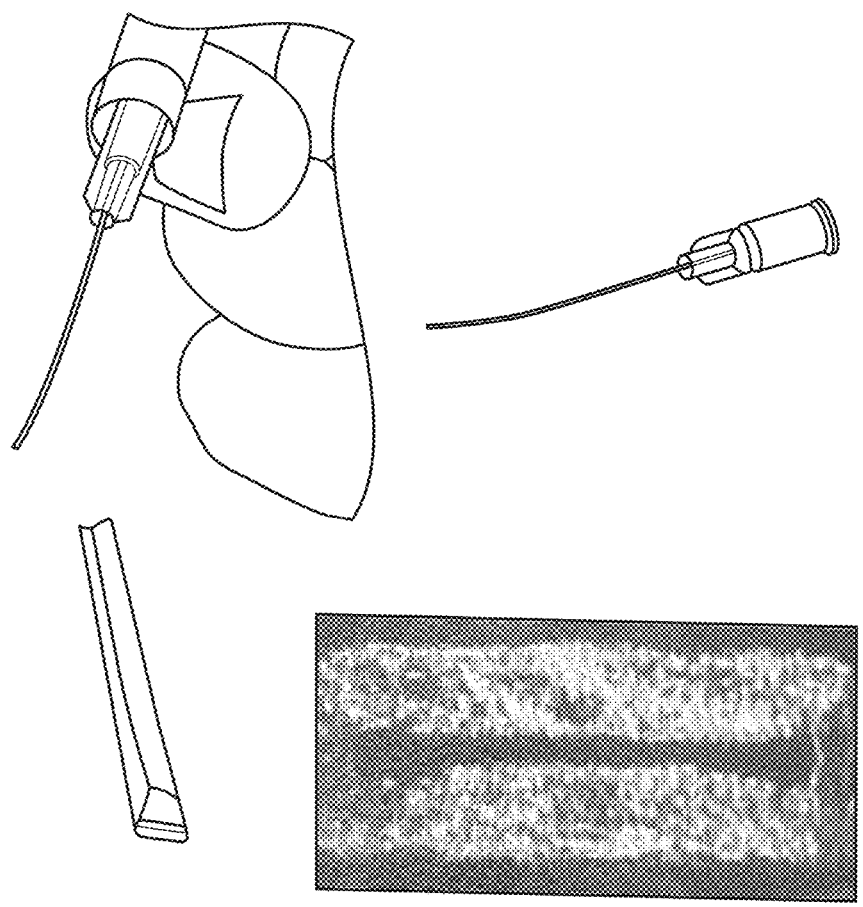
FIG. 7 shows a cannula as described herein with a fabricated 20 micron aperture to permit emergence of polymer formulation of hydrogel as a mist when injected under high pressure.

In certain embodiments, the cannula may be straight or curved. Various cannula designs can be used including curved and un-curved cannulas with various manipulations to the distal portion to create precise channels, grooves, and/or apertures that would allow for the formulations and/or gel to emerge as a mist. (FIG. 7) In some embodiments, a curved cannula may be desirable for directing the tip towards the target site, such as the side wall without striking the natural crystalline lens, which would result in a cataract forming if inadvertently struck. In some embodiments, certain cannulas may be made of pliable metals, such as nitinol, to allow for the comfortable passage through valved entry cannula in the target site, such as the pars plana. It can be applied by hand force with a syringe or through an automated system, such as the viscous fluid injector. Other embodiments of the cannula may be used to deliver precise amounts of polymer formulation and/or hydrogel comprising a therapeutic agent, such as an active pharmaceutical ingredient in the form of a small molecule, peptide, oligonucleotide, viral vector, or even a dye, or other agent to a specific part of the tissue, such as the eye or other organ. In certain embodiments, such agents may be used to provide protection against infection, inflammation, anti-proliferation, malignancy, amongst other uses.

Methods of application need not be limited to focal areas where retinal breaks are present. Such a cannula could be used to apply any liquid substance focally into the eye or any other tissue where a focal sealant or hydrogel is clinically desirable. Examples in the eye include, but are not limited to, applying to macular holes, retinal lesions, membranes, or other vitreoretinal indications.

Kits for Use in Medical Applications

Another aspect of the invention provides a kit for treating a retinal defect. In certain embodiments, the kit comprises: i) a lyophilized nucleo-functional polymer, ii) a lyophilized electro-functional polymer, (iii) a pharmaceutically acceptable carrier in a vial or a pre-filled syringe for reconstituting the nucleophilic and electrophilic polymers, (iv) syringes, (v) needles or vial access devices for aseptic transfer of solutions and (vi) a soft-tip cannula for application to the retina.

Citations are made to the following references, each of which is incorporated by reference herein in its entirety: U.S. Pat. Nos. 10,874,767; 6,149,931; 9,623,144; and 9,072,809; Ren, X. J., Bu, S. C., Wu, D., Liu, B. S., Yang, F. H., Hu, B. J., et al. (2019). PATCHING RETINAL BREAKS WITH HEALAFLOW IN 27-GAUGE VITRECTOMY FOR THE TREATMENT OF RHEGMATOGENOUS RETINAL DETACHMENT. Retina (Philadelphia, Pa.), Publish Ahead of Print. http://doi.org/10.1097/IAE.0000000000002701; and K Teruyal, J Suedal, M Arail, N Tsurumarul, R Yamakawal, A Hirata2 and T Hirose3. Patching retinal breaks with Seprafilms in experimental rhegmatogenous retinal detachment of rabbit eyes Eye (2009) 23, 2256-2259

EXAMPLES

The following examples are included merely for purposes of illustration of certain aspects and embodiments of the present invention and are not intended to limit the invention.

Example 1—Characteristics of Exemplary Thiolated Hyaluronic Acid Polyethylene Glycol Diacrylate Hydrogel Formulations

Example 1A

Figure 5:
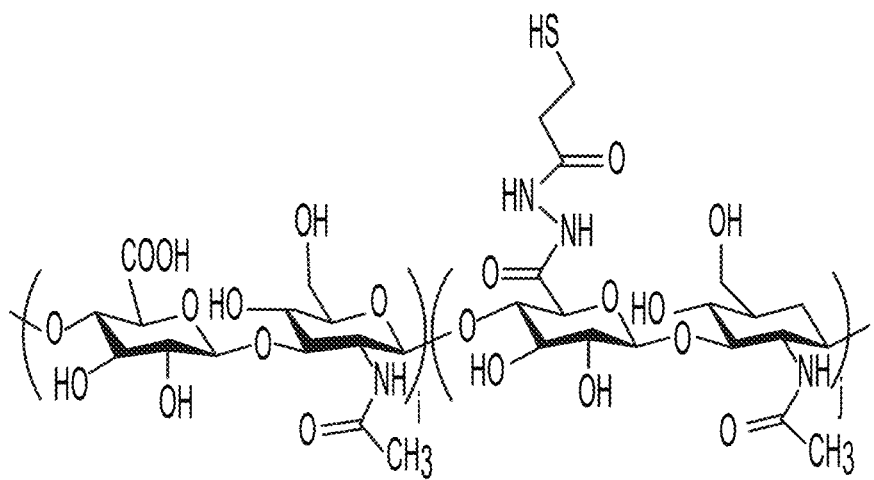
FIG. 5 shows the formation and degradation of an exemplary hydrogel described herein, PYK-2101.
Figure 5:
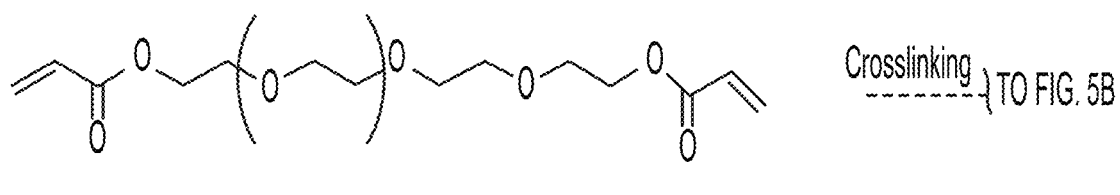
Figure 5:
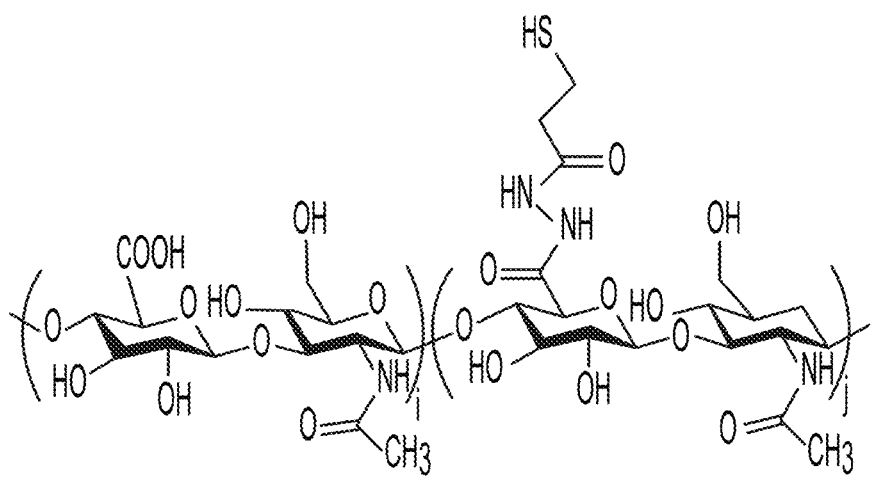
Figure 5:
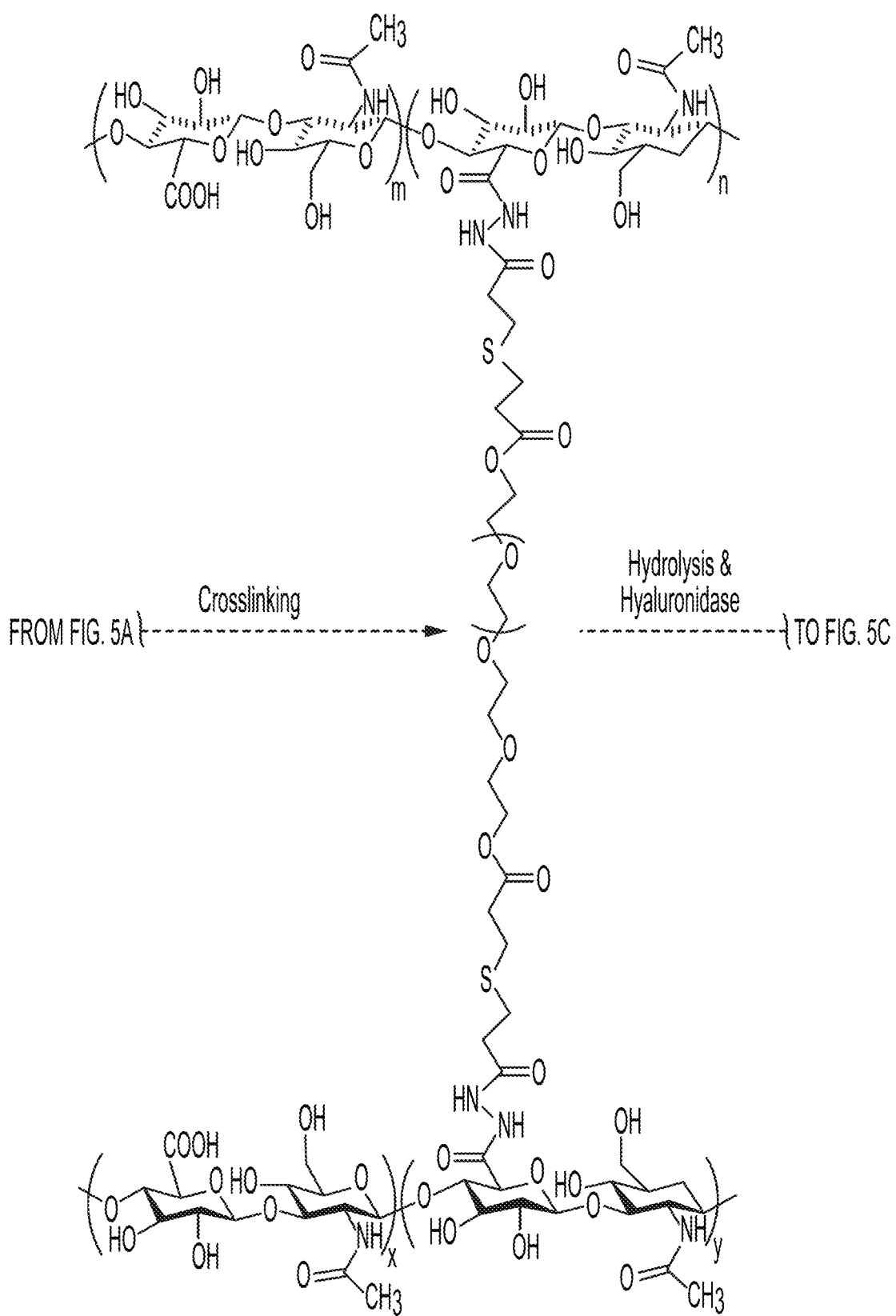
Figure 5:
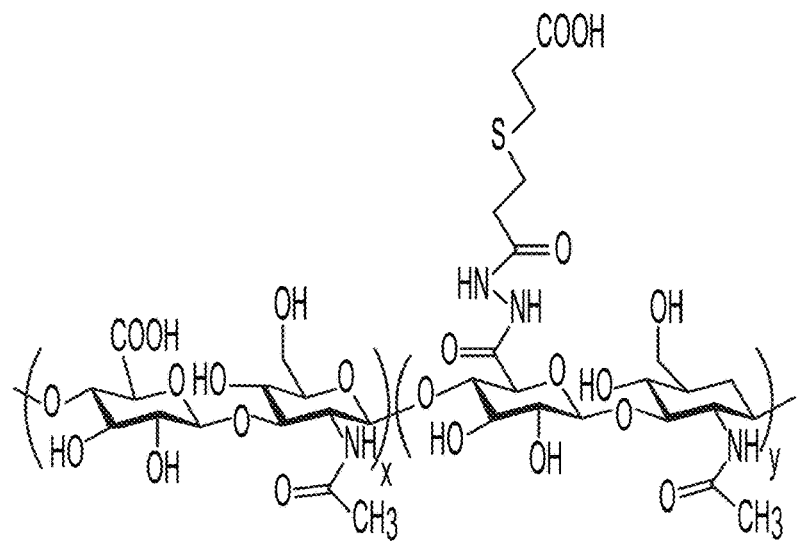
Figure 5:
Figure 5:
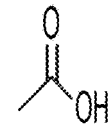
Figure 5:
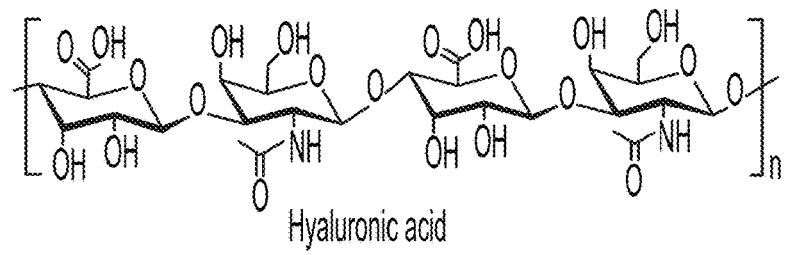
Figure 5:
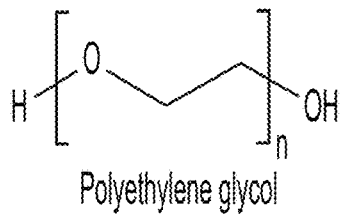
Figure 5:
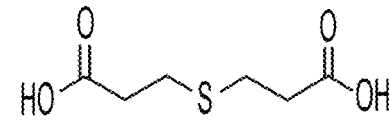
Figure 5:
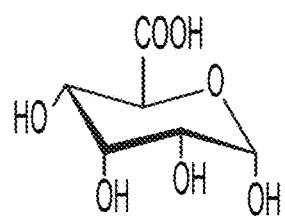
Figure 5:
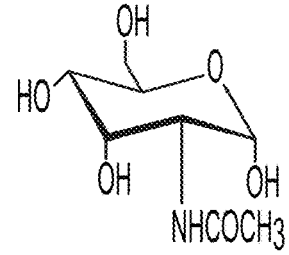

Crosslinking performance was evaluated comparing various combinations of a thiolated hyaluronic acid (tHA) and polyethylene diacrylate (PEGDA) (see, e.g., FIG. 5).

Glycosil® thiol-modified hyaluronan (Catalog #GS220F) was purchased from Advanced Biomaterial Inc. (Carlsbad, CA). GS220F is a 50 mg lyophilized preparation of 75-125 kDa hyaluronic acid with 20-30% thiol-modification. PEGDA with a molecular weight of 3 kDa was prepared as a 75 mg lyophilized powder.

Phosphate buffered saline (1X or 5X PBS) was added to 50 mg of lyophilized tHA and to 75 mg of lyophilized PEGDA to obtain various concentrations of tHA and PEGDA solutions. tHA and PEGDA solutions were combined at various ratios and briefly mixed. In some cases the pH of the tHA solution was increased by adding sodium hydroxide and the final pH of the tHA solution after reconstitution and adjustment were recorded. 1 mL of the combined solution was drawn into a 1 mL syringe and a 26G cannula was attached.

Approximately 25-30 uL of the hydrogel solution was then periodically applied to a glass slide mounted vertically and consistency observed. The time to become viscous (as defined by a smooth layer that remained in place on the vertical surface without run-off) and the application widow (as defined as the time from when the solution first becomes viscous to when the solution becomes difficult to inject or cannot be applied as a smooth layer) were recorded, and are provided in Table 1 below. Testing was performed at room temperature (~22° C.).

TABLE 1

| Sample | A | B | C | D | E | F | G | H | I |
|---|---|---|---|---|---|---|---|---|---|
| PBS | 1X | 5X | 5X | 5X | 5X | 5X | 5X | 5X | 5X |
| tHA pH | 6.0 | 7.0 | 7.1 | 6.8 | 6.6 | 7.4* | 7.0* | 7.4 | 6.9 |
| % tHA | 1.0 | 1.0 | 1.0 | 2.4 | 2.9 | 2.4 | 2.4 | 2.0 | 2.0 |
| % PEGDA | 1.0 | 1.0 | 1.0 | 4.3 | 5.0 | 4.3 | 4.3 | 3.0 | 3.0 |
| tHA: PEGDA | 8:1 | 8:1 | 4:1 | 1:1 | 1:1 | 1:1 | 1:1 | 1:1 | 1:1 |
| Time to viscous | N/A | 107 min | 48 min | 9 min | 8 min | 4 min | 6 min | 6 min | 11 min |
| Application Window | N/A | N/A | N/A | N/A | N/A | 40 sec | 1 min | 2 min | 5 min |

*pH adjusted with NaOH

Example 1B

Crosslinking performance was evaluated for a thiolated hyaluronic acid (tHA) and polyethylene diacrylate (PEGDA) hydrogels.

Thiolated hyaluronic acid (Catalog #HASH0203) was purchased from Blafar Ltd (Dublin, Ireland). HASH0203 is a 50 mg lyophilized preparation of 220 kDa hyaluronic acid with 25% thiol-modification. PEGDA with a molecular weight of 3 kDa was prepared as a 75 mg lyophilized powder.

2.5 mL phosphate buffered saline (5X PBS) was added to 50 mg of lyophilized tHA and to 75 mg of lyophilized PEGDA to obtain 2% tHA and 3% PEGDA solutions respectively. tHA and PEGDA solutions were combined at a 1:1 ratio and briefly mixed. In some cases, the pH of the tHA solution was increased by adding sodium hydroxide and the final pH of the tHA solution after reconstitution and adjustment were recorded. 1 mL of the combined solution was drawn into a 1 mL syringe and a 26G cannula was attached.

Approximately 25-30 uL of the hydrogel solution was then periodically applied to a glass slide mounted vertically and consistency observed. The time to become viscous (as defined by a smooth layer that remained in place on the vertical surface without run-off) was recorded, and is provided in Table 2 below. Testing was performed at room temperature (~22° C.)

TABLE 2

| Sample | A | B |
|---|---|---|
| PBS | 5X | 5X |
| tHA pH | 6.6 | 7.4* |
| % tHA | 2.0 | 2.0 |
| % PEGDA | 3.0 | 3.0 |
| Time to Viscous | 27 min | 12 min |

*pH adjusted with NaOH

Example 2—Degradation of Exemplary Thiolated Hyaluronic Acid Polyethylene Glycol Diacrylate Hydrogel Formulations Hyaluronic acid is a naturally occurring polymer. HA is degraded in-vivo by the hyaluronidase enzyme. Thiolated HA hydrogels can degrade by both enzymatic and hydrolytic degradation. The rate of degradation is dependent on the $R^1$—SH linker structure and the concentration of hyaluronidase in solution. The rate of degradation of exemplary tHA: PEGDA hydrogels was evaluated in-vitro.

tHA was purchased from Advanced Biomaterials (GS220F) and Blafar (HASH0203). PEGDA with a molecular weight of 3 kDa was prepared as a 75 mg lyophilized powder. tHA and PEGDA solutions were created by dissolving the lyophilized powders in 5×PBS. Hydrogel samples were created by combining solutions of tHA and PEGDA 1:1 and injecting 1 mL of the combined solution into a 20 mL glass scintillation vial. The hydrogels were allowed to crosslink, and then 10 mL of PBS with or without hyaluronidase were added to the vial and the vials placed in a shaker incubator at 37° C. or 60° C. Samples were visually checked daily for presence or absence of a visible solid. In some samples the hyaluronidase solution was removed, and a fresh solution added daily. Time to degradation of the hydrogel under various conditions is provided in Table 3 below.

TABLE 3

| tHA | % tHA | % PEGDA | Degradation Solution | Temperature (° C.) | Time to Degradation (Days) |
|---|---|---|---|---|---|
| Glycosil GS220F | 2.4 | 4.3 | PBS | 60 | 14 |
| HASH0203 | 2.0 | 3.0 | PBS | 60 | 7 |
| 76Glycosil GS220F | 2.0 | 3.0 | 1 U/mL hyaluronidase | 37 | 76 |
| Glycosil GS220F | 2.0 | 3.0 | 1 U/mL hyaluronidase* | 37 | 52 |
| Glycosil GS220F | 2.0 | 3.0 | 5 U/mL hyaluronidase* | 37 | 32 |
| HASH0203 | 2.0 | 3.0 | 1 U/mL hyaluronidase | 37 | 38 |
| HASH0203 | 2.0 | 3.0 | 1 U/mL hyaluronidase* | 37 | 16 |

*Solution changed daily

Example 3—Tolerance in the Eye and Intraocular Pressure from Exemplary Hydrogel Formulations Both thiolated poly(vinyl) alcohol poly(ethylene) glycol diacrylate and thiolated hyaluronic acid poly(ethylene) glycol diacrylate hydrogel formulations are tolerated well in rabbit animal models. However, it was unexpectedly found that thiolated poly(vinyl) alcohol poly(ethylene) glycol diacrylate hydrogel formulations cause elevated, and undesirable, intraocular pressure in human subjects, despite their lower molecular weight.

A rabbit safety study (Study report 19-04175) was performed at Toxikon (Toxikon Corporation, Bedford MA, USA) under GLP conditions to assess the local tissue reaction to and systemic toxicity of PYK-1107, a tPVA formulation described above. Nine New Zealand White Rabbits (3 control, 6 experimental) underwent pars plana vitrectomy, fluid-air exchange, and then randomization to receive either balanced salt solution (control) or hydrogel insertion with PYK-1105 (experimental).

Animals were observed daily for clinical signs of toxicity and underwent complete ophthalmic examinations including measurements of intraocular pressure (IOP) and fundus examinations on post-op days 1, 7, 14, 21, 28 and 56. In all of the rabbits, no significant ophthalmic clinical findings were observed when control animals were compared to experimental animals. The histopathological assessment showed minimal to mild accumulation of basophilic material within macrophages indicating macrophages removing material from the eye via normal drainage routes. Occasionally, as shown in FIG. 1, the macrophages containing basophilic material were observed in the connective tissue adjacent to the optic nerve (1), including within multinucleated giant cells (2) in that location; the retina was normal appearing (3).

There was no significant inflammation or tissue damage detected in any animal. Additionally, there were no signs of systemic toxicity on the systemic pathological assessment. In conclusion, PYK-1107 showed no local or systemic signs of toxicity when implanted in the eyes of rabbits following vitrectomy. Ophthalmic exams, multimodal imaging, electrophysiologic studies and histopathological analyses suggested excellent safety and tolerability in the rabbit eye.

Figure 2:
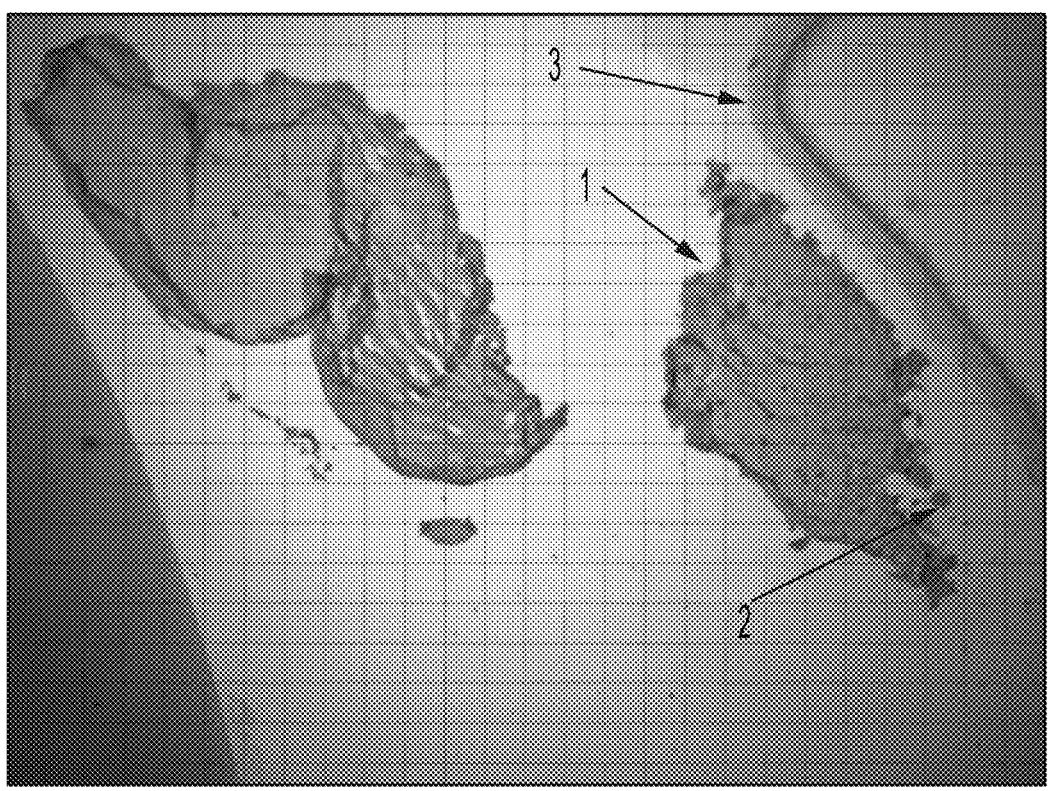
FIG. 2 shows an exemplary histopathological examination of eye tissue sections of rabbits injected intravitreally in both eyes with an exemplary formulation described herein, PYK-2101. The tissue shows (1) variably sized foci of homogeneous basophilic material (consistent with delivery material) in the vitreous (2) minimal granulomatous inflammation, composed of multinucleated giant cells, and (3) the retina appears normal.

A separate study was undertaken to understand the ocular response to PYK-2101, a thiolated hyaluronic acid (tHA) and polyethylene glycol diacrylate (PEGDA) formulation for forming a hydrogel. This non-GLP study (TP-076, TP-076-R) was performed at PARF (Norton MA, USA) to assess the local tissue reaction to PYK-2101. Two New Zealand White rabbits were enrolled in the study. Fifty (50) uL of PYK-2101 was injected intravitreally into both eyes of each rabbit. Animals were assessed twice-weekly for clinical signs and IOP measurements were taken. At two weeks post op and 5 weeks post-op, ocular slit lamp exams were performed to assess for signs of inflammation. Following the 5th week exam, rabbits were euthanized, eyes enucleated and tissues sent for histological examination. All 4 eyes appeared normal on ocular exam at both time points. IOPs remained in the normal range throughout the study in all eyes. In most tissue sections, homogenous basophilic material (consistent with PYK-2101) was present within the vitreous. Histopathological examination was performed and as shown in FIG. 2, demonstrated variably sized foci of homogenous basophilic material (consistent with delivery material) in the vitreous (1) and minimal granulomatous inflammation, composed of multinucleated giant cells (2); retina was normal appearing (3).

Despite rabbits demonstrating excellent IOP tolerance to both tPVA-PEGDA (PYK-1107) and tHA-PEGDA formulations (PYK-2101), significant and undesirable IOP elevation was observed in human subjects who received PYK-1107, an unexpected finding. In Study PYK-1107-RD003, three human subjects with retinal detachments were enrolled and underwent vitrectomy, fluid-air exchange, laser retinopexy, and focal application of PYK-1107 (IPVA-PEGDA formulation). Symptomatic IOP elevations (e.g., >20 mmHg after about three weeks after administration) were observed in all three subjects (1003-001, 1003-002 and 1003-003). All subjects experienced IOP elevations at the time of product degradation and clearance (approximately post-operative month 1), regardless of injection volume (patient 1003-001 received 100 microliters; patient 1003-002 received 50 microliters; patient 1003-003 received 10 microliters).

It was determined that rabbits were not a sufficient preclinical model to evaluate predictiveness of IOP response in humans and using nucleo-functional polymers, such as tPVA, with low molecular weight was insufficient to ensure normal IOP at time of hydrogel breakdown. As a result, a non-human primate model was evaluated as a system for predicting IOP response in human to exemplary hydrogel formulations described herein.

Example 4—Unexpected Result of Normal IOP Response at Time of Degradation Despite Larger Molecular Size of THA-PEGDA Hydrogel Formulation in a Non-Human Primate Model As described above, a human clinical trial was conducted where three subjects were enrolled and underwent vitrectomy, fluid-air exchange, laser retinopexy, and focal application of an exemplary tPVA-PEGDA hydrogel formulation, PYK-1107. The primary adverse event observed was elevated intraocular pressure, which was observed in all three subjects. All subjects experienced IOP elevations at the time of product degradation and clearance (approximately post-operative month 1), regardless of injection volume. PYK-1107 demonstrated early feasibility as a potentially efficacious retinal sealant and alternative to traditional methods of retinal tamponade, but was limited by an unexpected peculiar, but consistent, elevation of intraocular pressure at time of product breakdown in all subjects, regardless of injected volume introduced into the eye and the small molecular weight of the nucleo-functional polymer.

This unexpected, and undesirable, elevation in IOP necessitated the development of a novel methodology employing a different hydrogel formulation that would provide acceptable IOP after administration to the eye. As a result, the inventors developed the use of a formulation based on a hyaluronic acid backbone, despite its higher molecular weight, due to potential advantages such as the possibility to titrate the product degradation in a more controlled fashion to avoid the sudden "burst" of small degradants in the eye upon hydrogel degradation over time, for example at month 1 after administration. Bench testing of several tHA-PEGDA formulation candidates (described in Example 1 above) showed performance characteristics similar to PYK-1107. A lead formulation comprising 2% tHA and 3% PEGDA combined in a 1:1 ratio was selected (internally designated as PYK-2101) and an in vivo rabbit study was performed and demonstrated excellent intraocular tolerance in the rabbit eye (described in Example 3).

To provide the greatest assurance of safety prior to returning to the clinic, a head-to-head comparison of the exemplary tPVA-PEGDA (PYK-1107) formulation and a new tHA-PEGDA (PYK-2101) formulation in a non-human primate (NHP) surgical model (African Green Monkeys) was performed.

Figure 3:
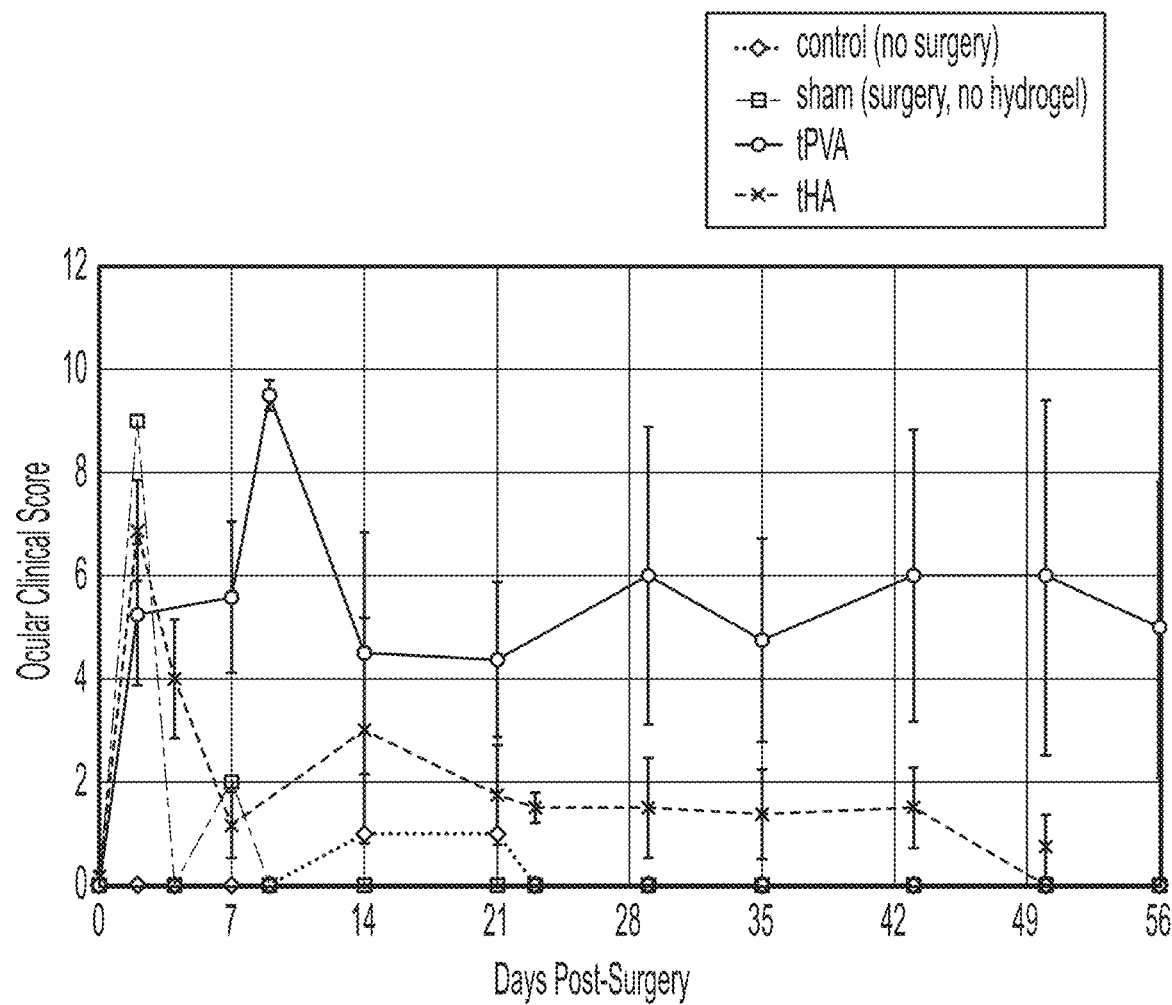
FIG. 3 shows the post-surgery ophthalmic clinical scores of monkeys treated with tPVA or tHA based formulations and resulting hydrogels as described herein.
Figure 4:
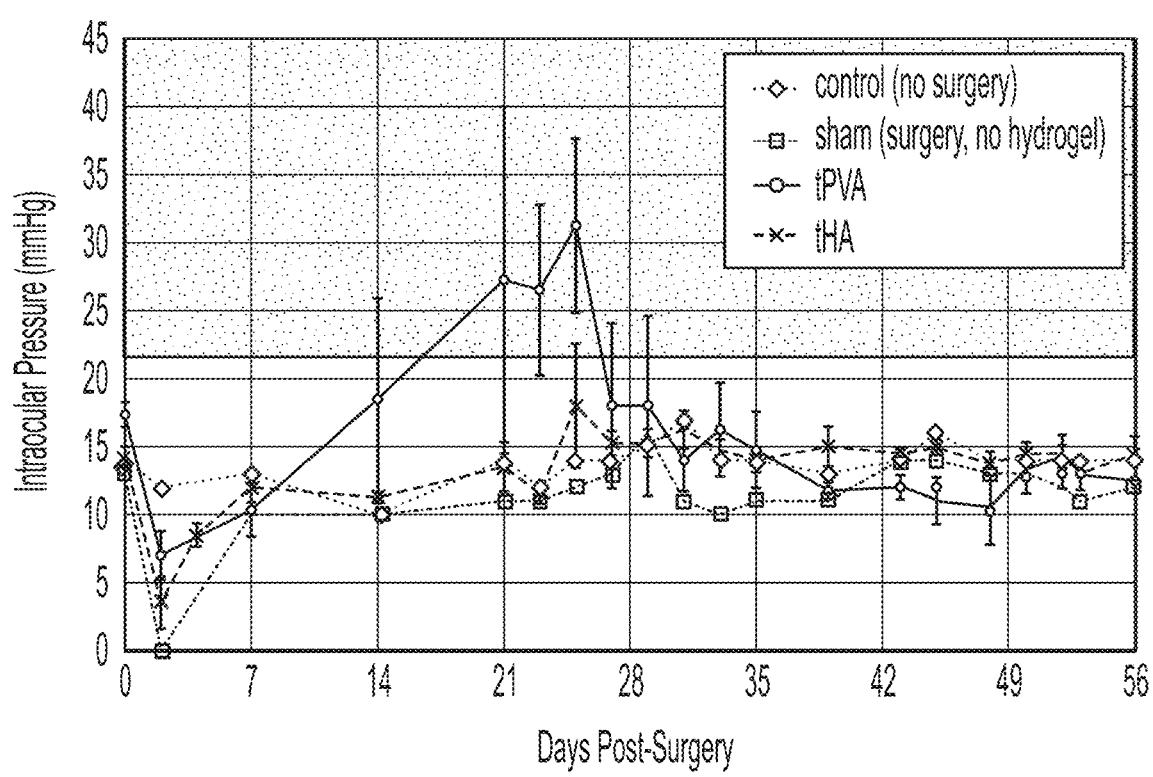
FIG. 4 shows the post-surgery ophthalmic intraocular pressure scores of monkeys treated with tPVA or tHA based formulations and resulting hydrogels as described herein.

The NHP study was performed with treatments groups including no surgery (n=1), sham surgery (vitrectomy without hydrogel injection, n=1), surgery with 100 uL tPVA-PEGDA injection (PYK-1107 formulation, n=4) or surgery with 100 uL tHA-PEGDA injection (PYK-2101 formulation, n=4). The ophthalmic clinical scores were high in all groups immediately post-surgery. After one week, clear differences in ophthalmic clinical scores between the different formulations had emerged. Three of four eyes in the tPVA group had significantly elevated ophthalmic clinical scores compared to both control animals and tHA animals, which had lower ophthalmic clinical scores compared to tPVA. This trend continued through 35 days post-surgery. (FIG. 3). Notably, 75% of eyes treated with the tPVA formulation developed briskly elevated IOP (>40 mmHg) about 4 weeks after administration, sustained on multiple visits, while only a single tHA-treated eye had elevated IOP, at a single visit only (FIG. 4).

Despite the high molecular weight of the thiolated hyaluronic acid formulation (PYK-2101, nucleophile: thiolated hyaluronic acid), it demonstrated unexpectedly normal IOP (10-25 mmHg over time post administration to the subject, whereas the smaller molecular weight thiolated PVA formulation (PYK-1107, nucleophile: thiolated polyvinyl alcohol) resulted in a higher and undesirable IOP (25-40 mmHg) in the eye over time.

Example 5: Exemplary Delivery Kit to for Delivery of Product

Injection of certain hydrogel products into the eye that are currently used on a routine clinical basis, such as ophthalmic viscoelastic devices, is performed by simply removing the sterile cap barrier and attaching the ophthalmic cannula to the luer lock mechanism. The hydrogel-forming formulations described herein are relatively complex and if not properly prepared, carry the risk of failure of the device or an inadvertent adverse event. In certain embodiments, the product is provided in a two-part system, including a Polymer Kit and an Accessory Kit. In some embodiments, the Accessory kit includes the specific components and equipment that have been validated for a particular formulation to achieve safe use of the product. In some embodiments, failure to utilize the kit components may lead to failure of the hydrogel to perform in the intended manner. For example, dissolution and vortexing steps facilitate proper reconstitution; failure to correctly perform reconstitution may result in incomplete solute dissolution, under concentration of solution leading to incomplete hydrogel formation, and thereby potential failure of hydrogel to act as a sealant on the retinal surface. Given particular concentrations of polymers that may be used, in certain embodiments a specific transfer device is included within the Accessory Kit. In some embodiments, the transfer device has a dead space volume that will trap a certain percentage of component upon transfer to the other component. In certain embodiments, this component capture has been determined to create a precise final concentration of hydrogel solution, which creates a desired set of parameters. In some embodiments, failure to use the vial transfer device may result in an imprecise transfer of components and lead to an undesired concentration. In addition, in certain embodiments preparation of the polymer compositions and resulting hydrogel may require the user to repeatedly test and evaluate the viscosity of the hydrogel-forming composition prior to administration. In certain embodiments. failure to properly prepare the hydrogel-forming composition may result in administration of a non-viscous solution, ingress through the retinal break, and failure to achieve retinal re-attachment.

Example 6: Rheology of Thiolated Hyaluronic Acid Polyethylene Glycol Diacrylate Hydrogel Formulations When solutions of thiolated hyaluronic acid (tHA) and PEG diacrylate (PEGDA) are combined, the nucleophilic thiol and the electrophilic acrylate react via a Michael's reaction. As this reaction proceeds, the viscosity of the formulation increases. The viscosity of a 2% tHA, 3% PEGDA formulation was characterized by rotational rheometry.

tHA was purchased from Advanced Biomaterials (GS220F). PEGDA with a molecular weight of 3 kDa was prepared as a 75 mg lyophilized powder. Test samples were prepared as follows. 2.5 mL of 5x PBS was added to the Glycosil vial to create a 2% tHA solution. The tHA solution was vortexed for ~ 30 seconds every 3-4 minutes until the tHA was fully dissolved. Similarly, 2.5 mL of 5x PBS was added to the PEGDA vial to create a 3% PEGDA solution. The PEGDA was completely dissolved in less than 30 seconds.

Once both the tHA and PEGDA were fully dissolved, the complete contents of the tHA vial were withdrawn and injected into the PEGDA vial. The vial containing the tHA:PEGDA solution was briefly swirled for 3-4 seconds, then 1 mL of hydrogel solution was withdrawn and immediately injected into the test chamber of a TA Instruments DH1 rheometer. Testing was performed at 22° C. using a 60 mm 2° stainless steel cone under conditions of 0.1% strain and 6.823 rad/sec. Intrinsic viscosity was recorded continuously for 20 minutes as shown in Table 4 below.

TABLE 4

| TIME (MIN) | VISCOSITY (CPS) | | |
|---|---|---|---|
| | SAMPLE 1 | SAMPLE 2 | SAMPLE 3 |
| 1 | 12 | 5 | 5 |
| 2 | 12 | 6 | 6 |
| 3 | 12 | 6 | 6 |
| 4 | 14 | 9 | 7 |
| 5 | 21 | 15 | 9 |
| 6 | 43 | 32 | 14 |
| 7 | 110 | 87 | 26 |
| 8 | 297 | 244 | 67 |
| 9 | 674 | 584 | 186 |
| 10 | 1210 | 1100 | 463 |
| 11 | 1910 | 1740 | 930 |
| 12 | 2750 | 2530 | 1570 |
| 13 | 4180 | 3450 | 2310 |
| 14 | 4650 | 4440 | 3190 |
| 15 | 5750 | 5480 | 4190 |
| 16 | 6910 | 7200 | 5280 |
| 17 | 8110 | 7740 | 6230 |
| 18 | 9360 | 9000 | 7620 |
| 19 | 10640 | 10220 | 9350 |

INCORPORATION BY REFERENCE

All of the references cited herein are hereby incorporated by reference in their entireties.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A method of contacting retinal tissue in an eye of a subject, the method comprising:
    injecting into the vitreous cavity of the eye of the subject an effective amount of a nucleo-functional polymer and an electro-functional polymer; and
    allowing the nucleo-functional polymer and the electro-functional polymer to react to form a hydrogel in the vitreous cavity, which hydrogel contacts the retinal tissue in the eye, thereby providing a retinal tamponade;
    wherein the nucleo-functional polymer is a biocompatible polymer comprising hyaluronic acid containing a plurality of thio-functional —R$^1$—SH, wherein R$^1$ is hydrolyzable, and the electro-functional polymer is a biocompatible polymer comprising poly(ethylene glycol) containing at least one thiol-reactive group.

2. The method of claim 1, wherein —R$^1$—SH is

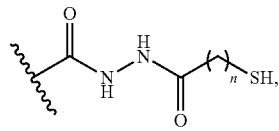

and n=1-3 or n=2.

3. The method of claim 1, wherein —R$^1$—SH is

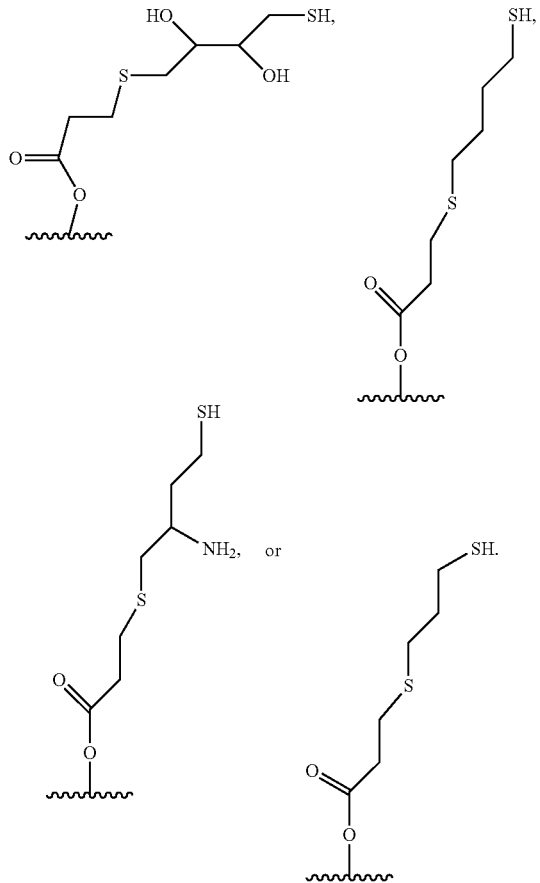

4. The method of claim 1, wherein up to about 200 μL of the nucleo-functional polymer, the electro-functional polymer, or a combination thereof is administered.

5. The method of claim 1, wherein the nucleo-functional polymer and the electro-functional polymer are focally applied in the vitreous cavity.

6. The method of claim 1, wherein the subject is having undergone a vitrectomy for repair of a retinal detachment or macular hole.

7. The method of claim 1, wherein the subject has a physical discontinuity in the retinal tissue, a tear in the retinal tissue, a break in the retinal tissue, or a hole in the retinal tissue.

8. The method of claim 1, wherein the nucleo-functional polymer and the electro-functional polymer are injected separately as liquid aqueous pharmaceutical compositions or together as a single, liquid aqueous pharmaceutical composition to the vitreous cavity of the eye of the subject.

9. The method of claim 8, wherein the separate liquid aqueous pharmaceutical compositions or single liquid aqueous pharmaceutical composition has a pH in the range of about 6.9 to about 7.2 or about 6.8 to about 7.6.

10. The method of claim 1, wherein the hydrogel has a transparency of at least 95% for light in the visible spectrum when measured through the hydrogel having a thickness of 1 cm.

11. The method of claim 1, wherein the hydrogel has a gelation time of less than about 10 minutes.

12. The method of claim 1, wherein the hydrogel undergoes complete biodegradation from the eye of the subject within about 3 days to about 7 days, about 2 weeks to about 8 weeks, or about 4 months to about 6 months, or within 12 months or 24 months.

13. The method of claim 1, wherein the hydrogel has a biodegradation half-life in the range of from about 1 week to about 3 weeks or from about 8 weeks to about 15 weeks when disposed within the vitreous cavity of an eye.

14. The method of claim 1, wherein the hydrogel generates a pressure within the eye of less than 25 mmHg.

15. The method of claim 1, wherein the nucleo-functional polymer has a weight-average molecular weight in the range of from about 75 kDa to about 300 kDa; and the electro-functional polymer has a weight-average molecular weight in the range of from about 500 g/mol to about 1,000,000 g/mol.

16. The method of claim 1, wherein the mole ratio of (i) thio-functional groups —$R^1$—SH to (ii) thiol-reactive groups is about 0.5:1 to about 1.2:1, about 0.6:1 to about 1.2:1, or about 0.67:1.

17. The method of claim 1, wherein the poly(ethylene glycol) is linear, branched, a dendrimer, or multi-armed.

* * * * *